(12) United States Patent
Palli et al.

(10) Patent No.: US 10,190,124 B2
(45) Date of Patent: Jan. 29, 2019

(54) SUBSTITUTION MUTANT RECEPTORS AND THEIR USE IN A NUCLEAR RECEPTOR-BASED INDUCIBLE GENE EXPRESSION SYSTEM

(71) Applicant: Intrexon Corporation, Blacksburg, VA (US)

(72) Inventors: Subba Reddy Palli, Lexington, KY (US); Mohan Basavaraju Kumar, Toronto (CA); Dean Ervin Cress, Souderton, PA (US); Ted Tsutomu Fujimoto, Churchville, PA (US)

(73) Assignee: Intrexon Corporation, Blacksburg, VA (US)

( * ) Notice: Subject to any disclaimer, the term of this patent is extended or adjusted under 35 U.S.C. 154(b) by 12 days.

(21) Appl. No.: 15/069,057

(22) Filed: Mar. 14, 2016

(65) Prior Publication Data

US 2016/0257964 A1    Sep. 8, 2016

Related U.S. Application Data

(63) Continuation of application No. 13/618,693, filed on Sep. 14, 2012, now Pat. No. 9,322,026, which is a continuation of application No. 10/468,193, filed as application No. PCT/US02/05090 on Feb. 20, 2002, now Pat. No. 8,715,959.

(60) Provisional application No. 60/313,925, filed on Aug. 21, 2001, provisional application No. 60/269,799, filed on Feb. 20, 2001.

(51) Int. Cl.

| | |
|---|---|
| C12P 21/06 | (2006.01) |
| C12N 15/63 | (2006.01) |
| C07K 14/705 | (2006.01) |
| C07K 14/72 | (2006.01) |
| C12P 21/02 | (2006.01) |
| C12N 7/00 | (2006.01) |
| C12N 15/86 | (2006.01) |

(52) U.S. Cl.
CPC ...... *C12N 15/635* (2013.01); *C07K 14/70567* (2013.01); *C07K 14/721* (2013.01); *C12N 7/00* (2013.01); *C12N 15/86* (2013.01); *C12P 21/02* (2013.01); *C12N 2710/10043* (2013.01)

(58) Field of Classification Search
CPC combination set(s) only.
See application file for complete search history.

(56) References Cited

U.S. PATENT DOCUMENTS

| | | |
|---|---|---|
| 4,631,211 A | 12/1986 | Houghten |
| 4,859,609 A | 8/1989 | Dull et al. |
| 4,954,655 A | 9/1990 | Kelly |
| 4,981,784 A | 1/1991 | Evans et al. |
| 4,985,461 A | 1/1991 | Hsu et al. |
| 5,010,175 A | 4/1991 | Rutter et al. |
| 5,071,773 A | 12/1991 | Evans et al. |
| 5,117,057 A | 5/1992 | Hsu et al. |
| 5,171,671 A | 12/1992 | Evans et al. |
| 5,225,443 A | 7/1993 | Murphy et al. |
| 5,283,173 A | 2/1994 | Fields et al. |
| 5,378,726 A | 1/1995 | Yanagi et al. |
| 5,424,333 A | 6/1995 | Wing |
| 5,429,952 A | 7/1995 | Garner et al. |
| 5,459,127 A | 10/1995 | Felgner et al. |
| 5,514,578 A | 5/1996 | Hogness et al. |
| 5,530,021 A | 6/1996 | Yanagi et al. |
| 5,530,028 A | 6/1996 | Lidert et al. |
| 5,599,904 A | 2/1997 | Evans et al. |
| 5,639,616 A | 6/1997 | Liao et al. |
| 5,641,652 A | 6/1997 | Oro et al. |
| 5,668,175 A | 9/1997 | Evans et al. |
| 5,688,691 A | 11/1997 | Oro et al. |
| 5,710,004 A | 1/1998 | Evans et al. |
| 5,723,329 A | 3/1998 | Mangelsdorf et al. |
| 5,880,333 A | 3/1999 | Goff et al. |
| 5,919,667 A | 7/1999 | Gage et al. |
| 5,939,442 A | 8/1999 | Evans et al. |
| 5,989,863 A | 11/1999 | Tang et al. |
| 6,013,836 A | 1/2000 | Hsu et al. |

(Continued)

FOREIGN PATENT DOCUMENTS

| | | |
|---|---|---|
| CN | 1313276 | 9/2001 |
| EP | 234994 A1 | 1/1987 |

(Continued)

OTHER PUBLICATIONS

Guo, X., et al., "Isolation of two functional retinoid X receptor subtypes from the Ixodid tick, *Amblyomma americanum* (L.)," *Molecular and Cellular Endocrinology* 139:45-60, Elsevier Science Ireland Ltd., Ireland (1998).

(Continued)

*Primary Examiner* — Catherine S Hibbert

(74) *Attorney, Agent, or Firm* — Sterne, Kessler, Goldstein & Fox P.L.L.C.

(57) ABSTRACT

This invention relates to the field of biotechnology or genetic engineering. Specifically, this invention relates to the field of gene expression. More specifically, this invention relates to novel substitution mutant receptors and their use in a Group H nuclear receptor-based inducible gene expression system and methods of modulating the expression of a gene in a host cell for applications such as gene therapy, large scale production of proteins and antibodies, cell-based high throughput screening assays, functional genomics and regulation of traits in transgenic organisms.

21 Claims, 3 Drawing Sheets

Specification includes a Sequence Listing.

(56) References Cited

U.S. PATENT DOCUMENTS

| | | |
|---|---|---|
| 6,025,483 A | 2/2000 | Yanofsky |
| 6,096,787 A | 8/2000 | Evans et al. |
| 6,117,639 A | 9/2000 | Germann et al. |
| 6,147,282 A | 11/2000 | Goff et al. |
| 6,214,620 B1 | 4/2001 | Johns et al. |
| 6,245,531 B1 | 6/2001 | Hogness et al. |
| 6,258,603 B1 | 7/2001 | Carlson et al. |
| 6,265,173 B1 | 7/2001 | Evans et al. |
| 6,281,330 B1 | 8/2001 | Evans et al. |
| 6,300,488 B1 | 10/2001 | Gage et al. |
| 6,326,166 B1 | 12/2001 | Pomerantz et al. |
| 6,333,318 B1 | 12/2001 | Evans et al. |
| 6,379,945 B1 | 4/2002 | Jepson et al. |
| 6,410,245 B1 | 6/2002 | Northrop et al. |
| 6,458,926 B1 | 10/2002 | Evans et al. |
| 6,504,082 B1 | 1/2003 | Albertsen et al. |
| 6,635,429 B1 | 10/2003 | Leid et al. |
| 6,723,531 B2 | 4/2004 | Evans et al. |
| 6,756,491 B2 | 6/2004 | Evans et al. |
| 6,875,569 B2 | 4/2005 | Gage et al. |
| 6,939,711 B2 | 9/2005 | Goff et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 | 8/2006 | Palli et al. |
| 7,119,077 B1 | 10/2006 | Evans et al. |
| 7,183,061 B2 | 2/2007 | Jepson et al. |
| 7,456,315 B2 | 11/2008 | Hormann et al. |
| 7,531,326 B2 | 5/2009 | Kapitskaya et al. |
| 7,776,587 B2 | 8/2010 | Palli et al. |
| 7,807,417 B2 | 10/2010 | Palli et al. |
| 7,935,510 B2 | 5/2011 | Palli et al. |
| 8,021,878 B2 | 9/2011 | Palli et al. |
| 8,076,454 B2 | 12/2011 | Palli et al. |
| 8,105,825 B2 | 1/2012 | Dhadialla et al. |
| 8,115,059 B1 | 2/2012 | Palli et al. |
| 8,168,426 B2 | 5/2012 | Dhadialla et al. |
| 8,202,718 B2 | 6/2012 | Palli et al. |
| 8,236,556 B2 | 8/2012 | Kapitskaya et al. |
| 8,691,527 B2 * | 4/2014 | Palli .................. C07K 14/70567 435/320.1 |
| 8,715,959 B2 | 5/2014 | Palli et al. |
| 9,322,026 B2 | 4/2016 | Palli et al. |
| 2002/0110861 A1 | 8/2002 | Dhadialla et al. |
| 2002/0119521 A1 | 8/2002 | Palli et al. |
| 2004/0033600 A1 | 2/2004 | Palli et al. |
| 2004/0096942 A1 | 5/2004 | Palli et al. |
| 2004/0197861 A1 | 10/2004 | Palli et al. |
| 2004/0235097 A1 | 11/2004 | Zhang et al. |
| 2005/0266457 A1 | 12/2005 | Palli et al. |
| 2006/0100416 A1 | 5/2006 | Palli et al. |
| 2007/0161086 A1 | 7/2007 | Palli et al. |
| 2007/0300313 A1 | 12/2007 | Palli et al. |
| 2008/0064097 A1 | 3/2008 | Palli et al. |
| 2008/0115237 A1 | 5/2008 | Palli et al. |
| 2008/0145935 A1 | 6/2008 | Palli et al. |
| 2008/0176280 A1 | 7/2008 | Kapitskaya et al. |
| 2008/0216184 A1 | 9/2008 | Palli et al. |
| 2008/0235816 A1 | 9/2008 | Dhadialla et al. |
| 2008/0263687 A1 | 10/2008 | Kapitskaya et al. |
| 2008/0301825 A1 | 12/2008 | Palli et al. |
| 2010/0275281 A1 | 10/2010 | Dhadialla et al. |
| 2011/0059525 A1 | 3/2011 | Palli et al. |
| 2011/0059530 A1 | 3/2011 | Palli et al. |
| 2011/0212528 A1 | 9/2011 | Palli et al. |
| 2012/0167239 A1 | 6/2012 | Palli et al. |
| 2012/0185954 A1 | 7/2012 | Palli et al. |
| 2012/0322148 A1 | 12/2012 | Palli et al. |
| 2013/0232588 A1 | 9/2013 | Kapitskaya et al. |
| 2013/0244330 A1 | 9/2013 | Palli et al. |
| 2013/0267023 A1 | 10/2013 | Dhadialla et al. |
| 2013/0286156 A1 | 10/2013 | Dhadialla et al. |

FOREIGN PATENT DOCUMENTS

| | | |
|---|---|---|
| EP | 234994 A1 | 1/1987 |
| EP | 461809 A1 | 6/1991 |
| EP | 798378 A2 | 3/1997 |
| EP | 798378 B1 | 3/1997 |
| EP | 965644 A2 | 6/1999 |
| EP | 965644 A2 | 6/1999 |
| EP | 1266015 B1 | 3/2001 |
| WO | WO1989012690 A1 | 6/1989 |
| WO | WO1992000252 A1 | 6/1991 |
| WO | WO1994028028 A1 | 5/1994 |
| WO | WO1995018863 A1 | 1/1995 |
| WO | WO1995021931 A1 | 1/1995 |
| WO | WO 95/13373 A1 | 5/1995 |
| WO | WO1996017823 A1 | 12/1995 |
| WO | WO 96/05300 A2 | 2/1996 |
| WO | WO1996025508 A1 | 2/1996 |
| WO | WO1996037609 A1 | 5/1996 |
| WO | WO 96/21677 A1 | 7/1996 |
| WO | 9627673 A1 | 9/1996 |
| WO | WO1997035985 A1 | 3/1997 |
| WO | WO1997038117 A1 | 3/1997 |
| WO | WO1998033162 A1 | 1/1998 |
| WO | WO1999002683 A1 | 7/1998 |
| WO | WO 98/35550 A2 | 8/1998 |
| WO | WO1999010510 A2 | 8/1998 |
| WO | WO1999010510 A3 | 8/1998 |
| WO | WO1999027365 A1 | 11/1998 |
| WO | WO1999036520 A1 | 1/1999 |
| WO | WO1999036520 A1 | 1/1999 |
| WO | WO1999051777 A2 | 4/1999 |
| WO | WO1999051777 A3 | 4/1999 |
| WO | WO 99/26966 A2 | 6/1999 |
| WO | WO 99/36250 A1 | 7/1999 |
| WO | 9958155 A1 | 11/1999 |
| WO | 0071743 | 11/2000 |
| WO | WO2004005478 A2 | 1/2001 |
| WO | WO2001070816 A2 | 3/2001 |
| WO | 0136447 | 5/2001 |
| WO | 162780 | 8/2001 |
| WO | WO2002029075 A2 | 9/2001 |
| WO | WO2002066612 A2 | 2/2002 |
| WO | WO2002066613 A2 | 2/2002 |
| WO | WO2002066614 A2 | 2/2002 |
| WO | WO2002066615 A2 | 2/2002 |
| WO | WO2003105849 A1 | 6/2003 |
| WO | WO2004072254 A2 | 2/2004 |
| WO | WO2004078924 A2 | 2/2004 |
| WO | WO2005017126 A2 | 2/2004 |
| WO | WO2006083253 A1 | 2/2005 |
| WO | WO2005108617 A2 | 5/2005 |

OTHER PUBLICATIONS

Martinez A et al., "Transcriptional activation of the cloned Heliothis virescens (Lepidoptera) ecdysone receptor (HvEcR) by MuristeroneA", Insect Biochem Mol Biol, 1999, 29:915-930.

Egea PF et al. "Effects of ligand binding on the association properties and conformation in solution of retinoic acid receptors RXR and RAR." Mol Endocrinol. May 2002;16(5):987-97.

Shea C et al., "An rxr/usp homolog from the parasitic nematode, Dirofilaria immitis." Gene. Jan. 7, 2004;324:171-82.

Bonneton F; et al. "Rapid divergence of the ecdysone receptor in Diptera and Lepidoptera suggests coevolution between ECR and USP-RXR." Mol Biol Evol. Apr. 2003;20(4):541-53.

Hayward DC; et al. "The structure of the USP/RXR of Xenos pecki indicates that Strepsiptera are not closely related to Diptera." Dev Genes Evol. Apr. 2005;215(4):213-9.

Moradpour D et al. "Independent regulation of two separate gene activities in a continuous human cell line." Biol Chem. Aug.-Sep. 1998;379(8-9):1189-91.

Hoppe UC et al. "Adenovirus-mediated Inducible Gene Expression in Vivo by Hybrid Ecdysone Receptor." Mol Therapy 2000 1(2):159-164.

(56) References Cited

OTHER PUBLICATIONS

Antoniewski C et al., The ecdysone response enhancer of the Fbp1 gene of *Drosophila melanogaster* is a direct target for the EcR/USP nuclear receptor, Mol Cell Biol, (1994), 14:4465-74.

Ashburner M et al., Temporal control of puffing activity in polytene chromosomes, Cold Spring Harb Symp Quant Biol, (1974), 38:655-62.

Cherbas L et al., Identification of ecdysone response elements by analysis of the *Drosophila* Eip28/29 gene, Genes Dev, (1991), 5:120-31.

Cho WL et al., Mosquito ecdysteroid receptor: analysis of the cDNA and expression during vitellogenesis, Insect Biochem Mol Biol, (1995), 25:19-27.

Chung AC et al., Cloning of crustacean ecdysteroid receptor and retinoid-X receptor gene homologs and elevation of retinoid-X receptor mRNA by retinoic acid, Mol Cell Endocrinol, (1998), 139:209-27.

D'Avino PP et al., The moulting hormone ecdysone is able to recognize target elements composed of direct repeats, Mol Cell Endocrinol, (1995), 113:1-9.

Dhadialla TS et al., New insecticides with ecdysteroidal and juvenile hormone activity, Annu Rev Entomol, (1998), 43:545-69.

Evans RM, The steroid and thyroid hormone receptor superfamily, Science, (1988), 240:889-95.

Fujiwara H et al., Cloning of an ecdysone receptor homolog from Manduca sexta and the developmental profile of its mRNA in wings, Insect Biochem Mol Biol, (1995), 25:845-56.

Godowski PJ et al., Signal transduction and transcriptional regulation by glucocorticoid receptor-LexA fusion proteins, Science, (1988), 241:812-6.

Guo X et al., Isolation of a functional ecdysteroid receptor homologue from the ixodid tick *Amblyomma americanum* (L.), Insect Biochem Mol Biol, (1997), 27:945-62.

Hannan GN et al., Cloning and characterization of LcEcR: a functional ecdysone receptor from the sheep blowfly *Lucilia cuprina*, Insect Biochem Mol Biol, (1997), 27:479-88.

Heberlein U et al., Characterization of *Drosophila* transcription factors that activate the tandem promoters of the alcohol dehydrogenase gene, Cell, (1985), 41:965-77.

Imhof MO et al., Cloning of a *Chironomus tentans* cDNA encoding a protein (cEcRH) homologous to the *Drosophila melanogaster* ecdysteroid receptor (dEcR), Insect Biochem Mol Biol, (1993), 23:115-24.

Kothapalli R et al., Cloning and developmental expression of the ecdysone receptor gene from the spruce budworm, *Choristoneura fumiferana*, Dev Genet, (1995), 17:319-30.

Licitra EJ et al., A three-hybrid system for detecting small ligand-protein receptor interactions, Proc Natl Acad Sci U S A, (1996), 93:12817-21.

Martinez A et al., Transcriptional activation of the cloned Heliothis virescens (Lepidoptera) ecdysone receptor (HvEcR) by muristerone A, Insect Biochem Mol Biol, (1999), 29:915-30.

Morrison DA et al., Isolation of transformation-deficient *Streptococcus* pneumoniae mutants defective in control of competence, using insertion-duplication mutagenesis with the erythromycin resistance determinant of pAM beta 1, J Bacteriol, (1984), 159:870-6.

Mouillet JF et al., Cloning of two putative ecdysteroid receptor isoforms from Tenebrio molitor and their developmental expression in the epidermis during metamorphosis, Eur J Biochem, (1997), 248:856-63.

Neuberger MS et al., Recombinant antibodies possessing novel effector functions, Nature, (1984), 312:604-8.

Riddiford LM et al., Ecdysone receptors and their biological actions, Vitam Horm, (2000), 60:1-73.

Saleh DS et al., Cloning and characterization of an ecdysone receptor cDNA from Locusta migratoria, Mol Cell Endocrinol, (1998), 143:91-9.

Srini C. Perera Mspjkartsdsrp, An analysis of ecdysone receptor domains required for heterodimerization with ultraspiracle, Archives of Insect Biochemistry and Physiology, (1999), 41:61-70.

Suhr ST et al., High level transactivation by a modified Bombyx ecdysone receptor in mammalian cells without exogenous retinoid X receptor, Proc Natl Acad Sci U S A, (1998), 95:7999-8004.

Swevers L et al., The silkmoth homolog of the *Drosophila* ecdysone receptor (B1 isoform): cloning and analysis of expression during follicular cell differentiation, Insect Biochem Mol Biol, (1995), 25:857-66.

Verras M et al., Cloning and characterization of CoEcR. An ecdysone receptor homolog from the mediterranean fruit fly ceratitis capitata, Eur J Biochem, (1999), 265:798-808.

Wilson JM et al., Hepatocyte-directed gene transfer in vivo leads to transient improvement of hypercholesterolemia in low density lipoprotein receptor-deficient rabbits, J Blol Chem, (1992), 267:963-7.

Yao TP et al., *Drosophila* ultraspiracle modulates ecdysone receptor function via heterodimer formation, Cell, (1992), 171:63-72.

Yao TP et al., Functional ecdysone receptor is the product of EcR and Ultraspiracle genes, Nature, (1993), 366:476-9.

Christopherson KS et al., Eodysteroid-dependent regulation of genes in mammalian cells by a *Drosophila* ecdysone receptor and chimeric transactivators, Proc Natl Acad Sci U S A, (1992), 89:6314-8.

Kakizawa T et al., Ligand-dependent heterodimerization of thyroid hormone receptor and retinoid X receptor, J Biol Chem, (1997), 272:23799-804.

Koelle MR et al., The *Drosophila* EcR gene encodes en ecdysone receptor, a new member of the steroid receptor superfamily, Cell, (1991), 67:59-77.

Leid M et al., Purification, cloning, and RXR identity of the HeLa cell factor with which RAR or TR heterodimerizes to bind target sequences efficiently, Cell, (1992), 68:377-95.

Leonhardt SA et al., Agonist and antagonists induce homodimerization and mixed ligand heterodimerization of human progesterone receptors in vivo by a mammalian two-hybrid assay, Mol Endocrinol, (1998), 12:1914-30.

Metzger D et al., The human oestrogen receptor functions in yeast, Nature, (1988), 334:31-6.

No D et al., Ecdysone-inducible gene expression in mammalian cells and transgenic mice, Proc Natl Acad Sci U S A, (1996), 93:3346-51.

Perera SC et al., Studies on two ecdysone receptor isoforms of the spruce budworm, *Choristoneura fumiferana*, Mol Cell Endocrinol, (1999), 152:73-84.

Andrianov VG et al., 4-Aminofurazan-3-hydroximic halides, Chemistry of Heterocyclic Compounds, (1992), 28:581-585.

Andrianov VG et al., 4-Amino-2-1,2,4-oxadiazolines, Chemistry of Heterocyclic Compounds, (1991), 27:216-218.

Belshaw PJ et al., Controlling protein association and subcellular localization with a synthetic ligand that induces heterodimerization of proteins, Proc Natl Acad Sci U S A, (1996), 93:4604-7.

Belshaw PJ et al., Rational Design of Orthogonal Receptor-Ligand Combinations, Angewandte Chemie International Edition in English, (1995), 34:2129-2132.

Brennan JD, Preparation and Entrapment of Fluorescently Labeled Proteins for the Development of Reagentless Optical Biosensor, Journal of Fluorescence, (1999), 9:295-312.

Cao S et al., N'-tert-Butyl-N'-aroyl-N-(alkoxycarbonylmethyl)-N-aroylhydrazines, a novel nonsteroidal ecdysone agonist: synthesis, insecticidal activity, conformational, and crystal structure analysis Canadian Journal of Chemistry, (2001), 79:272-278.

Cao S et al., N'-tert-butyl-N'-aroyl-N-(alkoxycarbonylmethyl)-N-aroylhydrazines, a novel nonsteroidal ecdysone agonist: syntheses, insecticidal activity, conformational, and crystal structure analysis, Canadian Journal of Chemistry, (2001), 79:272-278.

Carlson GR et al., The chemical and biological properties of methoxyfenozide, a new insecticidal ecdysteroid agonist, Pest Management Science, (2001), 57:115-119.

Doyle DF et al., Engineering orthogonal ligand-receptor pairs from "near drugs", J Am Chem Soc, (2001), 123:11367-71.

Fields S et al., A novel genetic system to detect protein-protein interactions, Nature, (1989), 340:245-6.

Filmus J et al., Synergistic induction of promoters containing metal- and glucocorticoid-responsive elements, Nucleic Acids Res, (1992), 20:2755-60.

(56) References Cited

OTHER PUBLICATIONS

Glass CK et al., Nuclear receptor coactivators, Curr Opin Cell Biol, (1997), 9:222-32.
Holt JR et al., Functional expression of exogenous proteins in mammalian sensory hair cells infected with adenoviral vectors, J Neurophysiol, (1999), 81:1881-8.
Horwitz KB et al., Nuclear receptor coactivators and corepressors, Mol Endocrinol, (1996), 10:1167-77.
Kim JS et al., Design of TATA box-binding protein/zinc finger fusions for targeted regulation of gene expression, Proc Nati Acad Sci U S A, (1997), 94:3616-20.
Kirken RA et al., Two discrete regions of interleukin-2 (IL2) receptor beta independently mediate IL2 activation of a PD98059/rapamycin/wortmannin-insensitive Stat5a/b serine kinase, J Biol Chem, (1997), 272:15459-65.
Nakagawa Y et al., Quantitative structure-activity studies of insect growth regulators: XIX: Effects of substituents on the aromatic moiety of dibenzoylhydrazines on larvicidal activity against the beet armyworm *Spodoptera exigua*, , Pest Management Science, (2002), 58:131-138.
O'Brien RM et al., Structural and functional analysis of the human phosphoenolpyruvate carboxykinase gene promoter, Biochim Biophys Acta, (1995), 1264:284-8.
Peet DJ et al., Engineering novel specificities for ligand-activated transcription in the nuclear hormone receptor RXR, Chem Biol, (1998), 5:13-21.
Pierce AC et al., Computational Binding Studies of Orthogonal Cyclosporin-Cyclophilin Pairs, Angewandte Chemie International Edition in English, (1997), 36:1466-69.
Spencer DM et al., Controlling signal transduction with synthetic ligands, Science, (1993), 262:1019-24.
Trisyono A et al., Effect of the nonsteroidal ecdysone agonists, methoxyfenozide and tebufenozide, on the European Corn Borer (Lepidoptera: Pyralidae), J Economic Entomology, (1997), 90:1486-1492.
Wing KD, RH 5849, a nonsteroidal ecdysone agonist: effects on a *Drosophila* cell line, Science, (1988), 241:467-9.
Wipf P et al., Combinatorial synthesis and biological evaluation of library of small-molecule Ser/Thr-protein phosphatase inhibitors, Bioorg Med Chem, (1997), 5:165-77.
Wurm FM et al., Inducible overproduction of the mouse c-myc protein in mammalian cells, Proc Natl Acad Sci U S A, (1986), 83:5414-8.
Zhang X et al., Study on synthesis and bioactivity of new diacylhydrazine IGR JS118, Nongyao, (2003), 42:18-20.
Office Action dated Jun. 13, 2005 in U.S. Appl. No. 09/965,703, inventors Palli, et al., filed Sep. 26, 2001.
Office Action dated Nov. 24, 2004 in U.S. Appl. No. 09/965,703, inventors Palli, et al., filed Sep. 26, 2001.
Office Action dated May 14, 2004 in U.S. Appl. No. 09/965,703, inventors Palli, et al., filed Sep. 26, 2001.
Office Action dated Dec. 9, 2008 in U.S. Appl. No. 09/965,697, inventors Dhadialla, et al., filed Sep. 27, 2001.
Office Action dated May 28, 2008 in U.S. Appl. No. 09/965,697, inventors Dhadialla, et al., filed Sep. 27, 2001.
Office Action dated Aug. 9, 2007 in U.S. Appl. No. 09/965,697, inventors Dhadialla, et al., filed Sep. 27, 2001.
Office Action dated Nov. 13, 2006 in U.S. Appl. No. 09/965,697, inventors Dhadialla, et al., filed Sep. 27, 2001.
Office Action dated Apr. 18, 2006 in U.S. Appl. No. 09/965,697, inventors Dhadialla, et al., filed Sep. 27, 2001.
Office Action dated Jul. 12, 2005 in U.S. Appl. No. 09/965,697, inventors Dhadialla, et al., filed Sep. 27, 2001.
Office action dated Aug. 22, 2006 in U.S. Appl. No. 10/239,134, inventors Palli et al., filed Sep. 19, 2002.
Office Action dated Mar. 13, 2008 in U.S. Appl. No. 10/468,199, inventors Kapitskaya, et al., filed Dec. 17, 2003.
Office Action dated Jun. 11, 2007 in U.S. Appl. No. 10/468,199, inventors Kapitskaya, et al., filed Dec. 17, 2003.
Office Action dated Oct. 26, 2006 in U.S. Appl. No. 10/468,199, inventors Kapitskaya, et al., filed Dec. 17, 2003.
Office Action dated Sep. 7, 2007 in U.S. Appl. No. 11/118,855, inventors Palli, et al., filed Apr. 29, 2005.
Office Action delivered electronically Aug. 21, 2008 in U.S. Appl. No. 11/677,968, inventors Palli, et al., filed Feb. 22, 2007.
Office Action dated Feb. 20, 2009 in U.S. Appl. No. 11/677,968, inventors Palli et al., filed Feb. 22, 2007.
U.S. Appl. No. 09/965,697, inventors Dhadialla, et al., filed Sep. 27, 2001, published as US 2002/0110861 A1.
U.S. Appl. No. 10/468,192, inventors Palli, et al., filed Aug. 15, 2003, published as US2011/0212528 A1.
U.S. Appl. No. 10/468,200, inventors Palli, et al., filed Aug. 15, 2003, published as US 2012/0167239 A1.
U.S. Appl. No. 10/468,193, inventors Palli, et al., filed Dec. 17, 2003, published as US 2006/0100416 A1.
U.S. Appl. No. 10/468,199, inventors Kapitskaya, et al., filed Dec. 17, 2003, published as US 2004/0096942 A1.
U.S. Appl. No. 11/118,855, inventors Palli, et al., filed Apr. 28, 2005, published as US 2005/0266457 A1.
U.S. Appl. No. 11/677,968, inventors Palli, et al., filed Feb. 22, 2007, published as US 2007/0161086 A1.
U.S. Appl. No. 11/841,325, inventors Dhadialla, et al., filed Aug. 20, 2007, published as US 2008/0235816 A1.
U.S. Appl. No. 11/841,464, inventors Palli, et al., filed Aug. 20, 2007, published as US 2008/0145935 A1.
U.S. Appl. No. 11/841,495, inventors Palli, et al., filed Aug. 20, 2007, published as 2008/0115237 A1.
U.S. Appl. No. 11/841,529, inventors Palli, et al., filed Aug. 20, 2007, published as US 2007/0300313 A1.
U.S. Appl. No. 11/841,597, inventors Kapitskaya, et al., filed Aug. 20, 2007, published as US 2008/0176280 A1.
U.S. Appl. No. 11/841,631, inventors Palli, et al., filed Aug. 20, 2007, published as US 2008/0216184 A1.
U.S. Appl. No. 11/841,644, inventors Palli, et al., filed Aug. 20, 2007, published as US 2008/0301825 A1.
U.S. Appl. No. 11/841,648, inventors Kapitskava, et al., filed Aug. 24, 2007, published as US 2008/0263687 A1.
Hayward, D.C., et al., "The sequence of locust RXR, homologous to *Drosophila* Ultraspiracle, and its evolutionary implications," Development Genes and Evolution 209: 564-571, Springer Berlin/Heidelberg (1999).
Helmreich E.J.M., "The Biochemistry of Cell Signalling," p. 192, Oxford University Press (2001).
Hofmann, A. et al., "Rapid retroviral delivery of tetracycline-inducible genes in a single autoregulatory cassette," Proc. Natl. Acad. Sci. USA 93: 5185-5910, National Academy of Sciences (1996).
Martinez, A., et al., "Creation of ecdysone receptor chimeras in plants for controlled regulation of gene expression," Mol Gen Genet 261:546-552, Springer-Verlag (1999).
Perera, S.C. et al., "An Analysis of Ecdysone Receptor Domains Required for Heterodimerization With Ultraspiracle," Archives of Insect Biochemistry and Physiology 41: 61-70, Wiley-Liss, Inc. (1999).
Shimizu, B-i. et al., "Molting hormonal and larvicidal activities of aliphatic acyl analogs of dibenzoylhydrazine insecticides," Steroids 62:638-642, Elsevier Science Inc. (1997).
Talbot, W.S., et al., "*Drosophila* Tissues with Different Metamorphic Responses to Ecdysone Express Different Ecdysone Receptor Isoforms," Cell 73:1323-1337, Cell Press (1993).
UniProtKB/Swiss-Protein Database, Accession No. P49880, "Ecdysone receptor," 2 pages (1996).
UniProtKB/Swiss-Protein Database, Accession No. P49883, "Ecdysone receptor," 2 pages (1996).
Examiner's Score Search Results for U.S. Appl. No. 11/118,855, inventors Palli et al., 27 pages (conducted on Aug. 14, 2007).
Examiner's Score Search Results for U.S. Appl. No. 11/118,855, inventors Palli et al., 17 pages (conducted on Aug. 14, 2007.
Blumberg, B., et al., "Multiple retinoid-responsive receptors in a single cell: Families of retinoid "X" receptors and retinoic acid receptors in the Xenopous egg," Proc. Natl. Acad. Sci. USA 89:2321-2325, National Academy of Sciences, United States (1992).

(56) References Cited

OTHER PUBLICATIONS

Clayton, G.M., et al., "The structure of the ultraspiracle ligand-binding domain reveals a nuclear receptor locked in an inactive conformation," *Proc. Natl. Acad. Sci.* 98:1549-1554, National Academy of Sciences, United States (2001).
Laudet, V., et al., "A Unified Nomenclature System for the Nuclear Receptor Superfamily," *Cell* 97:161-163, Cell Press, United States (1999).
Mangelsdorf, D.J., et al., "Nuclear receptor that identifies a novel retinoic acid response pathway," *Nature* 345:224-229, Nature Publishing Group, England (1990).
Marklew, S., et al., "Isolation of a novel RXR from Xenopus that most closely resembles mammalian RXRβ and is expressed throughout early development," *Biochim Biophys Acta* 1218:267-272, Elsevier Science B.V., Netherlands (1994).
Palmer, M.J., et al., "Characterization of EcR and RXR Homologous in the Ixodid Tick, *Amblyomma amerianum* (L.)," *Am. Zool.* 39:747-757, American Society of Zoologists, United States (1999).
EMBL Nucleotide Sequence Database, Accession No. AJ251542, 7 pages (Entry date 2000).
UniProtKB/Swiss-Protein Database, Accession No. O02035, "Ecdysone receptor," 4 pages (1996).
UniProtKB/Swiss-Protein Database, Accession No. O76246, "Ecdysteroid receptor," 4 pages (1996).
Office action dated Jun. 30, 2009 in U.S. Appl. No. 11/118,855, inventors Palli et al., filed Apr. 29, 2005.
Office Action dated Feb. 25, 2009 in U.S. Appl. No. 11/841,325, inventors Dhadialla et al., filed Aug. 20, 2007.
Office Action dated Feb. 24, 2009 in U.S. Appl. No. 11/841,495, inventors Palli et al., filed Aug. 20, 2007.
Office Action dated Apr. 2, 2009 in U.S. Appl. No. 11/841,529, inventors Palli et al., filed Aug. 20, 2007.
Office Action dated Jun. 29, 2009 in U.S. Appl. No. 11/841,648, inventors Kapitskaya et al., filed Aug. 24, 2007.
Office Action dated Jun. 23, 2009 in U.S. Appl. No. 09/965,697, inventors Dhadialla et al., filed Sep. 27, 2001.
Office Action dated May 22, 2009, in U.S. Appl. No. 11/837,834, inventors Palli et al., filed Aug. 13, 2007.
U.S. Appl. No. 11/837,834, Inventors Palli et al., filed Aug. 13, 2007, published as US 2008/0064097 A1.
Notice of Allowance dated Feb. 4, 2010 in U.S. Appl. No. 11/118,855, inventors Palli et al., filed Apr. 29, 2005.
Office Action dated Apr. 20, 2010 in U.S. Appl. No. 11/841,597, inventors Kapitskaya et al., filed Aug. 20, 2007.
Office action dated Mar. 22, 2010 in U.S. Appl. No. 11/841,648, inventors Kapitskaya et al., filed Aug. 24 ,2007.
Notice of Allowance dated Mar. 19, 2010 in U.S. Appl. No. 11/841,495, inventors Palli et al., filed Aug. 20, 2007.
Office Action dated Apr. 1, 2010 in U.S. Appl. No. 11/841,529, inventors Palli et al., filed Aug. 20, 2007.
Office action dated Feb. 22, 2010 in U.S. Appl. No. 11/837,834, inventors Palli et al., filed Aug. 13, 2007.
Office Action dated Sep. 28, 2010 in U.S. Appl. No. 11/841,631, inventors Palli et al., filed Aug. 20, 2007.
Office Action dated May 12, 2010 in U.S. Appl. No. 11/841,464, inventors Palli et al., filed Aug. 20, 2007.
Notice of Allowance dated May 24, 2010 in U.S. Appl. No. 11/677,968, inventors Palli et al., filed Feb. 22, 2007.
Office Action dated Sep. 14, 2010 in U.S. Appl. No. 11/841,644, inventors Palli et al., filed Aug. 20, 2007.
Office Action dated Nov. 10, 2010 in U.S. Appl. No. 11/841,597, inventors Kapitskaya et al., filed Aug. 20, 2007.
Office Action dated May 25, 2010 in U.S. Appl. No. 09/965,697, inventors Dhadialla et al., filed Sep. 27, 2001.
Kumar, M.B., "A single point mutation in ecdysone receptor leads to increased ligand specificity: Implications for gene switch applications," *Proc. Natl. Acad. Sci.* 99: 14710-14715, National Academy of Sciences, United States (2002).
Palli, S.R. et al., "Improved ecdysone receptor-based inducible gene regulation system," *Eur. J. Biochem.* 270:1308-1315, Wiley Interscience (2003).
Tran, H.T. et al., "Reconstruction of Ligand-Dependent Transactivation of *Choristoneura fumiferana* Ecdysone Receptor in Yeast," *Molecular Endocrinology* 15: 1140-1153, The Endocrine Society (2001).
U.S. Appl. No. 12/707,599, Inventors Dhadialla et al., filed Feb. 17, 2010, issued as U.S. Pat. No. 8,168,426 B2.
U.S. Appl. No. 12/818,034, filed Jun. 17, 2010, inventors Palli et al., issued as U.S. Pat. No. 8,202,718.
U.S. Appl. No. 12/859,940, filed Aug. 20,2010, inventors Palli et al., published as US 2011/0059530 A1.
Reinhardy, R.K. et al., EMBL Accession No. AJ251810, XP-002405910, "Bicyclus anynana ecdysone receptor fragment," 2 pages (1999).
Teboul, M. et al., "OR-1, a member of the nuclear receptor superfamily that interacts with the 9-cis-retinoic acid receptor," *Proc. Natl. Acad. Sci. USA* 92; 2096-2100, National Academy of Sciences, Washington, D.C., U.S.A. (1995).
Notice of Allowance dated Apr. 27, 2011 in U.S. Appl. No. 11/841,631, filed Aug. 20, 2007, inventors Palli et al.
Notice of Allowance dated Dec. 27, 2010 in U.S. Appl. No. 11/118,855, filed Apr. 29, 2005, inventors Palli et al.
Office Action dated Feb. 15, 2011 in U.S. Appl. No. 09/965,697, inventors Dhadialla, et al., filed Sep. 27, 2001.
Office Action dated Mar. 30, 2011, in U.S. Appl. No. 12/818,034, filed Jun. 17, 2010, inventors Palli et al.
Office Action dated Dec. 7, 2010 in U.S. Appl. No. 11/841,648, filed Aug. 24, 2007, inventors Kapitskaya et al.
Office Action dated Aug. 9, 2011 in U.S. Appl. No. 11/841,648, filed Aug. 24, 2007, inventors Kapitskaya et al.
Office Action dated Oct. 18, 2011, in U.S. Appl. No. 12/818,034, filed Jun. 17, 2010, inventors Palli et al.
Notice of Allowance dated Dec. 30, 2010 in U.S. Appl. No. 12/707,599, inventors Dhadialla, et al., filed Feb. 17, 2010.
Notice of Allowance dated Jul. 20, 2011 in U.S. Appl. No. 12/707,599, inventors Dhadialla, et al., filed Feb. 17, 2010.
Notice of Allowance dated Sep. 21, 2011 in U.S. Appl. No. 09/965,697, inventors Dhadialla, et al., filed Sep. 27, 2001.
Office Action dated Sep. 19, 2007 in U.S. Appl. No. 10/468,193, inventors Palli, et al., filed Dec. 17, 2003.
Office Action dated Feb. 18, 2010 in U.S. Appl. No. 10/468,193, inventors Palli et al., filed Dec. 17, 2003.
Office Action dated Jun. 21, 2011 in U.S. Appl. No. 10/468,193, inventors Palli et al., filed Dec. 17, 2003.
Office Action dated May 10, 2012 in U.S. Appl. No. 10/468,193, inventors Palli et al., filed Dec. 17, 2003.
Office Action dated Nov. 29, 2012 in U.S. Appl. No. 10/468,193, inventors Palli et al., filed Dec. 17, 2003.
Office Action dated Jul. 23, 2013 in U.S. Appl. No. 10/468,193, inventors Palli, et al., filed on Dec. 17, 2003.
Office Action dated Feb. 14, 2012 in U.S. Appl. No. 11/841,644, inventors Palli et al., filed Aug. 20, 2007.
Office Action dated Jun. 5, 2013 in U.S. Appl. No. 11/841,644, inventors Palli et al., filed Aug. 20, 2007.
U.S. Appl. No. 13/615,348, inventors Palli et al., filed Sep. 13, 2012.
Imhof et al., Cloning of a *Chironomus tentans* cDNA encoding a protein (cECRH) homologous to the *Drosophila melanogaster* ecdysteroid receptor (dECR), *Insect Biochem. Molec. Biol.* 23: Abstract only (1993).
USPTO Score Result for Seq ID No. 1 for Imhof et al., Cloning of a *Chironomus tentans* cDNA encoding a protein (cECRH) homologous to the *Drosophila melanogaster* ecdysteroid receptor (dECR), *Insect Biochem. Molec. Biol.* 23.
Cho et al., "Mosquito Ecdysteorid Receptor: Analysis of the cDNA and Expression During Vitellogenesis," *Insect Biochem. Molec. Biol.* 25: 19-27 (1995).
USPTO Score Result for Cho et al., "Mosquito Ecdysteorid Receptor: Analysis of the cDNA and Expression During Vitellogenesis," *Insect Biochem. Molec. Biol.* 25: 19-27 (1995).
Wurtz et al., "A new model for 20-hydroxyecdysone and dibenzoylhdrazine binding: A homology modeling and docking approach," *Protein Science* 9: 1073-1084 (2000).

(56) References Cited

OTHER PUBLICATIONS

Notice of Allowance dated Oct. 21, 2013 in U.S. Appl. No. 11/841,529, inventors Palli et al.

\* cited by examiner

SEQUENCE LISTING

<160> NUMBER OF SEQ ID NOS: 119

<210> SEQ ID NO 1
<211> LENGTH: 240
<212> TYPE: PRT
<213> ORGANISM: Choristoneura fumiferana

<400> SEQUENCE: 1

| Leu | Thr | Ala | Asn | Gln | Gln | Phe | Leu | Ile | Ala | Arg | Leu | Ile | Trp | Tyr | Gln |
|---|---|---|---|---|---|---|---|---|---|---|---|---|---|---|---|
| 1 | | | | 5 | | | | | 10 | | | | | 15 | |
| Asp | Gly | Tyr | Glu | Gln | Pro | Ser | Asp | Glu | Asp | Leu | Lys | Arg | Ile | Thr | Gln |
| | | | 20 | | | | | 25 | | | | | 30 | | |
| Thr | Trp | Gln | Gln | Ala | Asp | Asp | Glu | Asn | Glu | Glu | Ser | Asp | Thr | Pro | Phe |
| | | | | 35 | | | | 40 | | | | | 45 | | |
| Arg | Gln | Ile | Thr | Glu | Met | Thr | Ile | Leu | Thr | Val | Gln | Leu | Ile | Val | Glu |
| | | | 50 | | | | | 55 | | | | | 60 | | |
| Phe | Ala | Lys | Gly | Leu | Pro | Gly | Phe | Ala | Lys | Ile | Ser | Gln | Pro | Asp | Gln |
| 65 | | | | | 70 | | | | | 75 | | | | | 80 |
| Ile | Thr | Leu | Leu | Lys | Ala | Cys | Ser | Ser | Glu | Val | Met | Met | Leu | Arg | Val |
| | | | | 85 | | | | | 90 | | | | | 95 | |
| Ala | Arg | Arg | Tyr | Asp | Ala | Ala | Ser | Asp | Ser | Val | Leu | Phe | Ala | Asn | Asn |
| | | | | 100 | | | | | 105 | | | | | 110 | |
| Gln | Ala | Tyr | Thr | Arg | Asp | Asn | Tyr | Arg | Lys | Ala | Gly | Met | Ala | Tyr | Val |
| | | | | 115 | | | | | 120 | | | | | 125 | |
| Ile | Glu | Asp | Leu | Leu | His | Phe | Cys | Arg | Cys | Met | Tyr | Ser | Met | Ala | Leu |
| | | 130 | | | | | 135 | | | | | 140 | | | |
| Asp | Asn | Ile | His | Tyr | Ala | Leu | Leu | Thr | Ala | Val | Val | Ile | Phe | Ser | Asp |
| 145 | | | | | 150 | | | | | 155 | | | | | 160 |
| Arg | Pro | Gly | Leu | Glu | Gln | Pro | Gln | Leu | Val | Glu | Ile | Gln | Arg | Tyr |
| | | | | 165 | | | | | 170 | | | | | 175 |
| Tyr | Leu | Asn | Thr | Leu | Arg | Ile | Tyr | Ile | Leu | Asn | Gln | Leu | Ser | Gly | Ser |
| | | | | 180 | | | | | 185 | | | | | 190 | |
| Ala | Arg | Ser | Ser | Val | Ile | Tyr | Gly | Lys | Ile | Leu | Ser | Ile | Leu | Ser | Glu |
| | | | 195 | | | | | 200 | | | | | 205 | | |
| Leu | Arg | Thr | Leu | Gly | Met | Gln | Asn | Ser | Asn | Met | Cys | Ile | Ser | Leu | Lys |
| | | 210 | | | | | 215 | | | | | 220 | | | |
| Leu | Lys | Asn | Arg | Lys | Leu | Pro | Pro | Phe | Leu | Glu | Glu | Ile | Trp | Asp | Val |
| 225 | | | | | 230 | | | | | 235 | | | | | 240 |

<210> SEQ ID NO 2
<211> LENGTH: 237
<212> TYPE: PRT
<213> ORGANISM: Drosophila melanogaster

<400> SEQUENCE: 2

| Leu | Thr | Tyr | Asn | Gln | Leu | Ala | Val | Ile | Tyr | Lys | Leu | Ile | Trp | Tyr | Gln |
|---|---|---|---|---|---|---|---|---|---|---|---|---|---|---|---|
| 1 | | | | 5 | | | | | 10 | | | | | 15 | |
| Asp | Gly | Tyr | Glu | Gln | Pro | Ser | Glu | Glu | Asp | Leu | Arg | Arg | Ile | Met | Ser |
| | | | 20 | | | | | 25 | | | | | 30 | | |
| Gln | Pro | Asp | Glu | Asn | Glu | Ser | Gln | Thr | Asp | Val | Ser | Phe | Arg | His | Ile |
| | | | | 35 | | | | 40 | | | | | 45 | | |
| Thr | Glu | Ile | Thr | Ile | Leu | Thr | Val | Gln | Leu | Ile | Val | Glu | Phe | Ala | Lys |
| | | | 50 | | | | | 55 | | | | | 60 | | |
| Gly | Leu | Pro | Ala | Phe | Thr | Lys | Ile | Pro | Gln | Glu | Asp | Gln | Ile | Thr | Leu |
| 65 | | | | | 70 | | | | | 75 | | | | | 80 |
| Leu | Lys | Ala | Cys | Ser | Ser | Glu | Val | Met | Met | Leu | Arg | Met | Ala | Arg | Arg |

```
                    85                  90                  95
Tyr Asp His Ser Ser Asp Ser Ile Phe Phe Ala Asn Asn Arg Ser Tyr
                100                 105                 110

Thr Arg Asp Ser Tyr Lys Met Ala Gly Met Ala Asp Asn Ile Glu Asp
                115                 120                 125

Leu Leu His Phe Cys Arg Gln Met Phe Ser Met Lys Val Asp Asn Val
    130                 135                 140

Glu Tyr Ala Leu Leu Thr Ala Ile Val Ile Phe Ser Asp Arg Pro Gly
145                 150                 155                 160

Leu Glu Lys Ala Gln Leu Val Glu Ala Ile Gln Ser Tyr Tyr Ile Asp
                165                 170                 175

Thr Leu Arg Ile Tyr Ile Leu Asn Arg His Cys Gly Asp Ser Met Ser
                180                 185                 190

Leu Val Phe Tyr Ala Lys Leu Leu Ser Ile Leu Thr Glu Leu Arg Thr
            195                 200                 205

Leu Gly Asn Gln Asn Ala Glu Met Cys Phe Ser Leu Lys Leu Lys Asn
        210                 215                 220

Arg Lys Leu Pro Lys Phe Leu Glu Glu Ile Trp Asp Val
225                 230                 235

<210> SEQ ID NO 3
<211> LENGTH: 240
<212> TYPE: PRT
<213> ORGANISM: Amblyomma americanum

<400> SEQUENCE: 3

Pro Gly Val Lys Pro Leu Ser Ser Ser Gln Glu Asp Leu Ile Asn Lys
1               5                   10                  15

Leu Val Tyr Tyr Gln Gln Glu Phe Glu Ser Pro Ser Glu Glu Asp Met
                20                  25                  30

Lys Lys Thr Thr Pro Phe Pro Leu Gly Asp Ser Glu Glu Asp Asn Gln
            35                  40                  45

Arg Arg Phe Gln His Ile Thr Glu Ile Thr Ile Leu Thr Val Gln Leu
50                  55                  60

Ile Val Glu Phe Ser Lys Arg Val Pro Gly Phe Asp Thr Leu Ala Arg
65                  70                  75                  80

Glu Asp Gln Ile Thr Leu Leu Lys Ala Cys Ser Ser Glu Val Met Met
                85                  90                  95

Leu Arg Gly Ala Arg Lys Tyr Asp Val Lys Thr Asp Ser Ile Val Phe
                100                 105                 110

Ala Asn Asn Gln Pro Tyr Thr Arg Asp Asn Tyr Arg Ser Ala Ser Val
            115                 120                 125

Gly Asp Ser Ala Asp Ala Leu Phe Arg Phe Cys Arg Lys Met Cys Gln
    130                 135                 140

Leu Arg Val Asp Asn Ala Glu Tyr Ala Leu Leu Thr Ala Ile Val Ile
145                 150                 155                 160

Phe Ser Glu Arg Pro Ser Leu Val Asp Pro His Lys Val Glu Arg Ile
                165                 170                 175

Gln Glu Tyr Tyr Ile Glu Thr Leu Arg Met Tyr Ser Glu Asn His Arg
                180                 185                 190

Pro Pro Gly Lys Asn Tyr Phe Ala Arg Leu Leu Ser Ile Leu Thr Glu
            195                 200                 205

Leu Arg Thr Leu Gly Asn Met Asn Ala Glu Met Cys Phe Ser Leu Lys
210                 215                 220
```

Val Gln Asn Lys Lys Leu Pro Pro Phe Leu Ala Glu Ile Trp Asp Ile
225                 230                 235                 240

<210> SEQ ID NO 4
<211> LENGTH: 198
<212> TYPE: DNA
<213> ORGANISM: Choristoneura fumiferana

<400> SEQUENCE: 4
tgtctggtat gcggggacag agcctccgga taccactaca atgcgctcac gtgtgaaggg    60
tgtaaagggt tcttcagacg gagtgttacc aaaaatgcgg tttatatttg taaattcggt   120
cacgcttgcg aaatggacat gtacatgcga cggaaatgcc aggagtgccg cctgaagaag   180
tgcttagctg taggcatg                                                  198

<210> SEQ ID NO 5
<211> LENGTH: 66
<212> TYPE: PRT
<213> ORGANISM: Choristoneura fumiferana

<400> SEQUENCE: 5

Cys Leu Val Cys Gly Asp Arg Ala Ser Gly Tyr His Tyr Asn Ala Leu
1               5                   10                  15

Thr Cys Glu Gly Cys Lys Gly Phe Phe Arg Arg Ser Val Thr Lys Asn
            20                  25                  30

Ala Val Tyr Ile Cys Lys Phe Gly His Ala Cys Glu Met Asp Met Tyr
        35                  40                  45

Met Arg Arg Lys Cys Gln Glu Cys Arg Leu Lys Lys Cys Leu Ala Val
    50                  55                  60

Gly Met
65

<210> SEQ ID NO 6
<211> LENGTH: 441
<212> TYPE: DNA
<213> ORGANISM: Saccharomyces cerevisiae

<400> SEQUENCE: 6
atgaagctac tgtcttctat cgaacaagca tgcgatattt gccgacttaa aaagctcaag    60
tgctccaaag aaaaaccgaa gtgcgccaag tgtctgaaga caactgggag tgtcgctac   120 tctcccaaaa ccaaaaggtc tccgctgact agggcacatc tgacagaagt ggaatcaagg   180 ctagaaaagac tggaacagct atttctactg attttcctc gagaagacct tgacatgatt   240
ttgaaaatgg attctttaca ggatataaaa gcattgttaa caggattatt tgtacaagat   300
aatgtgaata agatgccgt cacagataga ttggcttcag tggagactga atgcctcta   360 acattgagac agcatagaat aagtgcgaca tcatcatcgg aagagagtag taacaaaggt   420
caaagacagt tgactgtatc g                                              441

<210> SEQ ID NO 7
<211> LENGTH: 147
<212> TYPE: PRT
<213> ORGANISM: Saccharomyces cerevisiae

<400> SEQUENCE: 7

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

```
Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Ser Glu Glu Ser Ser Asn Lys Gly Gln Arg Gln Leu
            130                 135                 140

Thr Val Ser
145

<210> SEQ ID NO 8
<211> LENGTH: 606
<212> TYPE: DNA
<213> ORGANISM: Escherichia coli

<400> SEQUENCE: 8
atgaaagcgt taacggccag gcaacaagag gtgtttgatc tcatccgtga tcacatcagc    60
cagacaggta tgccgccgac gcgtgcggaa atcgcgcagc gtttgggggtt ccgttcccca   120 aacgcggctg aagaacatct gaaggcgctg gcacgcaaag gcgttattga aattgtttcc   180
ggcgcatcac gcgggattcg tctgttgcag gaagaggaag aagggttgcc gctggtaggt   240
cgtgtggctg ccggtgaacc cacttctggcg caacagcata ttgaaggtca ttatcaggtc   300
gatccttcct tattcaagcc gaatgctgat ttcctgctgc gcgtcagcgg gatgtcgatg   360
aaagatatcg gcattatgga tggtgacttg ctggcagtgc ataaaactca ggatgtacgt   420
aacggtcagg tcgttgtcgc acgtattgat gacgaagtta ccgttaagcg cctgaaaaaa   480
cagggcaata aagtcgaact gttgccagaa aatagcgagt ttaaaccaat tgtcgtagat   540
cttcgtcagc agagcttcac cattgaaggg ctggcggttg ggttattcg caacggcgac   600 tggctg                                                              606

<210> SEQ ID NO 9
<211> LENGTH: 202
<212> TYPE: PRT
<213> ORGANISM: Escherichia coli

<400> SEQUENCE: 9

Met Lys Ala Leu Thr Ala Arg Gln Gln Glu Val Phe Asp Leu Ile Arg
  1               5                  10                  15

Asp His Ile Ser Gln Thr Gly Met Pro Pro Thr Arg Ala Glu Ile Ala
                 20                  25                  30

Gln Arg Leu Gly Phe Arg Ser Pro Asn Ala Ala Glu Glu His Leu Lys
             35                  40                  45

Ala Leu Ala Arg Lys Gly Val Ile Glu Ile Val Ser Gly Ala Ser Arg
 50                  55                  60

Gly Ile Arg Leu Leu Gln Glu Glu Glu Glu Gly Leu Pro Leu Val Gly
 65                  70                  75                  80

Arg Val Ala Ala Gly Glu Pro Leu Leu Ala Gln Gln His Ile Glu Gly
```

```
                85                  90                  95
His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
            115                 120                 125

Asp Leu Leu Ala Val His Lys Thr Gln Asp Val Arg Asn Gly Gln Val
        130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200
```

<210> SEQ ID NO 10
<211> LENGTH: 420
<212> TYPE: DNA
<213> ORGANISM: Choristoneura fumiferana

<400> SEQUENCE: 10

```
atgagacgcc gctggtccaa caacgggggc ttccagacgc tgcgaatgct cgaggagagc      60
tcgtccgaag tgacgtcgtc ctcagctctg ggtctgccgg ccgcgatggt tatgtctccg     120
gagtcgctcg cctcgccaga gtacggcggg ctcgagctct ggggatacga cgatgggttg     180
tcatacaaca cggcgcagtc cttgctgggc aatacttgca cgatgcagca gcagcaacag     240
acgcagccgc tgccgtcgat gccgttgcct atgccgccga ccacgccgaa gtctgaaaac     300
gagtctattt cctcaggccg tgaggaactg tcgccagctt caagtataaa tgggtgcagt     360
acagatggcg aggcacgacg tcagaagaag ggccctgcgc cccgtcagca gaggaactg     420
```

<210> SEQ ID NO 11
<211> LENGTH: 140
<212> TYPE: PRT
<213> ORGANISM: Choristoneura fumiferana

<400> SEQUENCE: 11

```
Met Arg Arg Arg Trp Ser Asn Asn Gly Gly Phe Gln Thr Leu Arg Met
1               5                   10                  15

Leu Glu Glu Ser Ser Ser Glu Val Thr Ser Ser Ser Ala Leu Gly Leu
            20                  25                  30

Pro Ala Ala Met Val Met Ser Pro Glu Ser Leu Ala Ser Pro Glu Tyr
        35                  40                  45

Gly Gly Leu Glu Leu Trp Gly Tyr Asp Asp Gly Leu Ser Tyr Asn Thr
    50                  55                  60

Ala Gln Ser Leu Leu Gly Asn Thr Cys Thr Met Gln Gln Gln Gln Gln
65                  70                  75                  80

Thr Gln Pro Leu Pro Ser Met Pro Leu Pro Met Pro Thr Thr Pro
                85                  90                  95

Lys Ser Glu Asn Glu Ser Ile Ser Gly Arg Glu Glu Leu Ser Pro
            100                 105                 110

Ala Ser Ser Ile Asn Gly Cys Ser Thr Asp Gly Glu Ala Arg Arg Gln
        115                 120                 125

Lys Lys Gly Pro Ala Pro Arg Gln Gln Glu Glu Leu
    130                 135                 140
```

<210> SEQ ID NO 12
<211> LENGTH: 271
<212> TYPE: DNA
<213> ORGANISM: herpes simplex virus 7

<400> SEQUENCE: 12

```
atgggcccta aaaagaagcg taaagtcgcc cccccgaccg atgtcagcct gggggacgag    60
ctccacttag acggcgagga cgtggcgatg gcgcatgccg acgcgctaga cgatttcgat   120
ctggacatgt tgggggacgg ggattccccg gggccgggat ttaccccca cgactccgcc   180
ccctacggcg ctctggatat ggccgacttc gagtttgagc agatgtttac cgatgccctt   240
ggaattgacg agtacggtgg ggaattcccg g                                  271
```

<210> SEQ ID NO 13
<211> LENGTH: 90
<212> TYPE: PRT
<213> ORGANISM: herpes simplex virus 7

<400> SEQUENCE: 13

```
Met Gly Pro Lys Lys Arg Lys Val Ala Pro Pro Thr Asp Val Ser
1               5                   10                  15

Leu Gly Asp Glu Leu His Leu Asp Gly Glu Asp Val Ala Met Ala His
                20                  25                  30

Ala Asp Ala Leu Asp Asp Phe Asp Leu Asp Met Leu Gly Asp Gly Asp
            35                  40                  45

Ser Pro Gly Pro Gly Phe Thr Pro His Asp Ser Ala Pro Tyr Gly Ala
        50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Pro
                85                  90
```

<210> SEQ ID NO 14
<211> LENGTH: 307
<212> TYPE: DNA
<213> ORGANISM: Saccharomyces cerevisiae

<400> SEQUENCE: 14

```
atgggtgctc ctccaaaaaa gaagagaaag gtagctggta tcaataaaga tatcgaggag    60
tgcaatgcca tcattgagca gtttatcgac tacctgcgca ccggacagga gatgccgatg   120
gaaatggcgg atcaggcgat taacgtggtg ccgggcatga cgccgaaaac cattcttcac   180
gccgggccgc cgatccagcc tgactggctg aaatcgaatg gttttcatga aattgaagcg   240
gatgttaacg ataccagcct cttgctgagt ggagatgcct cctacccta tgatgtgcca   300
gattatg                                                            307
```

<210> SEQ ID NO 15
<211> LENGTH: 102
<212> TYPE: PRT
<213> ORGANISM: Saccharomyces cerevisiae

<400> SEQUENCE: 15

```
Met Gly Ala Pro Pro Lys Lys Arg Lys Val Ala Gly Ile Asn Lys
1               5                   10                  15

Asp Ile Glu Glu Cys Asn Ala Ile Ile Glu Gln Phe Ile Asp Tyr Leu
                20                  25                  30
```

```
Arg Thr Gly Gln Glu Met Pro Met Glu Met Ala Asp Gln Ala Ile Asn
        35                  40                  45

Val Val Pro Gly Met Thr Pro Lys Thr Ile Leu His Ala Gly Pro Pro
 50                  55                  60

Ile Gln Pro Asp Trp Leu Lys Ser Asn Gly Phe His Glu Ile Glu Ala
 65                  70                  75                  80

Asp Val Asn Asp Thr Ser Leu Leu Leu Ser Gly Asp Ala Ser Tyr Pro
                 85                  90                  95

Tyr Asp Val Pro Asp Tyr
            100

<210> SEQ ID NO 16
<211> LENGTH: 807
<212> TYPE: DNA
<213> ORGANISM: Homo sapiens

<400> SEQUENCE: 16
cccatggaat tccagtacct gccagataca gacgatcgtc accggattga ggagaaacgt      60
aaaaggacat atgagacctt caagagcatc atgaagaaga gtcctttcag cggacccacc     120 gaccccggc  ctccacctcg acgcattgct gtgccttccc gcagctcagc ttctgtcccc     180
aagccagcac cccagccta  tccctttacg tcatccctga gcaccatcaa ctatgatgag     240
tttcccacca tggtgtttcc ttctgggcag atcagccagg cctcggcctt ggccccggcc     300
cctccccaag tcctgcccca ggctccagcc cctgcccctg ctccagccat ggtatcagct     360
ctggcccagg cccagccccc tgtcccagtc tagccccag  ccctcctca  ggctgtggcc     420 ccacctgccc ccaagcccac ccaggctggg gaaggaacgc tgtcagaggc cctgctgcag     480
ctgcagtttg atgatgaaga cctggggcc  ttgcttggca acagcacaga cccagctgtg     540
ttcacagacc tggcatccgt cgacaactcc gagtttcagc agctgctgaa ccagggcata     600
cctgtggccc cccacacaac tgagcccatg ctgatggagt accctgaggc tataactcgc     660
ctagtgacag gggcccagag gcccccgac  ccagctcctg ctccactggg ggccccgggg     720
ctccccaatg gcctcctttc aggagatgaa gacttctcct ccattgcgga catggacttc     780
tcagccctgc tgagtcagat cagctcc                                         807

<210> SEQ ID NO 17
<211> LENGTH: 269
<212> TYPE: PRT
<213> ORGANISM: Homo sapiens

<400> SEQUENCE: 17

Pro Met Glu Phe Gln Tyr Leu Pro Asp Thr Asp Asp Arg His Arg Ile
 1               5                  10                  15

Glu Glu Lys Arg Lys Arg Thr Tyr Glu Thr Phe Lys Ser Ile Met Lys
                20                  25                  30

Lys Ser Pro Phe Ser Gly Pro Thr Asp Pro Arg Pro Pro Arg Arg
                35                  40                  45

Ile Ala Val Pro Ser Arg Ser Ser Ala Ser Val Pro Lys Pro Ala Pro
 50                  55                  60

Gln Pro Tyr Pro Phe Thr Ser Ser Leu Ser Thr Ile Asn Tyr Asp Glu
 65                  70                  75                  80

Phe Pro Thr Met Val Phe Pro Ser Gly Gln Ile Ser Gln Ala Ser Ala
                 85                  90                  95

Leu Ala Pro Ala Pro Pro Gln Val Leu Pro Gln Ala Pro Ala Pro Ala
            100                 105                 110
```

```
Pro Ala Pro Ala Met Val Ser Ala Leu Ala Gln Ala Pro Ala Pro Val
        115                 120                 125
Pro Val Leu Ala Pro Gly Pro Pro Gln Ala Val Ala Pro Pro Ala Pro
    130                 135                 140
Lys Pro Thr Gln Ala Gly Glu Gly Thr Leu Ser Glu Ala Leu Leu Gln
145                 150                 155                 160
Leu Gln Phe Asp Asp Glu Asp Leu Gly Ala Leu Leu Gly Asn Ser Thr
                165                 170                 175
Asp Pro Ala Val Phe Thr Asp Leu Ala Ser Val Asp Asn Ser Glu Phe
            180                 185                 190
Gln Gln Leu Leu Asn Gln Gly Ile Pro Val Ala Pro His Thr Thr Glu
        195                 200                 205
Pro Met Leu Met Glu Tyr Pro Glu Ala Ile Thr Arg Leu Val Thr Gly
    210                 215                 220
Ala Gln Arg Pro Pro Asp Pro Ala Pro Ala Pro Leu Gly Ala Pro Gly
225                 230                 235                 240
Leu Pro Asn Gly Leu Leu Ser Gly Asp Glu Asp Phe Ser Ser Ile Ala
                245                 250                 255
Asp Met Asp Phe Ser Ala Leu Leu Ser Gln Ile Ser Ser
            260                 265

<210> SEQ ID NO 18
<211> LENGTH: 34
<212> TYPE: DNA
<213> ORGANISM: Artificial Sequence
<220> FEATURE:
<223> OTHER INFORMATION: 1X Ecdysone response element (EcRE)

<400> SEQUENCE: 18
tcgagagaca agggttcaat gcacttgtcc aatg                                34

<210> SEQ ID NO 19
<211> LENGTH: 19
<212> TYPE: DNA
<213> ORGANISM: Artificial Sequence
<220> FEATURE:
<223> OTHER INFORMATION: GAL4 response element

<400> SEQUENCE: 19
ggagtactgt cctccgagc                                                 19

<210> SEQ ID NO 20
<211> LENGTH: 36
<212> TYPE: DNA
<213> ORGANISM: Artificial Sequence
<220> FEATURE:
<223> OTHER INFORMATION: 2xLexAop response element

<400> SEQUENCE: 20
ctgctgtata taaaaccagt ggttatatgt acagta                              36

<210> SEQ ID NO 21
<211> LENGTH: 1054
<212> TYPE: DNA
<213> ORGANISM: Choristoneura fumiferana

<400> SEQUENCE: 21
cctgagtgcg tagtacccga gactcagtgc gccatgaagc ggaaagagaa gaaagcacag     60
aaggagaagg acaaactgcc tgtcagcacg acgacggtgg acgaccacat gccgcccatt    120
```

| | |
|---|---:|
| atgcagtgtg aacctccacc tcctgaagca gcaaggattc acgaagtggt cccaaggttt | 180 |
| ctctccgaca agctgttgga gacaaaccgg cagaaaaaca tcccccagtt gacagccaac | 240 |
| cagcagttcc ttatcgccag gctcatctgg taccaggacg ggtacgagca gccttctgat | 300 |
| gaagatttga gaggattac gcagacgtgg cagcaagcgg acgatgaaaa cgaagagtct | 360 |
| gacactccct tccgccagat cacagagatg actatcctca cggtccaact tatcgtggag | 420 |
| ttcgcgaagg gattgccagg gttcgccaag atctcgcagc ctgatcaaat tacgctgctt | 480 |
| aaggcttgct caagtgaggt aatgatgctc cgagtcgcgc gacgatacga tgcggcctca | 540 |
| gacagtgttc tgttcgcgaa caaccaagcg tacactcgcg acaactaccg caaggctggc | 600 |
| atggcctacg tcatcgagga tctactgcac ttctgccggt gcatgtactc tatggcgttg | 660 |
| gacaacatcc attacgcgct gctcacggct gtcgtcatct tttctgaccg gccagggttg | 720 |
| gagcagccgc aactggtgga agaaatccag cggtactacc tgaatacgct ccgcatctat | 780 |
| atcctgaacc agctgagcgg gtcggcgcgt tcgtccgtca tacggcaa gatcctctca | 840 |
| atcctctctg agctacgcac gctcggcatg caaaactcca acatgtgcat ctccctcaag | 900 |
| ctcaagaaca gaaagctgcc gccttcctc gaggagatct gggatgtggc ggacatgtcg | 960 |
| cacacccaac cgccgcctat cctcgagtcc cccacgaatc tctagcccct gcgcgcacgc | 1020 |
| atcgccgatg ccgcgtccgg ccgcgctgct ctga | 1054 |

```
<210> SEQ ID NO 22
<211> LENGTH: 309
<212> TYPE: DNA
<213> ORGANISM: Simian virus 40

<400> SEQUENCE: 22
```

| | |
|---|---:|
| ggtgtggaaa gtccccaggc tccccagcag gcagaagtat gcaaagcatg catctcaatt | 60 |
| agtcagcaac caggtgtgga agtccccag gctccccagc aggcagaagt atgcaaagca | 120 |
| tgcatctcaa ttagtcagca accatagtcc cgcccctaac tccgcccatc ccgcccctaa | 180 |
| ctccgcccag ttccgcccat tctccgcccc atggctgact aatttttttt atttatgcag | 240 |
| aggccgaggc cgcctcggcc tctgagctat tccagaagta gtgaggaggc ttttttggag | 300 |
| gcctaggct | 309 |

```
<210> SEQ ID NO 23
<211> LENGTH: 635
<212> TYPE: DNA
<213> ORGANISM: Locusta migratoria

<400> SEQUENCE: 23
```

| | |
|---|---:|
| tgcatacaga catgcctgtt gaacgcatac ttgaagctga aaaacgagtg gagtgcaaag | 60 |
| cagaaaacca agtggaatat gagctggtgg agtgggctaa acacatcccg cacttcacat | 120 |
| ccctacctct ggaggaccag gttctcctcc tcagagcagg ttggaatgaa ctgctaattg | 180 |
| cagcatttc acatcgatct gtagatgtta aagatggcat agtacttgcc actggtctca | 240 |
| cagtgcatcg aaattctgcc catcaagctg gagtcggcac aatatttgac agagttttga | 300 |
| cagaactggt agcaaagatg agagaaatga aaatggataa aactgaactt ggctgcttgc | 360 |
| gatctgttat tcttttcaat ccagaggtga ggggtttgaa atccgcccag gaagttgaac | 420 |
| ttctacgtga aaaagtatat gccgcttggg aagaatatac tagaacaaca catcccgatg | 480 |
| aaccaggaag atttgcaaaa cttttgcttc gtctgccttc tttacgttcc ataggcctta | 540 |
| agtgtttgga gcatttgttt ttctttcgcc ttattggaga tgttccaatt gatacgttcc | 600 | tgatggagat gcttgaatca ccttctgatt cataa                                   635

<210> SEQ ID NO 24
<211> LENGTH: 24
<212> TYPE: DNA
<213> ORGANISM: Artificial Sequence
<220> FEATURE:
<223> OTHER INFORMATION: synthetic E1b minimal promoter

<400> SEQUENCE: 24
tatataatgg atccccgggt accg                                               24

<210> SEQ ID NO 25
<211> LENGTH: 1653
<212> TYPE: DNA
<213> ORGANISM: Photinus pyralis

<400> SEQUENCE: 25
atggaagacg ccaaaaacat aaagaaaggc ccggcgccat tctatcctct agaggatgga        60
accgctggag agcaactgca taaggctatg aagagatacg ccctggttcc tggaacaatt       120
gcttttacag atgcacatat cgaggtgaac atcacgtacg cggaatactt cgaaatgtcc       180
gttcggttgg cagaagctat gaaacgatat gggctgaata caaatcacag aatcgtcgta       240
tgcagtgaaa actctcttca attctttatg ccggtgttgg gcgcgttatt tatcggagtt       300
gcagttgcgc ccgcgaacga catttataat gaacgtgaat tgctcaacag tatgaacatt       360
tcgcagccta ccgtagtgtt tgtttccaaa aaggggttgc aaaaaatttt gaacgtgcaa       420
aaaaaattac caataatcca gaaaattatt atcatggatt ctaaaacgga ttaccaggga       480
tttcagtcga tgtacacgtt cgtcacatct catctacctc ccggttttaa tgaatacgat       540
tttgtaccag agtcctttga tcgtgacaaa acaattgcac tgataatgaa ttcctctgga       600
tctactgggt tacctaaggg tgtggcccct ccgcatagaa ctgcctgcgt cagattctcg       660
catgccagag atcctatttt tggcaatcaa atcattccgg atactgcgat tttaagtgtt       720
gttccattcc atcacggttt tggaatgttt actacactcg atatttgat atgtggattt        780
cgagtcgtct taatgtatag atttgaagaa gagctgtttt tacgatccct tcaggattac       840
aaaattcaaa gtgcgttgct agtaccaacc ctattttcat tcttcgccaa aagcactctg       900
attgacaaat acgatttatc taatttacac gaaattgctt ctgggggcgc acctctttcg       960
aaagaagtcg ggaagcggt tgcaaaacgc ttccatcttc cagggatacg acaaggatat      1020
gggctcactg agactacatc agctattctg attacacccg agggggatga taaaccgggc      1080
gcggtcggta agttgttcc attttttgaa gcgaaggttg tggatctgga taccgggaaa       1140
acgctgggcg ttaatcagag aggcgaatta tgtgtcagag acctatgat tatgtccggt      1200
tatgtaaaca atccggaagc gaccaacgcc ttgattgaca aggatggatg gctacattct      1260
ggagacatag cttactggga cgaagacgaa cacttcttca tagttgaccg cttgaagtct      1320
ttaattaaat acaaaggata tcaggtggcc cccgctgaat tggaatcgat attgttacaa      1380
caccccaaca tcttcgacgc gggcgtggca ggtcttcccg acgatgacgc cggtgaactt      1440
cccgccgccg ttgttgtttt ggagcacgga aagacgatga cggaaaaaga gatcgtggat      1500
tacgtcgcca gtcaagtaac aaccgcgaaa agttgcgcg gaggagttgt gtttgtggac      1560
gaagtaccga aaggtcttac cggaaaactc gacgcaagaa aaatcagaga gatcctcata      1620
aaggccaaga agggcggaaa gtccaaattg taa                                   1653

<210> SEQ ID NO 26
<211> LENGTH: 541
<212> TYPE: PRT
<213> ORGANISM: Choristoneura fumiferana

<400> SEQUENCE: 26

```
Met Arg Arg Arg Trp Ser Asn Asn Gly Gly Phe Gln Thr Leu Arg Met
1               5                   10                  15

Leu Glu Glu Ser Ser Ser Glu Val Thr Ser Ser Ser Ala Leu Gly Leu
            20                  25                  30

Pro Ala Ala Met Val Met Ser Pro Glu Ser Leu Ala Ser Pro Glu Tyr
        35                  40                  45

Gly Gly Leu Glu Leu Trp Gly Tyr Asp Asp Gly Leu Ser Tyr Asn Thr
    50                  55                  60

Ala Gln Ser Leu Leu Gly Asn Thr Cys Thr Met Gln Gln Gln Gln Gln
65                  70                  75                  80

Thr Gln Pro Leu Pro Ser Met Pro Leu Pro Met Pro Pro Thr Thr Pro
                85                  90                  95

Lys Ser Glu Asn Glu Ser Ile Ser Ser Gly Arg Glu Glu Leu Ser Pro
            100                 105                 110

Ala Ser Ser Ile Asn Gly Cys Ser Thr Asp Gly Glu Ala Arg Arg Gln
        115                 120                 125

Lys Lys Gly Pro Ala Pro Arg Gln Gln Glu Glu Leu Cys Leu Val Cys
    130                 135                 140

Gly Asp Arg Ala Ser Gly Tyr His Tyr Asn Ala Leu Thr Cys Glu Gly
145                 150                 155                 160

Cys Lys Gly Phe Phe Arg Arg Ser Val Thr Lys Asn Ala Val Tyr Ile
                165                 170                 175

Cys Lys Phe Gly His Ala Cys Glu Met Asp Met Tyr Met Arg Arg Lys
            180                 185                 190

Cys Gln Glu Cys Arg Leu Lys Lys Cys Leu Ala Val Gly Met Arg Pro
        195                 200                 205

Glu Cys Val Val Pro Glu Thr Gln Cys Ala Met Lys Arg Lys Glu Lys
    210                 215                 220

Lys Ala Gln Lys Glu Lys Asp Lys Leu Pro Val Ser Thr Thr Thr Val
225                 230                 235                 240

Asp Asp His Met Pro Pro Ile Met Gln Cys Glu Pro Pro Pro Pro Glu
                245                 250                 255

Ala Ala Arg Ile His Glu Val Val Pro Arg Phe Leu Ser Asp Lys Leu
            260                 265                 270

Leu Glu Thr Asn Arg Gln Lys Asn Ile Pro Gln Leu Thr Ala Asn Gln
        275                 280                 285

Gln Phe Leu Ile Ala Arg Leu Ile Trp Tyr Gln Asp Gly Tyr Glu Gln
    290                 295                 300

Pro Ser Asp Glu Asp Leu Lys Arg Ile Thr Gln Thr Trp Gln Gln Ala
305                 310                 315                 320

Asp Asp Glu Asn Glu Glu Ser Asp Thr Pro Phe Arg Gln Ile Thr Glu
                325                 330                 335

Met Thr Ile Leu Thr Val Gln Leu Ile Val Glu Phe Ala Lys Gly Leu
            340                 345                 350

Pro Gly Phe Ala Lys Ile Ser Gln Pro Asp Gln Ile Thr Leu Leu Lys
        355                 360                 365

Ala Cys Ser Ser Glu Val Met Met Leu Arg Val Ala Arg Arg Tyr Asp
    370                 375                 380
```

```
Ala Ala Ser Asp Ser Val Leu Phe Ala Asn Asn Gln Ala Tyr Thr Arg
385                 390                 395                 400

Asp Asn Tyr Arg Lys Ala Gly Met Ala Tyr Val Ile Glu Asp Leu Leu
            405                 410                 415

His Phe Cys Arg Cys Met Tyr Ser Met Ala Leu Asp Asn Ile His Tyr
        420                 425                 430

Ala Leu Leu Thr Ala Val Val Ile Phe Ser Asp Arg Pro Gly Leu Glu
            435                 440                 445

Gln Pro Gln Leu Val Glu Glu Ile Gln Arg Tyr Tyr Leu Asn Thr Leu
    450                 455                 460

Arg Ile Tyr Ile Leu Asn Gln Leu Ser Gly Ser Ala Arg Ser Ser Val
465                 470                 475                 480

Ile Tyr Gly Lys Ile Leu Ser Ile Leu Ser Glu Leu Arg Thr Leu Gly
            485                 490                 495

Met Gln Asn Ser Asn Met Cys Ile Ser Leu Lys Leu Lys Asn Arg Lys
                500                 505                 510

Leu Pro Pro Phe Leu Glu Glu Ile Trp Asp Val Ala Asp Met Ser His
            515                 520                 525

Thr Gln Pro Pro Pro Ile Leu Glu Ser Pro Thr Asn Leu
    530                 535                 540

<210> SEQ ID NO 27
<211> LENGTH: 1623
<212> TYPE: DNA
<213> ORGANISM: Choristoneura fumiferana

<400> SEQUENCE: 27
atgagacgcc gctggtccaa caacgggggc ttccagacgc tgcgaatgct cgaggagagc      60
tcgtccgaag tgacgtcgtc ctcagctctg gtctgccgg ccgcgatggt tatgtctccg     120
gagtcgctcg cctcgccaga gtacggcggg ctcgagctct ggggatacga cgatgggttg     180
tcatacaaca cggcgcagtc cttgctgggc aatacttgca cgatgcagca gcagcaacag     240
acgcagccgc tgccgtcgat gccgttgcct atgccgccga ccacgccgaa gtctgaaaac     300
gagtctattt cctcaggccg tgaggaactg tcgccagctt caagtataaa tgggtgcagt     360
acagatggcg aggcacgacg tcagaagaag ggcctgcgc ccgtcagca agaggaactg      420 tgtctggtat gcggggacag agcctccgga taccactaca atgcgctcac gtgtgaaggg     480
tgtaaagggt tcttcagacg gagtgttacc aaaaatgcgg tttatatttg taaattcggt     540
cacgcttgcg aaatggacat gtacatgcga cggaaatgcc aggagtgccg cctgaagaag     600
tgcttagctg taggcatgag gcctgagtgc gtagtacccg agactcagtg cgccatgaag     660
cggaaagaga gaaagcaca gaaggagaag acaaactgc ctgtcagcac gacgacggtg      720
gacgaccaca tgccgcccat tatgcagtgt gaacctccac ctcctgaagc agcaaggatt     780
cacgaagtgg tcccaaggtt tctctccgac aagctgttgg agacaaaccg gcagaaaaac     840
atcccccagt tgacagccaa ccagcagttc cttatcgcca ggctcatctg gtaccaggac     900
gggtacgagc agccttctga tgaagatttg aagaggatta cgcagacgtg gcagcaagcg     960
gacgatgaaa acgaagagtc tgacactccc ttccgccaga tcacagagat gactatcctc    1020
acggtccaac ttatcgtgga gttcgcgaag ggattgccag ggttcgccaa gatctcgcag    1080
cctgatcaaa ttacgctgct taaggcttgc tcaagtgagg taatgatgct ccgagtcgcg    1140
cgacgatacg atgcggcctc agacagtgtt ctgttcgcga caaccaagc gtacactcgc    1200
```

```
gacaactacc gcaaggctgg catggcctac gtcatcgagg atctactgca cttctgccgg    1260
tgcatgtact ctatggcgtt ggacaacatc cattacgcgc tgctcacggc tgtcgtcatc    1320
ttttctgacc ggccagggtt ggagcagccg caactggtgg aagaaatcca gcggtactac    1380
ctgaatacgc tccgcatcta tatcctgaac cagctgagcg gtcggcgcg ttcgtccgtc     1440 atatacggca agatcctctc aatcctctct gagctacgca cgctcggcat gcaaaactcc    1500
aacatgtgca tctccctcaa gctcaagaac agaaagctgc cgccttccct cgaggagatc    1560
tgggatgtgg cggacatgtc gcacacccaa ccgccgccta tcctcgagtc ccccacgaat    1620
ctc                                                                  1623

<210> SEQ ID NO 28
<211> LENGTH: 702
<212> TYPE: DNA
<213> ORGANISM: Artificial Sequence
<220> FEATURE:
<223> OTHER INFORMATION: Baculovirus IE1 promoter

<400> SEQUENCE: 28
cccgggccag ttgcacaaca ctattatcga tttgcagttc gggacataaa tgtttaaata    60
tatcgatgtc tttgtgatgc gcgcgacatt tttgtaggtt attgataaaa tgaacggata    120
cgttgcccga cattatcatt aaatccttgg cgtagaattt gtcgggtcca ttgtccgtgt    180
gcgctagcat gcccgtaacg gacctcgtac ttttggcttc aaaggttttg cgcacagaca    240
aaatgtgcca cacttgcagc tctgcatgtg tgcgcgttac cacaaatccc aacggcgcag    300
tgtacttgtt gtatgcaaat aaatctcgat aaaggcgcgg cgcgcgaatg cagctgatca    360
cgtacgctcc tcgtgttccg ttcaaggacg gtgttatcga cctcagatta atgtttatcg    420
gccgactgtt ttcgtatccg ctcaccaaac gcgttttgc attaacattg tatgtcggcg    480
gatgttctat atctaatttg aataaataaa cgataaccgc gttggtttta gagggcataa    540
taaaagaaat attgttatcg tgttcgccat tagggcagta taaattgacg ttcatgttgg    600
atattgtttc agttgcaagt tgacactggc ggcgacaaga tcgtgaacaa ccaagtgact    660
atagaattca ctcgaggcta gcataagatc taagctagcg cc                      702

<210> SEQ ID NO 29
<211> LENGTH: 3157
<212> TYPE: DNA
<213> ORGANISM: Escherichia coli

<400> SEQUENCE: 29 atgggggggtt ctcatcatca tcatcatcat ggtatggcta gcatgactgg tggacagcaa    60
atgggtcggg atctgtacga cgatgacgat aaggtaccta aggatcagct ggagttgat     120 cccgtcgttt tacaacgtcg tgactgggaa accctggcg ttacccaact taatcgcctt     180
gcagcacatc cccctttcgc cagctggcgt aatagcgaag aggcccgcac cgatcgccct    240
tcccaacagt tgcgcagcct gaatggcgaa tggcgctttg cctggtttcc ggcaccagaa    300
gcggtgccgg aaagctggct ggagtgcgat cttcctgagg ccgatactgt cgtcgtcccc    360
tcaaactggc agatgcacgg ttacgatgcg cccatctaca ccaacgtaac ctatcccatt    420
acggtcaatc cgccgtttgt tcccacggag aatccgacgg ttgttactc gctcacattt    480 aatgttgatg aaagctggct acaggaaggc cagacgcgaa ttattttga tggcgttaac    540 tcggcgtttc atctgtggtg caacgggcgc tgggtcggtt acggccagga cagtcgtttg    600
ccgtctgaat ttgacctgag cgcatttttta cgcgccggag aaaaccgcct cgcggtgatg    660
```

-continued

```
gtgctgcgtt ggagtgacgg cagttatctg gaagatcagg atatgtggcg gatgagcggc    720 atttccgtg acgtctcgtt gctgcataaa ccgactacac aaatcagcga tttccatgtt     780
gccactcgct ttaatgatga tttcagccgc gctgtactgg aggctgaagt tcagatgtgc    840
ggcgagttgc gtgactacct acgggtaaca gtttctttat ggcagggtga aacgcaggtc    900
gccagcggca ccgcgccttt cggcggtgaa attatcgatg agcgtggtgg ttatgccgat    960
cgcgtcacac tacgtctgaa cgtcgaaaac ccgaaactgt ggagcgccga atcccgaat   1020 ctctatcgtg cggtggttga actgcacacc gccgacggca cgctgattga agcagaagcc   1080
tgcgatgtcg gtttccgcga ggtgcggatt gaaaatggtc tgctgctgct gaacggcaag   1140
ccgttgctga ttcgaggcgt taaccgtcac gagcatcatc ctctgcatgg tcaggtcatg   1200
gatgagcaga cgatggtgca ggatatcctg ctgatgaagc agaacaactt taacgccgtg   1260
cgctgttcgc attatccgaa ccatccgctg tggtacacgc tgtgcgaccg ctacggcctg   1320
tatgtggtgg atgaagccaa tattgaaacc cacggcatgg tgccaatgaa tcgtctgacc   1380
gatgatccgc gctggctacc ggcgatgagc gaacgcgtaa cgcgaatggt gcagcgcgat   1440
cgtaatcacc cgagtgtgat catctggtcg ctggggaatg aatcaggcca cggcgctaat   1500
cacgacgcgc tgtatcgctg gatcaaatct gtcgatcctt cccgcccggt gcagtatgaa   1560
ggcggcggag ccgacaccac ggccaccgat attatttgcc cgatgtacgc gcgcgtggat   1620
gaagaccagc ccttcccggc tgtgccgaaa tggtccatca aaaaatggct ttcgctacct   1680
ggagagacgc gcccgctgat cctttgcgaa tacgcccacg cgatgggtaa cagtcttggc   1740
ggtttcgcta aatactggca ggcgtttcgt cagtatcccc gtttacaggg cggcttcgtc   1800
tgggactggg tggatcagtc gctgattaaa tatgatgaaa acggcaaccc gtggtcggct   1860
tacggcggtg attttggcga tacgccgaac gatcgccagt tctgtatgaa cggtctggtc   1920
tttgccgacc gcacgccgca tccagcgctg acggaagcaa acaccagca gcagttttc    1980 cagttccgtt tatccgggca aaccatcgaa gtgaccagcg aatacctgtt ccgtcatagc   2040
gataacgagc tcctgcactg gatggtggcg ctggatggta agccgctggc aagcggtgaa   2100
gtgcctctgg atgtcgctcc acaaggtaaa cagttgattg aactgcctga actaccgcag   2160
ccggagagcg ccgggcaact ctggctcaca gtacgcgtag tgcaaccgaa cgcgaccgca   2220
tggtcagaag ccgggcacat cagcgcctgg cagcagtggc gtctggcgga aaacctcagt   2280
gtgacgctcc ccgccgcgtc ccacgccatc ccgcatctga ccaccagcga aatggatttt   2340
tgcatcgagc tgggtaataa gcgttggcaa tttaaccgcc agtcaggctt tctttcacag   2400
atgtggattg gcgataaaaa acaactgctg acgccgctgc gcgatcagtt cacccgtgca   2460
ccgctggata cgacattggg cgtaagtgaa gcgaccgca ttgaccctaa cgcctgggtc    2520
gaacgctgga aggcggcggg ccattaccag gccgaagcag cgttgttgca gtgcacggca   2580
gatacacttg ctgatgcggt gctgattacg accgctcacg cgtggcagca tcaggggaaa   2640 accttatttta tcagccggaa aacctaccgg attgatggta gtggtcaaat ggcgattacc   2700
gttgatgttg aagtggcgag cgatacaccg catccggcgc ggattggcct gaactgccag   2760
ctggcgcagg tagcagagcg ggtaaactgg ctcggattag gccgcaagga aaactatccc   2820
gaccgcctta ctgccgcctg ttttgaccgc tgggatctgc cattgtcaga catgtatacc   2880
ccgtacgtct tcccgagcga aaacggtctg cgctgcggga cgcgcgaatt gaattatggc   2940
ccacaccagt ggcgcggcga cttccagttc aacatcagcc gctacagtca acagcaactg   3000
```

-continued

```
atggaaacca gccatcgcca tctgctgcac gcggaagaag gcacatggct gaatatcgac   3060
ggtttccata tggggattgg tggcgacgac tcctggagcc cgtcagtatc ggcggaatta   3120
cagctgagcg ccggtcgcta ccattaccag ttggtct                            3157

<210> SEQ ID NO 30
<211> LENGTH: 4375
<212> TYPE: DNA
<213> ORGANISM: Choristoneura fumiferana

<400> SEQUENCE: 30
tgtaattttg atgggcgccg tgatgcaccg tgtgccatat tgccatccag tcgaatagaa     60
aaaaaaaaaa aaaaaaaaat atcagttgtt ttgtccctcg ctcgctttcg agtgtattcg    120
gaatattaga cgtcataatt cacgagtgtc ttttaaattt atatagcgat tagcggggcc    180
gtttgttgga cgtgcgcttg cgtttagtgg agtgcaggga tagtgaggcg agtatggtag    240
ttcgtggtca tgtcaagtgt ggcgaagaaa gacaagccga cgatgtcggt gacggcgctg    300
atcaactggg cgcggccggc gccgccaggc ccgccgcagc cgcagtcagc gtcgcctgcg    360
ccggcagcca tgctgcagca gctcccgacg cagtcaatgc agtcgttaaa ccacatccca    420
actgtcgatt gctcgctcga tatgcagtgg cttaatttag aacctggatt catgtcgcct    480
atgtcacctc ctgagatgaa accagacacc gccatgcttg atgggctacg agacgacgcc    540
acttcgccgc ctaacttcaa gaactacccg cctaatcacc ccctgagtgg ctccaaacac    600
ctatgctcta tatgcggcga cagggcgtct gggaagcact atggggtgta cagttgcgaa    660
ggatgcaagg gtttcttcaa gcggaccgtc cggaaggacc tgtcgtacgc ttgccgggag    720
gagcggaact gcatcataga caagcgacaa aggaaccgat gccagtactg ccgctatcaa    780
aagtgtttgg cttgcggtat gaagcgagag gcggtgcaag aggagcgcca gaggaatgct    840
cgcggcgcgg aggatgcgca cccgagtagc tcggtgcagg taagcgatga gctgtcaatc    900
gagcgcctaa cggagatgga gtctttggtg gcagatccca gcgaggagtt ccagttcctc    960
cgcgtggggc ctgacagcaa cgtgcctcca cgttaccgcg cgcccgtctc ctccctctgc   1020
caaataggca acaagcaaat agcggcgttg gtggtatggg cgcgcgacat ccctcatttc   1080
gggcagctgg agctggacga tcaagtggta ctcatcaagg cctcctggaa tgagctgcta   1140
ctcttcgcca tcgcctggcg ctctatggag tatttggaag atgagaggga gaacggggac   1200
ggaacgcgga gcaccactca gccacaactg atgtgtctca tgcctggcat gacgttgcac   1260
cgcaactcgg cgcagcaggc gggcgtgggc gccatcttcg accgcgtgct gtccgagctc   1320
agtctgaaga tgcgcacctt gcgcatggac caggccgagt acgtcgcgct caaagccatc   1380
gtgctgctca accctgatgt gaaaggactg aagaatcggc aagaagttga cgttttgcga   1440
gaaaaaatgt tctcttgcct ggacgactac tgccggcggt cgcgaagcaa cgaggaaggc   1500
cggtttgcgt ccttgctgct gcggctgcca gctctccgct ccatctcgct caagagcttc   1560
gaacacctct acttcttcca cctcgtggcc gaaggctcca tcagcggata catacgagag   1620
gcgctccgaa accacgcgcc tccgatcgac gtcaatgcca tgatgtaaag tgcgatacac   1680
gccctgccga tgtgagaaga actatggcta atagaagcga aactgaatac atctagggtg   1740
ggacttaact tgggactatc attaaagtat cacgcaaatt atgcgtagtc agaaagtcgc   1800
gtcgatcaaa ctttttttata aacgaattga gtttctaacg actgcaacac agcggagttt   1860
tgcttctgat agtttttatt ctaatggtta agatgcttta cacgggcatt attgacattc   1920
aagtgtaagt ggaagttgac aaccttgaca tttatatcac gtttgtaatt ggttaaataa   1980
```

```
attaattaat cacaagtaag actaacatca acgtcacgat actaacgcca tttagtgata    2040
tttttcatgt caagaaactc attgttttga taaaatattt ttctaattac tccagtgaac    2100
tcatccaaat gtgacccagt ttcccgcaga gttgcccgtg taaaatcatc tttagggaca    2160 tatccccgc tatctcatga aattccaagg atcagtaggg gccaattccc ccgatgtgtt    2220
gggaggcaga attttcgata atctacgact attgttagcc tacgaattag ttgaattttt    2280
tgaaattatt tttattaagt cgccactttc caaacacatc agcagggtat atgtgcaatt    2340
ttgtaacgat aactctattc atttctgata tttatcgaaa ttttatctta cataacatgc    2400
tggctggtcc aggtgtttgg tagttacata tgtatctacg gtttgtttta aattatagct    2460
tttttattgt aatctgtata aaattgagtt atcttacttc acactacgat cgagtaaacc    2520
catcgtcagc tacgaaaaac taatcgtata aggcgtaaga gtaaataact aattgacaac    2580
cagcaacgag gaccacctca gtcctcgtgc ttacattgtg ccgtagctta atatgatgga    2640
agctgtcgtc gttacgacat tagataaagt gcatgaatac caaaaatgta ccatcccgta    2700
ctgatctctc atgctctcgc tgcgtgggac ccgtgtcgag tgtcgtaagg actgactaat    2760
attttagact aggcgtctat gcttcagtaa ttccttatac atattataag tcatccaaat    2820
aacgagtaag gcggcatgtt gagatcagca ttccgagagt caaagagccc ctaacgtgac    2880
tgagaagtag agacaataca ctgattttct gagatgaacg caaccgagat tgacactaaa    2940
aatctattta tggatttcaa aatggcgatg cttgattgtc tgcggcgtgg atagactgaa    3000
atgggtttgc ttaacactgg atattgtttt tattagttaa tagtcttaca ttgcaagttg    3060
gtaattcggt gctaatatcg accggtttgt taactatcta acggttccca gtgtcaggca    3120
cacatctttc ccaagcagac aacgcaagag tgtacaaaat gtacatgtta caaaataagg    3180
aacattcgtc ggataagtgt aacagttgat aggtaaagaa aatggggccg cctctttatt    3240
attacgtagc cgtaaaatta ttaacgtatt tagtttagat gttcagctaa ttaggataat    3300
tctatttgtc gagtacctag atgtccatag tgaattaata taataattag actgttacgc    3360
gtaggtaatt ataaagttta ccaaatctct cttcaaagca aaactttgt acacttccgt    3420 actgagacgt cgtagcttat tctgattcac gaaaatatttg gatcacattg ttacaaggcg    3480
accgtcacgt agtatatgat tatttacaaa tgacacgtat gtatcaatgc tataagtgtt    3540
ttcgttacat atgtcggtgc tttaacgtgc atttcgatgt gcagattaaa aatagcaaga    3600
aatcttgaaa ttgttttaga aaatatttga tttccttatt gaaagttatt tttaaatgta    3660
aatatttcgt aatcataata attatgtatt gtgtagttat ttcaccttta cggttgggat    3720
attatttaat ggtggcctac gaaagtgatt ataaccatcc gcgtcctcaa aaaggccagt    3780 ttattttttgt acctcataca tactaattac gtaagtaata tcaggcgaat ggttgactaa    3840
caactaacca gtattaaaaa ttaaaagact tcgtcctaat aaaatgtaat atctatgtat    3900
aaaaatgaaa aatctggcgt ataataggta aaattaaact agattgttaa tgaatgtgat    3960
gtctcataaa cgtttagttt ttaatgagaa acatgtttag tcgcctacta taagacgaga    4020
cggcaagctc accgagttaa ctcgtaaaca ggaatgttga aaaagatgac acaatttata    4080
tttggtattg aaattatgac taaccatgcg ctctatcgtt tgttatggat gcatagtatt    4140
gctgttgaaa ataatggaat taggtaatta ctgcattaat gttgaaaact tgatattatt    4200
ctatggttgg gtatgaattc tatgttggaa gtgttgcagc ggttgtaaag atgatttata    4260
atgatgttca ctaaatatct gactaaatgt aagttatttt ttttttgtata gacatagctt    4320
```

```
taagatgaag gtgattaaac tttatcctta tcacaataaa aaaaaaaaaa aaaaa      4375

<210> SEQ ID NO 31
<211> LENGTH: 1878
<212> TYPE: DNA
<213> ORGANISM: Drosophila melanogaster

<400> SEQUENCE: 31
ggacctgcgc cacgggtgca agaggagctg tgcctggttt gcggcgacag ggcctccggc     60
taccactaca acgccctcac ctgtgagggc tgcaaggggt tctttcgacg cagcgttacg    120
aagagcgccg tctactgctg caagttcggg cgcgcctgcg aaatggacat gtacatgagg    180
cgaaagtgtc aggagtgccg cctgaaaaag tgcctggccg tgggtatgcg gccggaatgc    240
gtcgtcccgg agaaccaatg tgcgatgaag cggcgcgaaa agaaggccca gaaggagaag    300
gacaaaatga ccacttcgcc gagctctcag catggcggca atggcagctt ggcctctggt    360
ggcggccaag actttgttaa gaaggagatt cttgacctta tgacatgcga gccgccccag    420
catgccacta ttccgctact acctgatgaa atattggcca agtgtcaagc gcgcaatata    480
ccttccttaa cgtacaatca gttggccgtt atatacaagt taatttggta ccaggatggc    540
tatgagcagc catctgaaga ggatctcagg cgtataatga gtcaacccga tgagaacgag    600
agccaaacgg acgtcagctt tcggcatata accgagataa ccatactcac ggtccagttg    660
attgttgagt ttgctaaagg tctaccagcg tttacaaaga taccccagga ggaccagatc    720
acgttactaa aggcctgctc gtcggaggtg atgatgctgc gtatggcacg acgctatgac    780
cacagctcgg actcaatatt cttcgcgaat aatagatcat atacgcggga ttcttacaaa    840
atggccggaa tggctgataa cattgaagac ctgctgcatt tctgccgcca aatgttctcg    900
atgaaggtgg acaacgtcga atacgcgctt ctcactgcca ttgtgatctt ctcggaccgg    960
ccgggcctgg agaaggccca actagtcgaa gcgatccaga gctactacat cgacacgcta   1020
cgcatttata tactcaaccg ccactgcggc gactcaatga gcctcgtctt ctacgcaaag   1080
ctgctctcga tcctcaccga gctgcgtacg ctgggcaacc agaacgccga tgtgtttc    1140
tcactaaagc tcaaaaaccg caaactgccc aagttcctcg aggagatctg ggacgttcat   1200
gccatcccgc catcggtcca gtcgcacctt cagattaccc aggaggagaa cgagcgtctc   1260
gagcgggctg agcgtatgcg ggcatcggtt ggggggcgcca ttaccgccgg cattgattgc   1320
gactctgcct ccacttcggc ggcggcagcc gcggcccagc atcagcctca gcctcagccc   1380
cagccccaac cctcctccct gacccagaac gattcccagc accagacaca gccgcagcta   1440
caacctcagc taccacctca gctgcaaggt caactgcaac cccagctcca accacagctt   1500
cagacgcaac tccagccaca gattcaacca cagccacagc tccttcccgt ctccgctccc   1560
gtgcccgcct ccgtaaccgc acctggttcc ttgtccgcgg tcagtacgag cagcgaatac   1620
atgggcggaa gtgcggccat aggacccatc acgccggcaa ccaccagcag tatcacggct   1680
gccgttaccg ctagctccac cacatcagcg gtaccgatgg caacggagt tggagtcggt    1740
gttggggtgg gcggcaacgt cagcatgtat gcgaacgccc agacggcgat ggccttgatg   1800
ggtgtagccc tgcattcgca ccaagagcag cttatcgggg gagtggcggt taagtcggag   1860
cactcgacga ctgcatag                                                 1878

<210> SEQ ID NO 32
<211> LENGTH: 878
<212> TYPE: PRT
<213> ORGANISM: Drosophila melanogaster
```

<400> SEQUENCE: 32

```
Met Lys Arg Arg Trp Ser Asn Asn Gly Gly Phe Met Arg Leu Pro Glu
1               5                   10                  15

Glu Ser Ser Ser Glu Val Thr Ser Ser Ser Asn Gly Leu Val Leu Pro
            20                  25                  30

Ser Gly Val Asn Met Ser Pro Ser Ser Leu Asp Ser His Asp Tyr Cys
        35                  40                  45

Asp Gln Asp Leu Trp Leu Cys Gly Asn Glu Ser Gly Ser Phe Gly Gly
    50                  55                  60

Ser Asn Gly His Gly Leu Ser Gln Gln Gln Ser Val Ile Thr Leu
65                  70                  75                  80

Ala Met His Gly Cys Ser Ser Thr Leu Pro Ala Gln Thr Thr Ile Ile
                85                  90                  95

Pro Ile Asn Gly Asn Ala Asn Gly Asn Gly Ser Thr Asn Gly Gln
                100                 105                 110

Tyr Val Pro Gly Ala Thr Asn Leu Gly Ala Leu Ala Asn Gly Met Leu
            115                 120                 125

Asn Gly Gly Phe Asn Gly Met Gln Gln Gln Ile Gln Asn Gly His Gly
130                 135                 140

Leu Ile Asn Ser Thr Thr Pro Ser Thr Pro Thr Thr Pro Leu His Leu
145                 150                 155                 160

Gln Gln Asn Leu Gly Gly Ala Gly Gly Gly Ile Gly Gly Met Gly
                165                 170                 175

Ile Leu His His Ala Asn Gly Thr Pro Asn Gly Leu Ile Gly Val Val
                180                 185                 190

Gly Gly Gly Gly Gly Val Gly Leu Gly Val Gly Gly Gly Val Gly
            195                 200                 205

Gly Leu Gly Met Gln His Thr Pro Arg Ser Asp Ser Val Asn Ser Ile
            210                 215                 220

Ser Ser Gly Arg Asp Asp Leu Ser Pro Ser Ser Ser Leu Asn Gly Tyr
225                 230                 235                 240

Ser Ala Asn Glu Ser Cys Asp Ala Lys Lys Ser Lys Lys Gly Pro Ala
                245                 250                 255

Pro Arg Val Gln Glu Glu Leu Cys Leu Val Cys Gly Asp Arg Ala Ser
            260                 265                 270

Gly Tyr His Tyr Asn Ala Leu Thr Cys Glu Gly Cys Lys Gly Phe Phe
            275                 280                 285

Arg Arg Ser Val Thr Lys Ser Ala Val Tyr Cys Cys Lys Phe Gly Arg
            290                 295                 300

Ala Cys Glu Met Asp Met Tyr Met Arg Arg Lys Cys Gln Glu Cys Arg
305                 310                 315                 320

Leu Lys Lys Cys Leu Ala Val Gly Met Arg Pro Glu Cys Val Val Pro
                325                 330                 335

Glu Asn Gln Cys Ala Met Lys Arg Arg Glu Lys Ala Gln Lys Glu
                340                 345                 350

Lys Asp Lys Met Thr Thr Ser Pro Ser Ser Gln His Gly Gly Asn Gly
            355                 360                 365

Ser Leu Ala Ser Gly Gly Gly Gln Asp Phe Val Lys Lys Glu Ile Leu
            370                 375                 380

Asp Leu Met Thr Cys Glu Pro Pro Gln His Ala Thr Ile Pro Leu Leu
385                 390                 395                 400

Pro Asp Glu Ile Leu Ala Lys Cys Gln Ala Arg Asn Ile Pro Ser Leu
```

-continued

```
                405                 410                 415
Thr Tyr Asn Gln Leu Ala Val Ile Tyr Lys Leu Ile Trp Tyr Gln Asp
                    420                 425                 430
Gly Tyr Glu Gln Pro Ser Glu Glu Asp Leu Arg Arg Ile Met Ser Gln
                    435                 440                 445
Pro Asp Glu Asn Glu Ser Gln Thr Asp Val Ser Phe Arg His Ile Thr
                    450                 455                 460
Glu Ile Thr Ile Leu Thr Val Gln Leu Ile Val Glu Phe Ala Lys Gly
465                 470                 475                 480
Leu Pro Ala Phe Thr Lys Ile Pro Gln Glu Asp Gln Ile Thr Leu Leu
                    485                 490                 495
Lys Ala Cys Ser Ser Glu Val Met Met Leu Arg Met Ala Arg Arg Tyr
                    500                 505                 510
Asp His Ser Ser Asp Ser Ile Phe Phe Ala Asn Asn Arg Ser Tyr Thr
                    515                 520                 525
Arg Asp Ser Tyr Lys Met Ala Gly Met Ala Asp Asn Ile Glu Asp Leu
                    530                 535                 540
Leu His Phe Cys Arg Gln Met Phe Ser Met Lys Val Asp Asn Val Glu
545                 550                 555                 560
Tyr Ala Leu Leu Thr Ala Ile Val Ile Phe Ser Asp Arg Pro Gly Leu
                    565                 570                 575
Glu Lys Ala Gln Leu Val Glu Ala Ile Gln Ser Tyr Tyr Ile Asp Thr
                    580                 585                 590
Leu Arg Ile Tyr Ile Leu Asn Arg His Cys Gly Asp Ser Met Ser Leu
                    595                 600                 605
Val Phe Tyr Ala Lys Leu Leu Ser Ile Leu Thr Glu Leu Arg Thr Leu
                    610                 615                 620
Gly Asn Gln Asn Ala Glu Met Cys Phe Ser Leu Lys Leu Lys Asn Arg
625                 630                 635                 640
Lys Leu Pro Lys Phe Leu Glu Glu Ile Trp Asp Val His Ala Ile Pro
                    645                 650                 655
Pro Ser Val Gln Ser His Leu Gln Ile Thr Gln Glu Glu Asn Glu Arg
                    660                 665                 670
Leu Glu Arg Ala Glu Arg Met Arg Ala Ser Val Gly Gly Ala Ile Thr
                    675                 680                 685
Ala Gly Ile Asp Cys Asp Ser Ala Ser Thr Ser Ala Ala Ala Ala Ala
                    690                 695                 700
Ala Gln His Gln Pro Gln Pro Gln Pro Gln Pro Gln Pro Ser Ser Leu
705                 710                 715                 720
Thr Gln Asn Asp Ser Gln His Gln Thr Gln Pro Gln Leu Gln Pro Gln
                    725                 730                 735
Leu Pro Pro Gln Leu Gln Gly Gln Leu Gln Pro Gln Leu Gln Pro Gln
                    740                 745                 750
Leu Gln Thr Gln Leu Gln Pro Gln Ile Gln Pro Gln Pro Gln Leu Leu
                    755                 760                 765
Pro Val Ser Ala Pro Val Pro Ala Ser Val Thr Ala Pro Gly Ser Leu
                    770                 775                 780
Ser Ala Val Ser Thr Ser Ser Glu Tyr Met Gly Gly Ser Ala Ala Ile
785                 790                 795                 800
Gly Pro Ile Thr Pro Ala Thr Thr Ser Ser Ile Thr Ala Ala Val Thr
                    805                 810                 815
Ala Ser Ser Thr Thr Ser Ala Val Pro Met Gly Asn Gly Val Gly Val
                    820                 825                 830
```

Gly Val Gly Val Gly Asn Val Ser Met Tyr Ala Asn Ala Gln Thr
            835                 840                 845

Ala Met Ala Leu Met Gly Val Ala Leu His Ser His Gln Glu Gln Leu
        850                 855                 860

Ile Gly Val Ala Val Lys Ser Glu His Ser Thr Thr Ala
865                 870                 875

<210> SEQ ID NO 33
<211> LENGTH: 1282
<212> TYPE: DNA
<213> ORGANISM: Amblyomma americanum

<400> SEQUENCE: 33

```
cggcggaagt gccaggagtg ccggctcaag aagtgcctgg ccgtcgggat gcggccggag    60
tgcgtcgtgc cggagaacca gtgcgccatc aagcggaagg agaagaaagc ccagaaggag   120
aaggacaagg tgcaaacgaa cgccaccgtc agtacaacga acagcaccta ccggtcggag   180
atactgccga tcctgatgaa atgtgatcca ccgccgcacc aagcgatacc tctactaccg   240
gaaaagctcc tgcaggagaa taggctaaga aacatacctc tactgacggc gaaccaaatg   300
gccgtcattt acaaactcat ctggtaccag gacgggtacg agcaaccctc ggaggaagat   360
ctcaaacgga taatgatcgg ttcacccaac gaggaggaag atcaacatga cgtgcacttc   420
cggcacataa cggaaatcac aatcctaaca gtacaactaa tcgtggagtt cgccaaggga   480
ctgccagcat ttaccaagat tccacaggag gaccagatca cgctgctgaa ggcctgctca   540
agcgaggtta tgatgttgcg aatggcccgc cgctacgacg ctgccaccga ttcgatcctg   600
ttcgcgaaca accggtccta cacgagggac tcctaccgga tggccggcat ggcggacacg   660
atagaggacc tgctgcactt ctgccggcag atgttctccc tcacggtaga caacgtcgag   720
tacgcactcc tcacggcgat agtcatcttc tcggatcggc ccggactgga gcaagccgaa   780
ctggtcgagc acatccagag ctactacatc gacacgctgc ggatctacat cctgaatagg   840
cacgcgggcg atccgaagtg cagtgtgata ttcgccaaac tgctgtcgat cctgacggag   900
ctccgaacgc tgggcaacca gaactcggag atgtgcttct cgctcaagct gaagaaccgc   960
aaactgccac ggttcctgga ggagatctgg gacgtccagg acataccgcc ctcgatgcag  1020
gcccagatgc acagccatgg cacccagtcc tcgtcctcat cgtcctccag tagtagtagt  1080
agtagtaacg gtagtagtaa cggtaacagt agtagtaata gtaatagttc acagcacggg  1140
ccacatccgc atccgcacgg gcagcaatta acgccaaatc agcagcagca tcagcagcag  1200
cacagtcagt tacagcaagt tcacgccaac ggcagcggaa gtggtggcgg cagtaacaat  1260
aatagcagta gtgggggcgt ag                                           1282
```

<210> SEQ ID NO 34
<211> LENGTH: 560
<212> TYPE: PRT
<213> ORGANISM: Amblyomma americanum

<400> SEQUENCE: 34

Met Leu Ser Glu Leu Gln Leu Gln Pro Leu Gly Arg Arg Ser Ala Ala
1               5                   10                  15

Ala Ala Pro Ser Ser Asp Glu Val Ala Ser Met Lys Pro Met Leu Leu
            20                  25                  30

Gln Ala Ala Gln Gly Gly Ala Gly Gly Leu Ala Ala Gly Ser Pro Pro
        35                  40                  45

```
Ala Leu Ser Pro Asn Leu Pro Ser Val Val Lys Val Glu Pro Arg Leu
     50                  55                  60

Pro Ser Pro Cys Val Gly Gly Ala Ala Ser Gly Asp Gly Gly Pro Val
 65              70                  75                      80

Pro Pro Lys Arg Val Arg Gln Asp Asp Ala Gly Ala Trp Ile Ser Ser
                 85                  90                  95

Pro Ser Ser Gln Met Ser Val Gly Ser Leu Ser Pro Pro Pro Pro Leu
            100                 105                 110

Leu Asn Gly Val Ala Asn Ser Ser Gly Leu Ser Pro Val Ser Asn Cys
            115                 120                 125

Ser Ser Tyr Asp Thr Tyr Ser Pro Arg Gly Pro Cys Lys Glu Glu Met
        130                 135                 140

Ser Pro Ser Ser Gly Gly Gly Leu Asn Gly Tyr Phe Val Asp Ser
145                 150                 155                 160

Phe Gly Asp Pro Lys Lys Lys Gly Pro Ala Pro Arg Gln Gln Glu
                165                 170                 175

Glu Leu Cys Leu Val Cys Gly Asp Arg Ala Ser Gly Tyr His Tyr Asn
            180                 185                 190

Ala Leu Thr Cys Glu Gly Cys Lys Gly Phe Phe Arg Arg Ser Ile Thr
        195                 200                 205

Lys Asn Ala Val Tyr Gln Cys Lys Tyr Gly Asn Asn Cys Asp Ile Asp
210                 215                 220

Met Tyr Met Arg Arg Lys Cys Gln Glu Cys Arg Leu Lys Lys Cys Leu
225                 230                 235                 240

Ser Val Gly Met Arg Pro Glu Cys Val Val Pro Glu Tyr Gln Cys Ala
                245                 250                 255

Ile Lys Arg Glu Ser Lys Lys His Gln Lys Asp Arg Pro Asn Ser Thr
            260                 265                 270

Thr Arg Glu Ser Pro Ser Ala Leu Met Ala Pro Ser Ser Val Gly Gly
        275                 280                 285

Val Ser Pro Thr Ser Gln Pro Met Gly Gly Gly Ser Ser Leu Gly
    290                 295                 300

Ser Ser Asn His Glu Glu Asp Lys Lys Pro Val Val Leu Ser Pro Gly
305                 310                 315                 320

Val Lys Pro Leu Ser Ser Ser Gln Glu Asp Leu Ile Asn Lys Leu Val
                325                 330                 335

Tyr Tyr Gln Gln Glu Phe Glu Ser Pro Ser Glu Glu Asp Met Lys Lys
            340                 345                 350

Thr Thr Pro Phe Pro Leu Gly Asp Ser Glu Glu Asp Asn Gln Arg Arg
        355                 360                 365

Phe Gln His Ile Thr Glu Ile Thr Ile Leu Thr Val Gln Leu Ile Val
370                 375                 380

Glu Phe Ser Lys Arg Val Pro Gly Phe Asp Thr Leu Ala Arg Glu Asp
385                 390                 395                 400

Gln Ile Thr Leu Leu Lys Ala Cys Ser Ser Glu Val Met Met Leu Arg
                405                 410                 415

Gly Ala Arg Lys Tyr Asp Val Lys Thr Asp Ser Ile Val Phe Ala Asn
            420                 425                 430

Asn Gln Pro Tyr Thr Arg Asp Asn Tyr Arg Ser Ala Ser Val Gly Asp
        435                 440                 445

Ser Ala Asp Ala Leu Phe Arg Phe Cys Arg Lys Met Cys Gln Leu Arg
450                 455                 460

Val Asp Asn Ala Glu Tyr Ala Leu Leu Thr Ala Ile Val Ile Phe Ser
```

```
465                 470                 475                 480
Glu Arg Pro Ser Leu Val Asp Pro His Lys Val Glu Arg Ile Gln Glu
                485                 490                 495
Tyr Tyr Ile Glu Thr Leu Arg Met Tyr Ser Glu Asn His Arg Pro Pro
            500                 505                 510
Gly Lys Asn Tyr Phe Ala Arg Leu Leu Ser Ile Leu Thr Glu Leu Arg
        515                 520                 525
Thr Leu Gly Asn Met Asn Ala Glu Met Cys Phe Ser Leu Lys Val Gln
    530                 535                 540
Asn Lys Lys Leu Pro Pro Phe Leu Ala Glu Ile Trp Asp Ile Gln Glu
545                 550                 555                 560
```

<210> SEQ ID NO 35
<211> LENGTH: 40
<212> TYPE: DNA
<213> ORGANISM: Artificial Sequence
<220> FEATURE:
<223> OTHER INFORMATION: PCR primer

<400> SEQUENCE: 35
gtaccaggac gggtacgcgc agccttctga tgaagatttg        40

<210> SEQ ID NO 36
<211> LENGTH: 40
<212> TYPE: DNA
<213> ORGANISM: Artificial Sequence
<220> FEATURE:
<223> OTHER INFORMATION: PCR primer

<400> SEQUENCE: 36
caaatcttca tcagaaggct gcgcgtaccc gtcctggtac        40

<210> SEQ ID NO 37
<211> LENGTH: 37
<212> TYPE: DNA
<213> ORGANISM: Artificial Sequence
<220> FEATURE:
<223> OTHER INFORMATION: PCR primer

<400> SEQUENCE: 37
ccaggacggg tacgaggcgc cttctgatga agatttg        37

<210> SEQ ID NO 38
<211> LENGTH: 37
<212> TYPE: DNA
<213> ORGANISM: Artificial Sequence
<220> FEATURE:
<223> OTHER INFORMATION: PCR primer

<400> SEQUENCE: 38
caaatcttca tcagaaggcg cctcgtaccc gtcctgg        37

<210> SEQ ID NO 39
<211> LENGTH: 31
<212> TYPE: DNA
<213> ORGANISM: Artificial Sequence
<220> FEATURE:
<223> OTHER INFORMATION: PCR primer

<400> SEQUENCE: 39
gagtctgaca ctcccgcccg ccagatcaca g        31

<210> SEQ ID NO 40

```
<211> LENGTH: 31
<212> TYPE: DNA
<213> ORGANISM: Artificial Sequence
<220> FEATURE:
<223> OTHER INFORMATION: PCR primer

<400> SEQUENCE: 40
ctgtgatctg gcgggcggga gtgtcagact c                           31

<210> SEQ ID NO 41
<211> LENGTH: 30
<212> TYPE: DNA
<213> ORGANISM: Artificial Sequence
<220> FEATURE:
<223> OTHER INFORMATION: PCR primer

<400> SEQUENCE: 41
cactcccttc cgccaggcca cagagatgac                             30

<210> SEQ ID NO 42
<211> LENGTH: 30
<212> TYPE: DNA
<213> ORGANISM: Artificial Sequence
<220> FEATURE:
<223> OTHER INFORMATION: PCR primer

<400> SEQUENCE: 42
gtcatctctg tggcctggcg aagggagtg                              30

<210> SEQ ID NO 43
<211> LENGTH: 30
<212> TYPE: DNA
<213> ORGANISM: Artificial Sequence
<220> FEATURE:
<223> OTHER INFORMATION: PCR primer

<400> SEQUENCE: 43
cactcccttc cgccagatcg cagagatgac                             30

<210> SEQ ID NO 44
<211> LENGTH: 30
<212> TYPE: DNA
<213> ORGANISM: Artificial Sequence
<220> FEATURE:
<223> OTHER INFORMATION: PCR primer

<400> SEQUENCE: 44
gtcatctctg cgatctggcg aagggagtg                              30

<210> SEQ ID NO 45
<211> LENGTH: 34
<212> TYPE: DNA
<213> ORGANISM: Artificial Sequence
<220> FEATURE:
<223> OTHER INFORMATION: PCR primer

<400> SEQUENCE: 45
cgccagatca cagagatggc tatcctcacg gtcc                        34

<210> SEQ ID NO 46
<211> LENGTH: 34
<212> TYPE: DNA
<213> ORGANISM: Artificial Sequence
<220> FEATURE:
<223> OTHER INFORMATION: PCR primer

<400> SEQUENCE: 46
```
ggaccgtgag gatagccatc tctgtgatct ggcg                              34

<210> SEQ ID NO 47
<211> LENGTH: 33
<212> TYPE: DNA
<213> ORGANISM: Artificial Sequence
<220> FEATURE:
<223> OTHER INFORMATION: PCR primer

<400> SEQUENCE: 47
gagatgacta tcctcgcggt ccaacttatc gtg                               33

<210> SEQ ID NO 48
<211> LENGTH: 33
<212> TYPE: DNA
<213> ORGANISM: Artificial Sequence
<220> FEATURE:
<223> OTHER INFORMATION: PCR primer

<400> SEQUENCE: 48
cacgataagt tggaccgcga ggatagtcat ctc                               33

<210> SEQ ID NO 49
<211> LENGTH: 32
<212> TYPE: DNA
<213> ORGANISM: Artificial Sequence
<220> FEATURE:
<223> OTHER INFORMATION: PCR primer

<400> SEQUENCE: 49
gatgactatc ctcacggccc aacttatcgt gg                                32

<210> SEQ ID NO 50
<211> LENGTH: 32
<212> TYPE: DNA
<213> ORGANISM: Artificial Sequence
<220> FEATURE:
<223> OTHER INFORMATION: PCR primer

<400> SEQUENCE: 50
ccacgataag ttgggccgtg aggatagtca tc                                32

<210> SEQ ID NO 51
<211> LENGTH: 35
<212> TYPE: DNA
<213> ORGANISM: Artificial Sequence
<220> FEATURE:
<223> OTHER INFORMATION: PCR primer

<400> SEQUENCE: 51
ctatcctcac ggtccaagct atcgtggagt tcgcg                             35

<210> SEQ ID NO 52
<211> LENGTH: 35
<212> TYPE: DNA
<213> ORGANISM: Artificial Sequence
<220> FEATURE:
<223> OTHER INFORMATION: PCR primer

<400> SEQUENCE: 52
cgcgaactcc acgatagctt ggaccgtgag gatag                             35

<210> SEQ ID NO 53
<211> LENGTH: 35
<212> TYPE: DNA

```
<213> ORGANISM: Artificial Sequence
<220> FEATURE:
<223> OTHER INFORMATION: PCR primer

<400> SEQUENCE: 53
ctatcctcac ggtccaactt gccgtggagt tcgcg                              35

<210> SEQ ID NO 54
<211> LENGTH: 35
<212> TYPE: DNA
<213> ORGANISM: Artificial Sequence
<220> FEATURE:
<223> OTHER INFORMATION: PCR primer

<400> SEQUENCE: 54
cgcgaactcc acggcaagtt ggaccgtgag gatag                              35

<210> SEQ ID NO 55
<211> LENGTH: 31
<212> TYPE: DNA
<213> ORGANISM: Artificial Sequence
<220> FEATURE:
<223> OTHER INFORMATION: PCR primer

<400> SEQUENCE: 55
gctcaagtga ggtagcgatg ctccgagtcg c                                  31

<210> SEQ ID NO 56
<211> LENGTH: 31
<212> TYPE: DNA
<213> ORGANISM: Artificial Sequence
<220> FEATURE:
<223> OTHER INFORMATION: PCR primer

<400> SEQUENCE: 56
gcgactcgga gcatcgctac ctcacttgag c                                  31

<210> SEQ ID NO 57
<211> LENGTH: 31
<212> TYPE: DNA
<213> ORGANISM: Artificial Sequence
<220> FEATURE:
<223> OTHER INFORMATION: PCR primer

<400> SEQUENCE: 57
gctcaagtga ggtaatggcg ctccgagtcg c                                  31

<210> SEQ ID NO 58
<211> LENGTH: 31
<212> TYPE: DNA
<213> ORGANISM: Artificial Sequence
<220> FEATURE:
<223> OTHER INFORMATION: PCR primer

<400> SEQUENCE: 58
gcgactcgga gcgccattac ctcacttgag c                                  31

<210> SEQ ID NO 59
<211> LENGTH: 30
<212> TYPE: DNA
<213> ORGANISM: Artificial Sequence
<220> FEATURE:
<223> OTHER INFORMATION: PCR primer

<400> SEQUENCE: 59
gtaatgatgc tccgagccgc gcgacgatac                                    30
```

<210> SEQ ID NO 60
<211> LENGTH: 30
<212> TYPE: DNA
<213> ORGANISM: Artificial Sequence
<220> FEATURE:
<223> OTHER INFORMATION: PCR primer

<400> SEQUENCE: 60
gtatcgtcgc gcggctcgga gcatcattac                                    30

<210> SEQ ID NO 61
<211> LENGTH: 36
<212> TYPE: DNA
<213> ORGANISM: Artificial Sequence
<220> FEATURE:
<223> OTHER INFORMATION: PCR primer

<400> SEQUENCE: 61
gtgaggtaat gatgctcgca gtcgcgcgac gatacg                             36

<210> SEQ ID NO 62
<211> LENGTH: 36
<212> TYPE: DNA
<213> ORGANISM: Artificial Sequence
<220> FEATURE:
<223> OTHER INFORMATION: PCR primer

<400> SEQUENCE: 62
cgtatcgtcg cgcgactgcg agcatcatta cctcac                             36

<210> SEQ ID NO 63
<211> LENGTH: 32
<212> TYPE: DNA
<213> ORGANISM: Artificial Sequence
<220> FEATURE:
<223> OTHER INFORMATION: PCR primer

<400> SEQUENCE: 63
cagacagtgt tctggccgcg aacaaccaag cg                                 32

<210> SEQ ID NO 64
<211> LENGTH: 32
<212> TYPE: DNA
<213> ORGANISM: Artificial Sequence
<220> FEATURE:
<223> OTHER INFORMATION: PCR primer

<400> SEQUENCE: 64
cgcttggttg ttcgcggcca gaacactgtc tg                                 32

<210> SEQ ID NO 65
<211> LENGTH: 33
<212> TYPE: DNA
<213> ORGANISM: Artificial Sequence
<220> FEATURE:
<223> OTHER INFORMATION: PCR primer

<400> SEQUENCE: 65
tcagacagtg ttctggccgc gaacaaccaa gcg                                33

<210> SEQ ID NO 66
<211> LENGTH: 33
<212> TYPE: DNA
<213> ORGANISM: Artificial Sequence
<220> FEATURE:

<223> OTHER INFORMATION: PCR primer

<400> SEQUENCE: 66
cgcttggttg ttcgcggcca gaacactgtc tga                33

<210> SEQ ID NO 67
<211> LENGTH: 32
<212> TYPE: DNA
<213> ORGANISM: Artificial Sequence
<220> FEATURE:
<223> OTHER INFORMATION: PCR primer

<400> SEQUENCE: 67
cagacagtgt tctgttcccg aacaaccaag cg                 32

<210> SEQ ID NO 68
<211> LENGTH: 32
<212> TYPE: DNA
<213> ORGANISM: Artificial Sequence
<220> FEATURE:
<223> OTHER INFORMATION: PCR primer

<400> SEQUENCE: 68
cgcttggttg ttcgggaaca gaacactgtc tg                 32

<210> SEQ ID NO 69
<211> LENGTH: 31
<212> TYPE: DNA
<213> ORGANISM: Artificial Sequence
<220> FEATURE:
<223> OTHER INFORMATION: PCR primer

<400> SEQUENCE: 69
cactcgcgac aacgcccgca aggctggcat g                  31

<210> SEQ ID NO 70
<211> LENGTH: 31
<212> TYPE: DNA
<213> ORGANISM: Artificial Sequence
<220> FEATURE:
<223> OTHER INFORMATION: PCR primer

<400> SEQUENCE: 70
catgccagcc ttgcgggcgt tgtcgcgagt g                  31

<210> SEQ ID NO 71
<211> LENGTH: 34
<212> TYPE: DNA
<213> ORGANISM: Artificial Sequence
<220> FEATURE:
<223> OTHER INFORMATION: PCR primer

<400> SEQUENCE: 71
cgacaactac cgcaagtttg gcatggccta cgtc               34

<210> SEQ ID NO 72
<211> LENGTH: 34
<212> TYPE: DNA
<213> ORGANISM: Artificial Sequence
<220> FEATURE:
<223> OTHER INFORMATION: PCR primer

<400> SEQUENCE: 72
gacgtaggcc atgccaaact tgcggtagtt gtcg               34

```
<210> SEQ ID NO 73
<211> LENGTH: 31
<212> TYPE: DNA
<213> ORGANISM: Artificial Sequence
<220> FEATURE:
<223> OTHER INFORMATION: PCR primer

<400> SEQUENCE: 73
ctaccgcaag gctggcgcgg cctacgtcat c                                 31

<210> SEQ ID NO 74
<211> LENGTH: 31
<212> TYPE: DNA
<213> ORGANISM: Artificial Sequence
<220> FEATURE:
<223> OTHER INFORMATION: PCR primer

<400> SEQUENCE: 74
gatgacgtag gccgcgccag ccttgcggta g                                 31

<210> SEQ ID NO 75
<211> LENGTH: 32
<212> TYPE: DNA
<213> ORGANISM: Artificial Sequence
<220> FEATURE:
<223> OTHER INFORMATION: PCR primer

<400> SEQUENCE: 75
gctcaagaac agaaaggcgc cgcctttcct cg                                32

<210> SEQ ID NO 76
<211> LENGTH: 32
<212> TYPE: DNA
<213> ORGANISM: Artificial Sequence
<220> FEATURE:
<223> OTHER INFORMATION: PCR primer

<400> SEQUENCE: 76
cgaggaaagg cggcgccttt ctgttcttga gc                                32

<210> SEQ ID NO 77
<211> LENGTH: 36
<212> TYPE: DNA
<213> ORGANISM: Artificial Sequence
<220> FEATURE:
<223> OTHER INFORMATION: PCR primer

<400> SEQUENCE: 77
ctccaacatg tgcatctccg ccaagctcaa gaacag                            36

<210> SEQ ID NO 78
<211> LENGTH: 36
<212> TYPE: DNA
<213> ORGANISM: Artificial Sequence
<220> FEATURE:
<223> OTHER INFORMATION: PCR primer

<400> SEQUENCE: 78
ctgttcttga gcttggcgga gatgcacatg ttggag                            36

<210> SEQ ID NO 79
<211> LENGTH: 31
<212> TYPE: DNA
<213> ORGANISM: Artificial Sequence
<220> FEATURE:
<223> OTHER INFORMATION: PCR primer
```

<400> SEQUENCE: 79
gaaagctgcc gcctttcgcc gaggagatct g                                    31

<210> SEQ ID NO 80
<211> LENGTH: 31
<212> TYPE: DNA
<213> ORGANISM: Artificial Sequence
<220> FEATURE:
<223> OTHER INFORMATION: PCR primer

<400> SEQUENCE: 80
cagatctcct cggcgaaagg cggcagcttt c                                    31

<210> SEQ ID NO 81
<211> LENGTH: 31
<212> TYPE: DNA
<213> ORGANISM: Artificial Sequence
<220> FEATURE:
<223> OTHER INFORMATION: PCR primer

<400> SEQUENCE: 81
ctttcctcga ggagatcgcg gatgtggcag g                                    31

<210> SEQ ID NO 82
<211> LENGTH: 31
<212> TYPE: DNA
<213> ORGANISM: Artificial Sequence
<220> FEATURE:
<223> OTHER INFORMATION: PCR primer

<400> SEQUENCE: 82
cctgccacat ccgcgatctc ctcgaggaaa g                                    31

<210> SEQ ID NO 83
<211> LENGTH: 32
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (18)..(18)
<223> OTHER INFORMATION: "n" is a, t, g, or c

<400> SEQUENCE: 83
cagacagtgt tctgttgncg aacaaccaag cg                                   32

<210> SEQ ID NO 84
<211> LENGTH: 32
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (15)..(15)
<223> OTHER INFORMATION: "n" is a, t, g, or c

<400> SEQUENCE: 84
cgcttggttg ttcgncaaca gaacactgtc tg                                   32

<210> SEQ ID NO 85
<211> LENGTH: 32
<212> TYPE: DNA
<213> ORGANISM: Artificial Sequence
<220> FEATURE:
<223> OTHER INFORMATION: Degenerate PCR primer

```
<220> FEATURE:
<221> NAME/KEY: misc_feature
<222> LOCATION: (18)..(19)
<223> OTHER INFORMATION: "n" is a, t, g, or c

<400> SEQUENCE: 85
cagacagtgt tctgttgnng aacaaccaag cg                          32

<210> SEQ ID NO 86
<211> LENGTH: 32
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (14)..(15)
<223> OTHER INFORMATION: "n" is a, t, g, or c

<400> SEQUENCE: 86
cgcttggttg ttcnncaaca gaacactgtc tg                          32

<210> SEQ ID NO 87
<211> LENGTH: 40
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (20)..(22)
<223> OTHER INFORMATION: "n" is a, t, g, or c

<400> SEQUENCE: 87
cactcccttc cgccagatcn nngagatgac tatcctcacg                  40

<210> SEQ ID NO 88
<211> LENGTH: 39
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (19)..(21)
<223> OTHER INFORMATION: "n" is a, t, g, or c

<400> SEQUENCE: 88
cgtgaggata gtcatctcnn ngatctggcg gaagggagt                   39

<210> SEQ ID NO 89
<211> LENGTH: 38
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (16)..(18)
<223> OTHER INFORMATION: "n" is a, t, g, or c

<400> SEQUENCE: 89
gtaatgatgc tccgannngc gcgacgatac gatgcggc                    38

<210> SEQ ID NO 90
<211> LENGTH: 38
<212> TYPE: DNA
<213> ORGANISM: Artificial Sequence
<220> FEATURE:
```

<223> OTHER INFORMATION: Degenerate PCR primer
<220> FEATURE:
<221> NAME/KEY: misc_feature
<222> LOCATION: (21)..(23)
<223> OTHER INFORMATION: "n" is a, t, g, or c

<400> SEQUENCE: 90
gccgcatcgt atcgtcgcgc nnntcggagc atcattac                                38

<210> SEQ ID NO 91
<211> LENGTH: 38
<212> TYPE: DNA
<213> ORGANISM: Artificial Sequence
<220> FEATURE:
<223> OTHER INFORMATION: PCR primer

<400> SEQUENCE: 91
tcggactcaa tattcttccc gaataataga tcatatac                                38

<210> SEQ ID NO 92
<211> LENGTH: 38
<212> TYPE: DNA
<213> ORGANISM: Artificial Sequence
<220> FEATURE:
<223> OTHER INFORMATION: PCR primer

<400> SEQUENCE: 92
gtatatgatc tattattcgg gaagaatatt gagtccga                                38

<210> SEQ ID NO 93
<211> LENGTH: 34
<212> TYPE: DNA
<213> ORGANISM: Artificial Sequence
<220> FEATURE:
<223> OTHER INFORMATION: PCR primer

<400> SEQUENCE: 93
tcttacaaaa tggcccgaat ggctgataac attg                                    34

<210> SEQ ID NO 94
<211> LENGTH: 34
<212> TYPE: DNA
<213> ORGANISM: Artificial Sequence
<220> FEATURE:
<223> OTHER INFORMATION: PCR primer

<400> SEQUENCE: 94
caatgttatc agccattcgg gccattttgt aaga                                    34

<210> SEQ ID NO 95
<211> LENGTH: 34
<212> TYPE: DNA
<213> ORGANISM: Artificial Sequence
<220> FEATURE:
<223> OTHER INFORMATION: PCR primer

<400> SEQUENCE: 95
tcttacaaaa tggccctaat ggctgataac attg                                    34

<210> SEQ ID NO 96
<211> LENGTH: 34
<212> TYPE: DNA
<213> ORGANISM: Artificial Sequence
<220> FEATURE:
<223> OTHER INFORMATION: PCR primer

<400> SEQUENCE: 96
caatgttatc agccattagg gccattttgt aaga   34

<210> SEQ ID NO 97
<211> LENGTH: 33
<212> TYPE: DNA
<213> ORGANISM: Artificial Sequence
<220> FEATURE:
<223> OTHER INFORMATION: PCR primer

<400> SEQUENCE: 97
acgctgggca accaggccgc cgagatgtgt ttc   33

<210> SEQ ID NO 98
<211> LENGTH: 33
<212> TYPE: DNA
<213> ORGANISM: Artificial Sequence
<220> FEATURE:
<223> OTHER INFORMATION: PCR primer

<400> SEQUENCE: 98
gaaacacatc tcggcggcct ggttgcccag cgt   33

<210> SEQ ID NO 99
<211> LENGTH: 33
<212> TYPE: DNA
<213> ORGANISM: Artificial Sequence
<220> FEATURE:
<223> OTHER INFORMATION: PCR primer

<400> SEQUENCE: 99
cagaacgccg agatggcttt ctcactaaag ctc   33

<210> SEQ ID NO 100
<211> LENGTH: 33
<212> TYPE: DNA
<213> ORGANISM: Artificial Sequence
<220> FEATURE:
<223> OTHER INFORMATION: PCR primer

<400> SEQUENCE: 100
gagctttagt gagaaagcca tctcggcgtt ctg   33

<210> SEQ ID NO 101
<211> LENGTH: 33
<212> TYPE: DNA
<213> ORGANISM: Artificial Sequence
<220> FEATURE:
<223> OTHER INFORMATION: PCR primer

<400> SEQUENCE: 101
cagaacgccg agatgtcttt ctcactaaag ctc   33

<210> SEQ ID NO 102
<211> LENGTH: 33
<212> TYPE: DNA
<213> ORGANISM: Artificial Sequence
<220> FEATURE:
<223> OTHER INFORMATION: PCR primer

<400> SEQUENCE: 102
gagctttagt gagaaagaca tctcggcgtt ctg   33

<210> SEQ ID NO 103
<211> LENGTH: 34
<212> TYPE: DNA

<213> ORGANISM: Artificial Sequence
<220> FEATURE:
<223> OTHER INFORMATION: PCR primer

<400> SEQUENCE: 103
gtgatgatgc tgagagctgc ccggaaatat gatg                                 34

<210> SEQ ID NO 104
<211> LENGTH: 34
<212> TYPE: DNA
<213> ORGANISM: Artificial Sequence
<220> FEATURE:
<223> OTHER INFORMATION: PCR primer

<400> SEQUENCE: 104
catcatattt ccgggcagct ctcagcatca tcac                                 34

<210> SEQ ID NO 105
<211> LENGTH: 38
<212> TYPE: DNA
<213> ORGANISM: Artificial Sequence
<220> FEATURE:
<223> OTHER INFORMATION: PCR primer

<400> SEQUENCE: 105
acagattcta tagtgtttcc caataaccag ccgtacac                             38

<210> SEQ ID NO 106
<211> LENGTH: 38
<212> TYPE: DNA
<213> ORGANISM: Artificial Sequence
<220> FEATURE:
<223> OTHER INFORMATION: PCR primer

<400> SEQUENCE: 106
gtgtacggct ggttattggg aaacactata gaatctgt                             38

<210> SEQ ID NO 107
<211> LENGTH: 30
<212> TYPE: DNA
<213> ORGANISM: Artificial Sequence
<220> FEATURE:
<223> OTHER INFORMATION: primer

<400> SEQUENCE: 107
gcggcctcag acagtattct gttcgcgaac                                      30

<210> SEQ ID NO 108
<211> LENGTH: 38
<212> TYPE: DNA
<213> ORGANISM: Artificial Sequence
<220> FEATURE:
<223> OTHER INFORMATION: primer

<400> SEQUENCE: 108
ggtggaagaa atccaggagt actacctgaa tacgctcc                             38

<210> SEQ ID NO 109
<211> LENGTH: 29
<212> TYPE: DNA
<213> ORGANISM: Artificial Sequence
<220> FEATURE:
<223> OTHER INFORMATION: primer

<400> SEQUENCE: 109
caaggctggc atggccgagg tcatcgagg                                       29

<210> SEQ ID NO 110
<211> LENGTH: 35
<212> TYPE: DNA
<213> ORGANISM: Artificial Sequence
<220> FEATURE:
<223> OTHER INFORMATION: primer

<400> SEQUENCE: 110
cccttccgcc agatcgtaga gatgactatc ctcac                                35

<210> SEQ ID NO 111
<211> LENGTH: 32
<212> TYPE: DNA
<213> ORGANISM: Artificial Sequence
<220> FEATURE:
<223> OTHER INFORMATION: primer

<400> SEQUENCE: 111
ggtaatgatg ctccgaaccg cgcgacgata cg                                   32

<210> SEQ ID NO 112
<211> LENGTH: 1586
<212> TYPE: DNA
<213> ORGANISM: Bamecia argentifoli

<400> SEQUENCE: 112
gaattcgcgg ccgctcgcaa acttccgtac ctctcacccc ctcgccagga cccccgcca      60 accagttcac cgtcatctcc tccaatggat actcatcccc catgtcttcg ggcagctacg    120
acccttatag tcccaccaat ggaagaatag ggaaagaaga gctttcgccg gcgaatagtc    180
tgaacgggta caacgtggat agctgcgatg cgtcgcggaa gaagaaggga ggaacgggtc    240
ggcagcagga ggagctgtgt ctcgtctgcg gggaccgcgc ctccggctac cactacaacg    300
ccctcacctg cgaaggctgc aagggcttct tccgtcggag catcaccaag aatgccgtct    360
accagtgtaa atatggaaat aattgtgaaa ttgacatgta catgaggcga aaatgccaag    420
agtgtcgtct caagaagtgt ctcagcgttg gcatgaggcc agaatgtgta gttcccgaat    480
tccagtgtgc tgtgaagcga aaagagaaaa aagcgcaaaa ggacaaagat aaacctaact    540
caacgacgag ttgttctcca gatggaatca aacaagagat agatcctcaa aggctggata    600
cagattcgca gctattgtct gtaaatggag ttaaacccat tactccagag caagaagagc    660
tcatccatag gctagtttat tttcaaaatg aatatgaaca tccatcccca gaggatatca    720
aaaggatagt taatgctgca ccagaagaag aaaatgtagc tgaagaaagg tttaggcata    780
ttacagaaat tacaattctc actgtacagt taattgtgga attttctaag cgattacctg    840
gttttgacaa actaattcgt gaagatcaaa tagctttatt aaaggcatgt agtagtgaag    900
taatgatgtt tagaatggca aggaggtatg atgctgaaac agattcgata ttgtttgcaa    960
ctaaccagcc gtatacgaga gaatcataca ctgtagctgg catgggtgat actgtggagg   1020
atctgctccg attttgtcga catatgtgtg ccatgaaagt cgataacgca gaatatgctc   1080
ttctcactgc cattgtaatt tttttcagaac gaccatctct aagtgaaggc tggaaggttg   1140
agaagattca agaaatttac atagaagcat taaaagcata tgttgaaaat cgaaggaaac   1200
catatgcaac aaccattttt gctaagttac tatctgtttt aactgaacta cgaacattag   1260
ggaatatgaa ttcagaaaca tgcttctcat tgaagctgaa gaatagaaag gtgccatcct   1320
tcctcgagga gatttgggat gttgtttcat aaacagtctt acctcaattc catgttactt   1380

| | |
|---|---|
| ttcatatttg atttatctca gcaggtggct cagtacttat cctcacatta ctgagctcac | 1440 |
| ggtatgctca tacaattata acttgtaata tcatatcggt gatgacaaat ttgttacaat | 1500 |
| attctttgtt accttaacac aatgttgatc tcataatgat gtatgaattt ttctgttttt | 1560 |
| gcaaaaaaaa aagcggccgc gaattc | 1586 |

```
<210> SEQ ID NO 113
<211> LENGTH: 1109
<212> TYPE: DNA
<213> ORGANISM: Nephotetix cincticeps

<400> SEQUENCE: 113
```

| | |
|---|---|
| caggaggagc tctgcctgtt gtgcggagac cgagcgtcgg gataccacta caacgctctc | 60 |
| acctgcgaag gatgcaaggg cttctttcgg aggagtatca ccaaaaacgc agtgtaccag | 120 |
| tccaaatacg gcaccaattg tgaaatagac atgtatatgc ggcgcaagtg ccaggagtgc | 180 |
| cgactcaaga agtgcctcag tgtagggatg aggccagaat gtgtagtacc tgagtatcaa | 240 |
| tgtgccgtaa aaggaaaga gaaaaagct caaaaggaca agataaaacc tgtctcttca | 300 |
| accaatggct cgcctgaaat gagaatagac caggacaacc gttgtgtggt gttgcagagt | 360 |
| gaagacaaca ggtacaactc gagtacgccc agtttcggag tcaaacccct cagtccagaa | 420 |
| caagaggagc tcatccacag gctcgtctac ttccagaacg agtacgaaca ccctgccgag | 480 |
| gaggatctca gcggatcga gaacctcccc tgtgacgacg atgacccgtg tgatgttcgc | 540 |
| tacaaacaca ttacggagat cacaatactc acagtccagc tcatcgtgga gtttgcgaaa | 600 |
| aaactgcctg gtttcgacaa actactgaga gaggaccaga tcgtgttgct caaggcgtgt | 660 |
| tcgagcgagg tgatgatgct gcggatggcg cggaggtacg acgtccagac agactcgatc | 720 |
| ctgttcgcca acaaccagcc gtacacgcga gagtcgtaca cgatggcagg cgtgggggaa | 780 |
| gtcatcgaag atctgctgcg gttcggccga ctcatgtgct ccatgaaggt ggacaatgcc | 840 |
| gagtatgctc tgctcacggc catcgtcatc ttctccgagc ggccgaacct ggcggaagga | 900 |
| tggaaggttg agaagatcca ggagatctac ctggaggcgc tcaagtccta cgtggacaac | 960 |
| cgagtgaaac ctcgcagtcc gaccatcttc gccaaactgc tctccgttct caccgagctg | 1020 |
| cgaacactcg gcaaccagaa ctccgagatg tgcttctcgt taaactacgc aaccgcaaac | 1080 |
| atgccaccgt tcctcgaaga aatctggga | 1109 |

```
<210> SEQ ID NO 114
<211> LENGTH: 4
<212> TYPE: PRT
<213> ORGANISM: Artificial sequence
<220> FEATURE:
<223> OTHER INFORMATION: Response Element

<400> SEQUENCE: 114

Arg Arg Gly Gly
1

<210> SEQ ID NO 115
<211> LENGTH: 9
<212> TYPE: DNA
<213> ORGANISM: Artificial sequence
<220> FEATURE:
<223> OTHER INFORMATION: Response Element
<220> FEATURE:
<221> NAME/KEY: misc_feature
<222> LOCATION: (5)..(5)
<223> OTHER INFORMATION: n is a, c, g, or t
```

```
<400> SEQUENCE: 115 ttcantgac                                                                9

<210> SEQ ID NO 116
<211> LENGTH: 4
<212> TYPE: PRT
<213> ORGANISM: Artificial sequence
<220> FEATURE:
<223> OTHER INFORMATION: Response Element

<400> SEQUENCE: 116

Ala Cys Tyr Tyr
1

<210> SEQ ID NO 117
<211> LENGTH: 13
<212> TYPE: DNA
<213> ORGANISM: Artificial sequence
<220> FEATURE:
<223> OTHER INFORMATION: Response element
<220> FEATURE:
<221> NAME/KEY: misc_feature
<222> LOCATION: (7)..(7)
<223> OTHER INFORMATION: n is a, c, g, or t

<400> SEQUENCE: 117
aggtcanagg tca                                                          13

<210> SEQ ID NO 118
<211> LENGTH: 15
<212> TYPE: DNA
<213> ORGANISM: Artificial sequence
<220> FEATURE:
<223> OTHER INFORMATION: Response element

<400> SEQUENCE: 118
gggttgaatg aattt                                                        15

<210> SEQ ID NO 119
<211> LENGTH: 5
<212> TYPE: DNA
<213> ORGANISM: Artificial sequence
<220> FEATURE:
<223> OTHER INFORMATION: luciferase reporter gene linker

<400> SEQUENCE: 119 tataa                                                                    5
```

SUBSTITUTION MUTANT RECEPTORS AND THEIR USE IN A NUCLEAR RECEPTOR-BASED INDUCIBLE GENE EXPRESSION SYSTEM

CROSS REFERENCE TO RELATED APPLICATIONS

This application is a continuation of U.S. application Ser. No. 13/618,693, filed Sep. 14, 2012, which is a continuation of U.S. application Ser. No. 10/468,193, filed Dec. 17, 2013, now U.S. Pat. No. 8,715,959, issued May 6, 2014, which is a National Phase of PCT Appl. No. PCT/US02/05090, filed Feb. 20, 2002, which claims the benefit of U.S. Provisional Appl. No. 60/313,925, filed Aug. 21, 2001 and U.S. Provisional Appl. No. 60/269,799, filed Feb. 20, 2001, each of which is incorporated herein by reference.

FIELD OF THE INVENTION

This invention relates to the field of biotechnology or genetic engineering. Specifically, this invention relates to the field of gene expression. More specifically, this invention relates to novel nuclear receptors comprising a substitution mutation and their use in a nuclear receptor-based inducible gene expression system and methods of modulating the expression of a gene within a host cell using this inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83: 5414-5418; Arnheiter et al., 1990, Cell 62:51-61; Filmus et al., 1992, Nucleic Acids Research 20: 27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, *Science* 262: 1019-24; Belshaw et al., 1996 *Proc Natl Acad Sci USA* 93: 4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998, Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and Cmethoxyfenozide that are marketed world wide by Rohm and Haas Company (see International Patent Application No. PCT/EP96/00686 and U.S. Pat. No. 5,530,028). Both analogs have exceptional safety profiles to other organisms.

The insect ecdysone receptor (EcR) heterodimerizes with Ultraspiracle (USP), the insect homologue of the mammalian RXR, and binds ecdysteroids and ecdysone receptor response elements and activate transcription of ecdysone responsive genes (Riddiford et al, 2000). The EcR/USP/ ligand complexes play important roles during insect development and reproduction. The EcR is a member of the steroid hormone receptor superfamily and has five modular domains, A/B (transactivation), C (DNA binding, heterodimerization)), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of EcR-based gene switch used *Drosophila melanogaster* EcR (DmEcR) and *Mus musculus* RXR (MmRXR) and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 BI discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880,333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and at the same is insensitive to the natural steroids. Thus, improved systems that are simple, compact, and dependent on ligands that are relatively inexpensive, readily available, and of low toxicity to the host would prove useful for regulating biological systems.

Recently, Applicants have shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

The EcR is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

To develop an improved Group H nuclear receptor-based inducible gene expression system in which ligand binding or ligand specificity is modified, Applicants created several substitution mutant EcRs that comprise substituted amino acid residues in the ligand binding domain (LBD). A homology modeling and docking approach was used to predict critical residues that mediate binding of ecdysteroids and non-ecdysteroids to the EcR LBD. These substitution mutant EcRs were evaluated in ligand binding and transactivation assays. As presented herein, Applicants' novel substitution mutant nuclear receptors and their use in a nuclear receptor-based inducible gene expression system provides an improved inducible gene expression system in both prokaryotic and eukaryotic host cells in which ligand sensitivity and magnitude of transactivation may be selected as desired, depending upon the application.

DETAILED DESCRIPTION OF THE INVENTION

Figure 1:
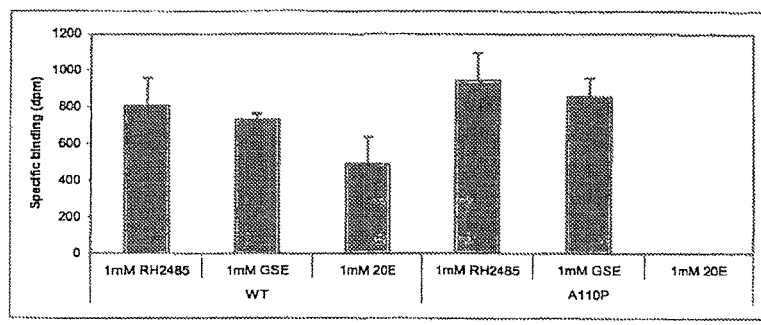
FIG. 1: In vitro $^3$H-RH2485 ligand binding of full-length A110P CfEcR mutant while steroid binding is completely disrupted. The ligand binding values are expressed as specific counts (specific dpm).

Applicants describe herein the construction of Group H nuclear receptors that comprise substitution mutations (referred to herein as "substitution mutants") at amino acid residues that are involved in ligand binding to a Group H nuclear receptor ligand binding domain that affect the ligand sensitivity and magnitude of induction of the Group H nuclear receptor and the demonstration that these substitution mutant nuclear receptors are useful in methods of modulating gene expression.

Specifically, Applicants have developed a novel nuclear receptor-based inducible gene expression system comprising a Group H nuclear receptor ligand binding domain comprising a substitution mutation. Applicants have shown that the effect of such a substitution mutation may increase or reduce ligand binding activity or ligand sensitivity and the ligand may be steroid or non-steroid specific. Thus, Applicants' invention provides a Group H nuclear receptor-based inducible gene expression system useful for modulating expression of a gene of interest in a host cell. In a particularly desirable embodiment, Applicants' invention provides an ecdysone receptor-based inducible gene expression system that responds solely to either steroidal ligand or non-steroidal ligand. In addition, the present invention also provides an improved non-steroidal ligand responsive ecdysone receptor-based inducible gene expression system. Thus, Applicants' novel inducible gene expression system and its use in methods of modulating gene expression in a host cell overcome the limitations of currently available inducible expression systems and provide the skilled artisan with an effective means to control gene expression.

The present invention is useful for applications such as gene therapy, large scale production of proteins and antibodies, cell-based high throughput screening assays, orthogonal ligand screening assays, functional genomics, proteomics, metabolomics, and regulation of traits in transgenic organisms, where control of gene expression levels is desirable. An advantage of Applicants' invention is that it provides a means to regulate gene expression and to tailor expression levels to suit the user's requirements.

Definitions

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (←—→) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Feigner et al., 1987, Proc. Natl. Acad. Sci. U.S.A. 84: 7413; Mackey, et al., 1988, Proc. Natl. Acad. Sci. U.S.A. 85:8027-8031; and Ulmer et al., 1993, Science 259: 1745-1748). The use of cationic lipids may promote encapsulation of negatively charged nucleic acids, and also promote fusion with negatively charged cell membranes (Feigner and Ringold, 1989, Science 337:387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease SI), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANT-GAC/ACYY (see Cherbas L., et. al., (1991), *Genes Dev.* 5, 120-131); AGGTCAN$_{(n)}$AGGTCA, where N$_{(n)}$ can be one or more spacer nucleotides (see D'Avino PP., et. al., (1995), *Mol. Cell. Endocrinol,* 113, 1-9); and GGGTTGAAT-GAATTT (see Antoniewski C, et. al., (1994). Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PH05, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, IP$_L$, IP$_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1, 5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the EIA or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

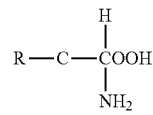

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one (1) wild-type or naturally occurring amino acid with a different amino acid relative to the wild-type or naturally occurring polypeptide. A substitution mutant polypeptide may comprise only one (1) wild-type or naturally occurring amino acid substitution and may be referred to as a "point mutant" or a "single point mutant" polypeptide. Alternatively, a substitution mutant polypeptide may comprise a substitution of two (2) or more wild-type or naturally occurring amino acids with 2 or more amino acids relative to the wild-type or naturally occurring polypeptide. According to the invention, a Group H nuclear receptor ligand binding domain polypeptide comprising a substitution mutation comprises a substitution of at least one (1) wild-type or naturally occurring amino acid with a different amino acid relative to the wild-type or naturally occurring Group H nuclear receptor ligand binding domain polypeptide.

Wherein the substitution mutant polypeptide comprises a substitution of two (2) or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation). Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson, C., et al., 1978, J. Biol. Chem. 253: 6551; Zoller and Smith, 1984, DNA 3: 479-488; Oliphant et al., 1986, Gene 44: 177; Hutchinson et al., 1986, Proc. Natl. Acad. Sci. U.S.A. 83: 710), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215: 403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal". The present invention is useful to search for orthogonal ligands and orthogonal receptor-based gene expression systems such as those described in U.S. application 60/237,446, which is incorporated herein by reference in its entirety.

Gene Expression Modulation System of the Invention

Applicants have identified herein amino acid residues that are involved in ligand binding to a Group H nuclear receptor ligand binding domain that affect the ligand sensitivity and magnitude of induction in an ecdysone receptor-based inducible gene expression system. Applicants describe herein the construction of Group H nuclear receptors that comprise substitution mutations (referred to herein as "substitution mutants") at these critical residues and the demonstration that these substitution mutant nuclear receptors are useful in methods of modulating gene expression. As presented herein, Applicants' novel substitution mutant nuclear receptors and their use in a nuclear receptor-based inducible gene expression system provides an improved inducible gene expression system in both prokaryotic and eukaryotic host cells in which ligand sensitivity and magnitude of transactivation may be selected as desired, depending upon the application.

Thus, the present invention relates to novel substitution mutant Group H nuclear receptor polynucleotides and polypeptides, a nuclear receptor-based inducible gene expression system comprising such mutated Group H nuclear receptor polynucleotides and polypeptides, and methods of modulating the expression of a gene within a host cell using such a nuclear receptor-based inducible gene expression system.

In particular, the present invention relates to a gene expression modulation system comprising at least one gene expression cassette that is capable of being expressed in a host cell comprising a polynucleotide that encodes a polypeptide comprising a Group H nuclear receptor ligand binding domain comprising a substitution mutation. Preferably, the Group H nuclear receptor ligand binding domain comprising a substitution mutation is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. More preferably, the Group H nuclear receptor ligand binding domain comprising a substitution mutation is from an ecdysone receptor.

In a specific embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is a Group H nuclear receptor ligand binding domain comprising a substitution mutation. In a preferred embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

Wherein when only one nuclear receptor ligand binding domain is a Group H ligand binding domain comprising a substitution mutation, the other nuclear receptor ligand binding domain may be from any other nuclear receptor that forms a dimer with the Group H ligand binding domain comprising the substitution mutation. For example, when the Group H nuclear receptor ligand binding domain comprising a substitution mutation is an ecdysone receptor ligand binding domain comprising a substitution mutation, the other nuclear receptor ligand binding domain ("partner") may be from an ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see applications PCT/US01/09050, U.S. 60/294,814, and U.S. 60/294,819, incorporated herein by reference in their entirety). The "partner" nuclear receptor ligand binding domain may further comprise a truncation mutation, a deletion mutation, a substitution mutation, or another modification.

Preferably, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

Preferably, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

Preferably, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In a preferred embodiment, the chimeric RXR ligand binding domain comprises at least one vertebrate species RXR polypeptide fragment and one invertebrate species RXR polypeptide fragment.

In a more preferred embodiment, the chimeric RXR ligand binding domain comprises at least one vertebrate species RXR polypeptide fragment and one non-Dipteran/non-Lepidopteran invertebrate species RXR homolog polypeptide fragment.

In a specific embodiment, the gene whose expression is to be modulated is a homologous gene with respect to the host cell. In another specific embodiment, the gene whose expression is to be modulated is a heterologous gene with respect to the host cell.

The ligands for use in the present invention as described below, when combined with the ligand binding domain of the nuclear receptor(s), which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical.

In a specific example, binding of the ligand to the ligand binding domain of a Group H nuclear receptor and its nuclear receptor ligand binding domain partner enables expression or suppression of the gene. This mechanism does not exclude the potential for ligand binding to the Group H nuclear receptor (GHNR) or its partner, and the resulting formation of active homodimer complexes (e.g. GHNR+ GHNR or partner+partner). Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988), Nature, 335: 563-564) or LexA protein from *Escherichia coli* (see Brent and Ptashne (1985), Cell, 43: 729-736), or synthetic response elements specific for targeted interactions with proteins designed, modified, and selected for such specific interactions (see, for example, Kim, et al. (1997), Proc. Natl. Acad. Sci., USA, 94:3 616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The ecdysone receptor is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), orphan receptor 1 (OR-1), steroid hormone nuclear receptor 1 (NER-1), retinoid X receptor interacting protein-15 (RIP-15), liver X receptor β (LXRβ), steroid hormone receptor like protein (RLD-1), liver X receptor (LXR), liver X receptor α (LXRα), farnesoid X receptor (FXR), receptor interacting protein 14 (RIP-14), and farnesol receptor (HRR-1).

Applicants have developed a CfEcR homology model and have used this homology model together with a published *Chironomous tetans* ecdysone receptor ("CtEcR") homology model (Wurtz et al., 2000) to identify critical residues involved in binding to steroids and non-steroids. The synthetic non-steroids, diacylhydrazines, have been shown to bind lepidopteran EcRs with high affinity and induce precocious incomplete molt in these insects (Wing et al., 1988) and several of these compounds are currently marketed as insecticides. The ligand binding cavity or "pocket" of EcRs has evolved to fit the long backbone structures of ecdysteroids such as 20-hydroxyecdysone (20E). The diacylhydrazines have a compact structure compared to steroids and occupy only the bottom part of the EcR binding pocket. This leaves a few critical residues at the top part of the binding pocket that make contact with steroids but not with non-steroids such as bisacylhydrazines. Applicants describe herein the construction of mutant ecdysone receptors comprising a substitution mutation at these binding pocket residues and have identified several classes of substitution mutant ecdysone receptors with modified ligand binding and transactivation characteristics.

Given the close relatedness of ecdysone receptor to other Group H nuclear receptors, Applicants' identified ecdysone receptor ligand binding domain substitution mutations are also expected to work when introduced into the analogous position of the ligand binding domains of other Group H nuclear receptors to modify their ligand binding or ligand sensitivity. Applicants' novel substitution mutated Group H nuclear receptor polynucleotides and polypeptides are useful in a nuclear receptor-based inducible gene modulation system for various applications including gene therapy, expression of proteins of interest in host cells, production of transgenic organisms, and cell-based assays.

In particular, Applicants describe herein a novel gene expression modulation system comprising a Group H nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides. Applicants have demonstrated for the first time that a substitution mutated nuclear receptor can be used as a component of a nuclear receptor-based inducible gene expression system to modify ligand binding activity and/or ligand specificity in both prokaryotic and eukaryotic cells. As discussed herein, Applicants' findings are both unexpected and surprising.

An ecdysone receptor-based gene expression modulation system of the present invention may be either heterodimeric and homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366: 476-479; Yao, et al., (1992) Cell 71: 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP 140, TIF1, RAP46/Bag-1, ARA70, SRC-1/NCoA-1, TIF2/GRIP/NCoA-2, ACTR/AIBI/RAC3/pCIP as well as the promiscuous coactivator C response element B binding protein, CBP/p300 (for review see Glass et al., Curr. Opin. Cell Biol. 9: 222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N—CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. Applicants have previously shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

Gene Expression Cassettes of the Invention

The novel nuclear receptor-based inducible gene expression system of the invention comprises at least one gene expression cassette that is capable of being expressed in a host cell, wherein the gene expression cassette comprises a polynucleotide that encodes a polypeptide comprising a Group H nuclear receptor ligand binding domain comprising a substitution mutation. Thus, Applicants' invention also provides novel gene expression cassettes for use in the gene expression system of the invention.

In a specific embodiment, the gene expression cassette that is capable of being expressed in a host cell comprises a polynucleotide that encodes a polypeptide selected from the group consisting of a) a polypeptide comprising a transactivation domain, a DNA-binding domain, and a Group H nuclear receptor ligand binding domain comprising a substitution mutation; b) a polypeptide comprising a DNA-binding domain and a Group H nuclear receptor ligand binding domain comprising a substitution mutation; and c) a polypeptide comprising a transactivation domain and a Group H nuclear receptor ligand binding domain comprising a substitution mutation.

In another specific embodiment, the present invention provides a gene expression cassette that is capable of being expressed in a host cell, wherein the gene expression cassette comprises a polynucleotide that encodes a hybrid polypeptide selected from the group consisting of a) a hybrid polypeptide comprising a transactivation domain, a DNA-binding domain, and a Group H nuclear receptor ligand binding domain comprising a substitution mutation; b) a hybrid polypeptide comprising a DNA-binding domain and a Group H nuclear receptor ligand binding domain comprising a substitution mutation; and c) a hybrid polypeptide comprising a transactivation domain and a Group H nuclear receptor ligand binding domain comprising a substitution mutation. A hybrid polypeptide according to the invention comprises at least two polypeptide fragments, wherein each polypeptide fragment is from a different source, i.e, a different polypeptide, a different nuclear receptor, a different species, etc. The hybrid polypeptide according to the invention may comprise at least two polypeptide domains, wherein each polypeptide domain is from a different source.

In a specific embodiment, the Group H nuclear receptor ligand binding domain comprising a substitution mutation is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. In a preferred embodiment, the Group H nuclear receptor ligand binding domain is from an ecdysone receptor.

Thus, the present invention also provides a gene expression cassette comprising a polynucleotide that encodes a polypeptide selected from the group consisting of a) a polypeptide comprising a transactivation domain, a DNA-binding domain, and an ecdysone receptor ligand binding domain comprising a substitution mutation; b) a polypeptide comprising a DNA-binding domain and an ecdysone receptor ligand binding domain comprising a substitution mutation, and c) a polypeptide comprising a transactivation domain and an ecdysone receptor ligand binding domain comprising a substitution mutation. Preferably, the gene expression cassette composes a polynucleotide that encodes a hybrid polypeptide selected from the group consisting of a) a hybrid polypeptide comprising a transactivation domain, a DNA-binding domain, and an ecdysone receptor ligand binding domain comprising a substitution mutation; b) a hybrid polypeptide comprising a DNA-binding domain and an ecdysone receptor ligand binding domain comprising a substitution mutation, and c) a hybrid polypeptide comprising a transactivation domain and an ecdysone receptor ligand binding domain comprising a substitution mutation; wherein the encoded hybrid polypeptide composes at least two polypeptide fragments, wherein each polypeptide fragment is from a different source.

The ecdysone receptor (EcR) ligand binding domain (LBD) may be from an invertebrate EcR, preferably selected from the class Arthropod EcR. Preferably the EcR is selected from the group consisting of a Lepidopteran EcR, a Dipteran EcR, an Orthopteran EcR, a Homopteran EcR and a Hemipteran EcR. More preferably, the EcR ligand binding domain for use in the present invention is from a spruce budworm *Choristoneura fumiferana* EcR ("CfEcR"), a beetle *Tenebrio molitor* EcR ("TmEcR"), a *Manduca sexta* EcR ("MsEcR"), a *Heliothies virescens* EcR ("HvEcR"), a midge *Chironomus tentans* EcR ("CtEcR"), a silk moth *Bombyx mori* EcR ("BmEcR"), a squinting bush brown *Bicyclus anynana* EcR ("BanEcR"), a buckeye *Junonia coenia* EcR ("JcEcR"), a fruit fly *Drosophila melanogaster* EcR ("DmEcR"), a mosquito *Aedes aegypti* EcR ("AaEcR"), a blowfly *Lucilia capitata* ("LcEcR"), a blowfly *Lucilia cuprina* EcR ("LucEcR"), a blowfly *Calliphora vicinia* EcR ("CvEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Celuca pugilator* EcR ("CpEcR"), an ixodid tick *Amblyomma americanum* EcR ("AmaEcR"), a whitefly *Bamecia argentifoli* EcR ("BaEcR", SEQ ID NO: 112) or a leafhopper *Nephotetix cincticeps* EcR ("NcEcR", SEQ ID NO: 113). More preferably, the LBD is from a CfEcR, a DmEcR, or an AmaEcR.

In a specific embodiment, the LBD is from a truncated EcR polypeptide. The EcR polypeptide truncation results in a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. Preferably, the EcR polypeptide truncation results in a deletion of at least a partial polypeptide domain. More preferably, the EcR polypeptide truncation results in a deletion of at least an entire polypeptide domain. In a specific embodiment, the EcR polypeptide truncation results in a deletion of at least an A/B-domain, a C-domain, a D-domain, an F-domain, an A/B/C-domains, an A/B/1/2-C-domains, an A/B/C/D-domains, an A/B/C/D/F-domains, an A/B/F-domains, an A/B/C/F-domains, a partial E domain, or a partial F domain. A combination of several complete and/or partial domain deletions may also be performed.

In a specific embodiment, the Group H nuclear receptor ligand binding domain is encoded by a polynucleotide comprising a codon mutation that results in a substitution of a) amino acid residue 20, 21, 48, 51, 52, 55, 58, 59, 61, 62, 92, 93, 95, 96, 107, 109, 110, 120, 123, 125, 175, 218, 219, 223, 230, 234, or 238 of SEQ ID NO: 1, b) amino acid residues 95 and 110 of SEQ ID NO: 1, c) amino acid residues 218 and 219 of SEQ ID NO: 1, d) amino acid residues 107 and 175 of SEQ ID NO: 1, e) amino acid residues 127 and 175 of SEQ ID NO: 1, f) amino acid residues 107 and 127 of SEQ ID NO: 1, g) amino acid residues 107, 127 and 175 of SEQ ID NO: 1, h) amino acid residues 52, 107 and 175 of SEQ ID NO: 1, i) amino acid residues 96, 107, and 175 of SEQ ID NO: 1, j) amino acid residues 107, 110, and 175 of SEQ ID NO: 1, k) amino acid residue 107, 121, 213, or 217 of SEQ ID NO: 2, or l) amino acid residue 91 or 105 of SEQ ID NO: 3. In a preferred embodiment, the Group H nuclear receptor ligand binding domain is from an ecdysone receptor.

In another specific embodiment, the Group H nuclear receptor ligand binding domain is encoded by a polynucleotide comprising a codon mutation that results in a substitution of a) an alanine residue at a position equivalent or analogous to amino acid residue 20, 21, 48, 51, 55, 58, 59, 61, 62, 92, 93, 95, 109, 120, 125, 218, 219, 223, 230, 234, or 238 of SEQ ID NO: 1, b) an alanine, valine, isoleucine, or leucine residue at a position equivalent or analogous to amino acid residue 52 of SEQ ID NO: 1, c) an alanine, threonine, aspartic acid, or methionine residue at a position equivalent or analogous to amino acid residue 96 of SEQ ID NO: 1, d) a proline, serine, methionine, or leucine residue at a position equivalent or analogous to amino acid residue 110 of SEQ ID NO: 1, e) a phenylalanine residue at a position equivalent or analogous to amino acid residue 123 of SEQ ID NO: 1, f) an alanine residue at a position equivalent or analogous to amino acid residue 95 of SEQ ID NO: 1 and a proline residue at a position equivalent or analogous to amino acid residue 110 of SEQ ID NO: 1, g) an alanine residue at a position equivalent or analogous to amino acid residues 218 and 219 of SEQ ID NO: 1, h) an isoleucine residue at a position equivalent or analogous to amino acid residue 107 of SEQ ID NO: 1, i) an glutamine residue at a position equivalent or analogous to amino acid residues 175 of SEQ ID NO: 1, j) an isoleucine residue at a position equivalent or analogous to amino acid residue 107 of SEQ ID NO: 1 and a glutamine residue at a position equivalent or analogous to amino acid residue 175 of SEQ ID NO: 1, k) a glutamine residue at a position equivalent or analogous to amino acid residues 127 and 175 of SEQ ID NO: 1, l) an isoleucine residue at a position equivalent or analogous to amino acid residue 107 of SEQ ID NO: 1 and a glutamine residue at a position equivalent or analogous to amino acid residue 127 of SEQ ID NO: 1, m) an isoleucine residue at a position equivalent or analogous to amino acid residue 107 of SEQ ID NO: 1 and a glutamine residue at a position equivalent or analogous to amino acid residues 127 and 175 of SEQ ID NO: 1, n) a valine residue at a position equivalent or analogous to amino acid residue 52 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, o) an alanine residue at a position equivalent or analogous to amino acid residue 96 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, p) an alanine residue at a position equivalent or analogous to amino acid residue 52 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, q) a threonine residue at a position equivalent or analogous to amino acid residue 96 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, r) an isoleucine residue at a position equivalent or analogous to amino acid residue 107 of SEQ ID NO: 1, a proline residue at a position equivalent or analogous to amino acid 110 of SEQ ID NO: 1, and a glutamine residue at a position equivalent or analogous to amino acid 175 of SEQ ID NO: 1, s) a proline at a position equivalent or analogous to amino acid residue 107 of SEQ ID NO: 2, t) an arginine or a leucine at a position equivalent or analogous to amino acid residue 121 of SEQ ID NO: 2, u) an alanine at a position equivalent or analogous to amino acid residue 213 of SEQ ID NO: 2, v) an alanine or a serine at a position equivalent or analogous to amino acid residue 217 of SEQ ID NO: 2, w) an alanine at a position equivalent or analogous to amino acid residue 91 of SEQ ID NO: 3, or x) a proline at a position equivalent or analogous to amino acid residue 105 of SEQ ID NO: 3. In a preferred embodiment, the Group H nuclear receptor ligand binding domain is from an ecdysone receptor.

In another specific embodiment, the Group H nuclear receptor ligand binding domain comprising a substitution mutation is an ecdysone receptor ligand binding domain comprising a substitution mutation encoded by a polynucleotide comprising a codon mutation that results in a substitution mutation selected from the group consisting of a) E20A, Q21A, F48A, I51A, T52A, T52V, T52I, T52L, T55A, T58A, V59A, L61A, I62A, M92A, M93A, R95A, V96A, V96T, V96D, V96M, V107I, F109A, A110P, A110S, A110M, A110L, Y120A, A123F, M125A, R175E, M218A, C219A, L223A, L230A, L234A, W238A, R95A/A110P, M218A/C219A, V107I/R175E, Y127E/R175E, V107I/Y127E, V107I/Y127E/R175E, T52V/V107I/R175E, V96A/V107I/R175E, T52A/V107I/R175E, V96T/V107I/R175E or V107I/A110P/R175E substitution mutation of SEQ ID NO: 1, b) A107P, G121R, G121L, N213A, C217A, or C217S substitution mutation of SEQ ID NO: 2, and c) G91A or A105P substitution mutation of SEQ ID NO: 3.

In another specific embodiment, the Group H nuclear receptor ligand binding domain comprising a substitution mutation is an ecdysone receptor ligand binding domain polypeptide comprising a substitution mutation encoded by a polynucleotide that hybridizes to a polynucleotide comprising a codon mutation that results in a substitution mutation selected from the group consisting of a) T58A, A110P, A110L, A110S, or A110M of SEQ ID NO: 1, b) A107P of SEQ ID NO: 2, and c) A105P of SEQ ID NO: 3 under hybridization conditions comprising a hybridization step in less than 500 mM salt and at least 37 degrees Celsius, and a washing step in 2×SSPE at least 63 degrees Celsius. In a preferred embodiment, the hybridization conditions comprise less than 200 mM salt and at least 37 degrees Celsius for the hybridization step. In another preferred embodiment, the hybridization conditions comprise 2×SSPE and 63 degrees Celsius for both the hybridization and washing steps. In another preferred embodiment, the ecdysone receptor ligand binding domain lacks steroid binding activity, such as 20-hydroxyecdysone binding activity, ponasterone A binding activity, or muristerone A binding activity.

In another specific embodiment, the Group H nuclear receptor ligand binding domain comprises a substitution mutation at a position equivalent or analogous to a) amino acid residue 20, 21, 48, 51, 52, 55, 58, 59, 61, 62, 92, 93, 95, 96, 107, 109, 110, 120, 123, 125, 175, 218, 219, 223, 230, 234, or 238 of SEQ ID NO: 1, b) amino acid residues 95 and 110 of SEQ ID NO: 1, c) amino acid residues 218 and 219 of SEQ ID NO: 1, d) amino acid residues 107 and 175 of SEQ ID NO: 1, e) amino acid residues 127 and 175 of SEQ ID NO: 1, f) amino acid residues 107 and 127 of SEQ ID NO: 1, g) amino acid residues 107, 127 and 175 of SEQ ID NO: 1, h) amino acid residues 52, 107 and 175 of SEQ ID NO: 1, i) amino acid residues 96, 107 and 175 of SEQ ID NO: 1, j) amino acid residues 107, 110, and 175 of SEQ ID NO: 1, k) amino acid residue 107, 121, 213, or 217 of SEQ ID NO: 2, or l) amino acid residue 91 or 105 of SEQ ID NO: 3. In a preferred embodiment, the Group H nuclear receptor ligand binding domain is from an ecdysone receptor.

Preferably, the Group H nuclear receptor ligand binding domain comprises a substitution of a) an alanine residue at a position equivalent or analogous to amino acid residue 20, 21, 48, 51, 55, 58, 59, 61, 62, 92, 93, 95, 109, 120, 125, 218, 219, 223, 230, 234, or 238 of SEQ ID NO: 1, b) an alanine, valine, isoleucine, or leucine residue at a position equivalent or analogous to amino acid residue 52 of SEQ ID NO: 1, c) an alanine, threonine, aspartic acid, or methionine residue at a position equivalent or analogous to amino acid residue 96 of SEQ ID NO: 1, d) a proline, serine, methionine, or leucine residue at a position equivalent or analogous to amino acid residue 110 of SEQ ID NO: 1, e) a phenylalanine residue at a position equivalent or analogous to amino acid residue 123 of SEQ ID NO: 1, f) an alanine residue at a position equivalent or analogous to amino acid residue 95 of SEQ ID NO: 1 and a proline residue at a position equivalent or analogous to amino acid residue 110 of SEQ ID NO: 1, g) an alanine residue at a position equivalent or analogous to amino acid residues 218 and 219 of SEQ ID NO: 1, h) an isoleucine residue at a position equivalent or analogous to amino acid residue 107 of SEQ ID NO. 1, i) a glutamine residue at a position equivalent or analogous to amino acid residues 175, j) an isoleucine residue at a position equivalent or analogous to amino acid residue 107 of SEQ ID NO: 1 and a glutamine residue at a position equivalent or analogous to amino acid residue 175 of SEQ ID NO: 1, k) a glutamine residue at a position equivalent or analogous to amino acid residues 127 and 175 of SEQ ID NO: 1, l) an isoleucine residue at a position equivalent or analogous to amino acid residue 107 of SEQ ID NO: 1 and a glutamine residue at a position equivalent or analogous to amino acid residue 127 of SEQ ID NO: 1, m) an isoleucine residue at a position equivalent or analogous to amino acid residue 107 of SEQ ID NO. 1 and a glutamine residue at a position equivalent or analogous to amino acid residues 127 and 175 of SEQ ID NO: 1, n) a valine residue at a position equivalent or analogous to amino acid residue 52 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, o) an alanine residue at a position equivalent or analogous to amino acid residue 96 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, p) an alanine residue at a position equivalent or analogous to amino acid residue 52 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, q) a threonine residue at a position equivalent or analogous to amino acid residue 96 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO. 1, r) an isoleucine residue at a position equivalent or analogous to amino acid residue 107 of SEQ ID NO: 1, a proline residue at a position equivalent or analogous to amino acid 110 of SEQ ID NO: 1, and a glutamine residue at a position equivalent or analogous to amino acid 175 of SEQ ID NO: 1, s) a proline at a position equivalent or analogous to amino acid residue 107 of SEQ ID NO: 2, t) an arginine or a leucme at a position equivalent or analogous to amino acid residue 121 of SEQ ID NO: 2, u) an alanine at a position equivalent or analogous to amino acid residue 213 of SEQ ID NO: 2, v) an alanine or a serine at a position equivalent or analogous to amino acid residue 217 of SEQ ID NO: 2, w) an alanine at a position equivalent or analogous to amino acid residue 91 of SEQ ID NO: 3, or x) a proline at a position equivalent or analogous to amino acid residue 105 of SEQ ID NO: 3. In a preferred embodiment, the Group H nuclear receptor ligand binding domain is from an ecdysone receptor.

In another specific embodiment, the Group H nuclear receptor ligand binding domain comprising a substitution mutation is an ecdysone receptor ligand binding domain polypeptide composing a substitution mutation, wherein the substitution mutation is selected from the group consisting of a) E20A, Q21A, F48A, I51A, T52A, T52V, T52I, T52L, T55A, T58A, V59A, L61A, I62A, M92A, M93A, R95A, V96A, V96T, V96D, V96M, V107L F109A, A110P, A110S, A110M, A110L, Y120A, A123F, M125A, R175E, M218A, C219A, L223A, L230A, L234A, W238A, R95A/A110P, M218A C219A, V107I/R175E, Y127E/R175E, V107I/Y127E, V107I/Y127E/R175E, T52V/V107I/R175E, V96A/V107I/R175E, T52A/V107I/R175E, V96T/V107I/R175E, or V107I/A110P/R175E substitution mutation of SEQ ID NO: 1, b) A107P, G121R, G121L, N213A, C217A, or C217S substitution mutation of SEQ ID NO: 2, and c) G91A or A105P substitution mutation of SEQ ID NO: 3.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a Group H nuclear receptor member DBD, a steroid/thyroid hormone nuclear receptor superfamily member DBD, or a bacterial LacZ DBD. More preferably, the DBD is an EcR DBD [SEQ ID NO: 4 (polynucleotide) or SEQ ID NO: 5 (polypeptide)], a GAL4 DBD [SEQ ID NO: 6 (polynucleotide) or SEQ ID NO: 7 (polypeptide)], or a LexA DBD [(SEQ ID NO: 8 (polynucleotide) or SEQ ID NO: 9 (polypeptide)].

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), or an analog, combination, or modification thereof. In a specific embodiment, the AD is a synthetic or chimeric AD, or is obtained from an EcR, a glucocorticoid receptor, VP16, GAL4, NF-kB, or B42 acidic activation domain AD. Preferably, the AD is an EcR AD [SEQ ID NO: 10 (polynucleotide) or SEQ ID NO: 11 (polypeptide)], a VP16 AD [SEQ ID NO: 12 (polynucleotide) or SEQ ID NO: 13 (polypeptide)], a B42 AD [SEQ ID NO: 14 (polynucleotide) or SEQ ID NO: 15 (polypeptide)], or a p65 AD [SEQ ID NO: 16 (polynucleotide) or SEQ ID NO: 17 (polypeptide)].

In a specific embodiment, the gene expression cassette encodes a hybrid polypeptide comprising either a) a DNA-binding domain encoded by a polynucleotide comprising a nucleic acid sequence of SEQ ID NO: 4, SEQ ID NO: 6, or SEQ ID NO: 8, or b) a transactivation domain encoded by a polynucleotide comprising a nucleic acid sequence of SEQ ID NO: 10, SEQ ID NO: 12, SEQ ID NO: 14, or SEQ ID NO: 16; and a Group H nuclear receptor ligand binding domain comprising a substitution mutation encoded by a polynucleotide according to the invention. Preferably, the Group H nuclear receptor ligand binding domain comprising a substitution mutation is an ecdysone receptor ligand binding domain comprising a substitution mutation encoded by a polynucleotide according to the invention.

In another specific embodiment, the gene expression cassette encodes a hybrid polypeptide comprising either a) a DNA-binding domain comprising an amino acid sequence of SEQ ID NO: 5, SEQ ID NO: 7, or SEQ ID NO: 9, or b) a transactivation domain comprising an amino acid sequence of SEQ ID NO: 11, EQ ID NO: 13, SEQ ID NO: 15, or SEQ ID NO: 17; and a Group H nuclear receptor ligand binding domain comprising a substitution mutation according to the invention. Preferably, the Group H nuclear receptor ligand binding domain comprising a substitution mutation is an ecdysone receptor ligand binding domain comprising a substitution mutation according to the invention.

The present invention also provides a gene expression cassette comprising: i) a response element comprising a domain recognized by a polypeptide comprising a DNA binding domain; ii) a promoter that is activated by a polypeptide comprising a transactivation domain; and iii) a gene whose expression is to be modulated.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a Group H nuclear receptor RE, a steroid/thyroid hormone nuclear receptor RE, or a synthetic RE that recognizes a synthetic DNA binding domain. Preferably, the RE is an ecdysone response element (EcRE) comprising a polynucleotide sequence of SEQ ID NO: 18, a GAL4RE comprising a polynucleotide sequence of SEQ ID NO: 19, or a LexA RE (operon, "op") comprising a polynucleotide sequence of SEQ ID NO: 20 ("2XLexAopRE").

A steroid/thyroid hormone nuclear receptor DNA binding domain, activation domain or response element according to the invention may be obtained from a steroid/thyroid hormone nuclear receptor selected from the group consisting of thyroid hormone receptor α (TRα), thyroid receptor 1 (c-erbA-1), thyroid hormone receptor β (TRβ), retinoic acid receptor α (RARα), retinoic acid receptor β (RARβ, HAP), retinoic acid receptor γ (RARγ), retinoic acid recetor gamma-like (RARD), peroxisome proliferator-activated receptor α (PPARα), peroxisome proliferator-activated receptor β (PPARβ), peroxisome proliferator-activated receptor δ (PPARδ, NUC-1), peroxisome proliferator-activator related receptor (FFAR), peroxisome proliferator-activated receptor γ (PPARγ), orphan receptor encoded by non-encoding strand of thyroid hormone receptor α (REVERBα), v-erb A related receptor (EAR-1), v-erb related receptor (EAR-IA), γ), orphan receptor encoded by non-encoding strand of thyroid hormone receptor β (REVERBβ), v-erb related receptor (EAR-1 β), orphan nuclear recptor BD73 (BD73), rev-erbA-related receptor (RVR), zinc finger protein 126 (HZF2), ecdysone-inducible protein E75 (E75), ecdysone-inducible protein E78 (E78), *Drosophila* receptor 78 (DR-78), retinoid-related orphan receptor α (RORα), retinoid Z receptor α (RZRα), retinoid related orphan receptor β (RORβ), retinoid Z receptor β (RZRβ), retinoid-related orphan receptor γ (RORγ), retinoid Z receptor γ (RZRγ), retinoid-related orphan receptor (TOR), hormone receptor 3 (HR-3), *Drosophila* hormone receptor 3 (DHR-3), *Manduca* hormone receptor (MHR-3), *Galleria* hormone receptor 3 (GHR-3), *C. elegans* nuclear receptor 3 (CNR-3), *Choristoneura* hormone receptor 3 (CHR-3), *C. elegans* nuclear receptor 14 (CNR-14), ecdysone receptor (ECR), ubiquitous receptor (UR), orphan nuclear receptor (OR-1), NER-1, receptor-interacting protein 15 (RIP-15), liver X receptor β (LXRβ), steroid hormone receptor like protein (RLD-1), liver X receptor (LXR), liver X receptor α (LXRα), farnesoid X receptor (FXR), receptor-interacting protein 14 (RIP-14), HRR-1, vitamin D receptor (VDR), orphan nuclear receptor (ONR-1), pregnane X receptor (PXR), steroid and xenobiotic receptor (SXR), benzoate X receptor (BXR), nuclear receptor (MB-67), constitutive androstane receptor 1 (CAR-1), constitutive androstane receptor α (CARα), constitutive androstane receptor 2 (CAR-2), constitutive androstane receptor β (CARβ), *Drosophila* hormone receptor 96 (DHR-96), nuclear hormone receptor 1 (NHR-1), hepatocyte nuclear factor 4 (HNF-4), hepatocyte nuclear factor 4G (HNF-4G), hepatocyte nuclear factor 4B (HNF-4B), hepatocyte nuclear factor 4D (HNF-4D, DI-INF-4), retinoid X receptor α (RXRα), retinoid X receptor β (RXRβ), H-2 region II binding protein (H-2RIIBP), nuclear receptor co-regulator-1 (RCoR-1), retinoid X receptor γ (RXRγ), Ultraspiracle (USP), 2C1 nuclear receptor, chorion factor 1 (CF-1), testicular receptor 2 (TR-2), testicular receptor 2-11 (TR2-11), testicular receptor 4 (TR4), TAK-1, *Drosophila* hormone receptor (DHR78), Tailless (TLL), tailless homolog (TLX), XTLL, chicken ovalbumin upstream promoter transcription factor I (COUP-TFI), chicken ovalbumin upstream promoter transcription factor A (COUP-TFA), EAR-3, SVP-44, chicken ovalbumin upstream promoter transcription factor II (COUP-TFII), chicken ovalbumin upstream promoter transcription factor B (COUP-TFB), ARP-1, SVI O, SVP, chicken ovalbumin upstream promoter transcription factor III (COUP-TFIII), chicken ovalbumin upstream promoter transcription factor G (COUP-TFG), SVP-46, EAR-2, estrogen receptor α (ERα), estrogen receptor β (ERβ), estrogen related receptor 1 (ERR1), estrogen related receptor α (ERRα), estrogen related receptor 2 (ERR2), estrogen related receptor β (ERRβ), glucocorticoid receptor (GR), mineralocorticoid receptor (MR), progesterone receptor (PR), androgen receptor (AR), nerve growth factor induced gene B (NGFI-B), nuclear receptor similar to Nur-77 (TRS), N10, orphan receptor (NUR-77), Human early response gene (NAK-1), Nun related factor 1 (NURR-1), a human immediate-early response gene (NOT), regenerating liver nuclear receptor 1 (RNR-1), hematopoietic zinc finger 3 (HZF-3), Nur rekated protein-1 (TINOR), Nuclear orphan receptor 1 (NOR-1), NOR1 related receptor (MINOR), *Drosophila* hormone receptor 38 (DHR-38), *C. elegans* nuclear receptor δ (CNR-8), C48D5, steroidogenic factor 1 (SF1), endozepine-like peptide (ELP), fushi tarazu factor 1 (FTZ-F1), adrenal 4 binding protein (AD4BP), liver receptor homolog (LRH-1), Ftz-F1-related orphan receptor A (xF-FrA), Ftz-F1-related orphan receptor B (xFFrB), nuclear receptor related to LRH-1 (FFLR), nuclear receptor related to LRH-1 (PHR), fetoprotein transcriptin factor (FTF), germ cell nuclear factor (GCNFM), retinoid receptor-related testis-associated receptor (RTR), knirps (KNI), knirps related (KNRL), Embryonic gonad (EGON), *Drosophila* gene for ligand dependent nuclear receptor (EAGLE), nuclear receptor similar to trithorax (ODR7), Trithorax, dosage sensitive sex reversal adrenal hypoplasia congenita critical region chromosome X gene (DAX-1), adrenal hypoplasia congenita and hypogonadotropic hypogonadism (AHCH), and short heterodimer partner (SHP).

For purposes of this invention, nuclear receptors and Group H nuclear receptors also include synthetic and chimeric nuclear receptors and Group H nuclear receptors and their homologs.

Genes of interest for use in Applicants' gene expression cassettes may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for use in Applicants' gene expression cassettes include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Polynucleotides of the Invention

The novel nuclear receptor-based inducible gene expression system of the invention comprises at least one gene expression cassette comprising a polynucleotide that encodes a Group H nuclear receptor ligand binding domain comprising a substitution mutation. These gene expression cassettes, the polynucleotides they comprise, and the polypeptides they encode are useful as components of a nuclear receptor-based gene expression system to modulate the expression of a gene within a host cell.

Thus, the present invention provides an isolated polynucleotide that encodes a Group H nuclear receptor ligand binding domain comprising a substitution mutation.

In a specific embodiment, the Group H nuclear receptor ligand binding domain is encoded by a polynucleotide comprising a codon mutation that results in a substitution of an amino acid residue at a position equivalent or analogous to a) amino acid residue 20, 21, 48, 51, 52, 55, 58, 59, 61, 62, 92, 93, 95, 96, 107, 109, 110, 120, 123, 125, 175, 218, 219, 223, 230, 234, or 238 of SEQ ID NO: 1, b) amino acid residues 95 and 110 of SEQ ID NO: 1, c) amino acid residues 218 and 219 of SEQ ID NO: 1, d) amino acid residues 107 and 175 of SEQ ID NO: 1, e) amino acid residues 127 and 175 of SEQ ID NO: 1, f) amino acid residues 107 and 127 of SEQ ID NO: 1, g) amino acid residues 107, 127 and 175 of SEQ ID NO: 1, h) amino acid residues 52, 107 and 175 of SEQ ID NO: 1, i) amino acid residues 96, 107 and 175 of SEQ ID NO: 1, j) amino acid residues 107, 110, and 175 of SEQ ID NO: 1, k) amino acid residue 107, 121, 213, or 217 of SEQ ID NO: 2, or l) amino acid residue 91 or 105 of SEQ ID NO: 3. In a preferred embodiment, the Group H nuclear receptor ligand binding domain is from an ecdysone receptor.

In another specific embodiment, the Group H nuclear receptor ligand binding domain is encoded by a polynucleotide comprising a codon mutation that results in a substitution of a) an alanine residue at a position equivalent or analogous to amino acid residue 20, 21, 48, 51, 55, 58, 59, 61, 62, 92, 93, 95, 109, 120, 125, 218, 219, 223, 230, 234, or 238 of SEQ ID NO: 1, b) an alanine, valine, isoleucine, or leucine residue at a position equivalent or analogous to amino acid residue 52 of SEQ ID NO: 1, c) an alanine, threonine, aspartic acid, or methionine residue at a position equivalent or analogous to amino acid residue 96 of SEQ ID NO: 1, d) a proline, serine, methionine, or leucine residue at a position equivalent or analogous to amino acid residue 110 of SEQ ID NO: 1, e) a phenylalanine residue at a position equivalent or analogous to amino acid residue 123 of SEQ ID NO: 1, f) an alanine residue at a position equivalent or analogous to amino acid residue 95 of SEQ ID NO: 1 and a proline residue at a position equivalent or analogous to amino acid residue 110 of SEQ ID NO: 1, g) an alanine residue at a position equivalent or analogous to amino acid residues 218 and 219 of SEQ ID NO: 1, h) an isoleucine residue at a position equivalent or analogous to amino acid residue 107 of SEQ ID NO: 1, i) a glutamine residue at a position equivalent or analogous to amino acid residues 175, j) an isoleucine residue at a position equivalent or analogous to amino acid residue 107 of SEQ ID NO: 1 and a glutamine residue at a position equivalent or analogous to amino acid residue 175 of SEQ ID NO: 1, k) a glutamine residue at a position equivalent or analogous to amino acid residues 127 and 175 of SEQ ID NO: 1, l) an isoleucine residue at a position equivalent or analogous to amino acid residue 107 of SEQ ID NO: 1 and a glutamine residue at a position equivalent or analogous to amino acid residue 127 of SEQ ID NO: 1, m) an isoleucine residue at a position equivalent or analogous to amino acid residue 107 of SEQ ID NO: 1 and a glutamine residue at a position equivalent or analogous to amino acid residues 127 and 175 of SEQ ID NO: 1, n) a valine residue at a position equivalent or analogous to amino acid residue 52 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, o) an alanine residue at a position equivalent or analogous to amino acid residue 96 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, p) an alanine residue at a position equivalent or analogous to amino acid residue 52 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, q) a threonine residue at a position equivalent or analogous to amino acid residue 96 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, r) an isoleucine residue at a position equivalent or analogous to amino acid residue 107 of SEQ ID NO: 1, a proline residue at a position equivalent or analogous to amino acid 110 of SEQ ID NO: 1, and a glutamine residue at a position equivalent or analogous to amino acid 175 of SEQ ID NO: 1, s) a proline at a position equivalent or analogous to amino acid residue 107 of SEQ ID NO: 2, t) an arginine or a leucine at a position equivalent or analogous to amino acid residue 121 of SEQ ID NO: 2, u) an alanine at a position equivalent or analogous to amino acid residue 213 of SEQ ID NO: 2, v) an alanine or a serine at a position equivalent or analogous to amino acid residue 217 of SEQ ID NO: 2, w) an alanine at a position equivalent or analogous to amino acid residue 91 of SEQ ID NO: 3, or x) a proline at a position equivalent or analogous to amino acid residue 105 of SEQ ID NO: 3. In a preferred embodiment, the Group H nuclear receptor ligand binding domain is from an ecdysone receptor.

In another specific embodiment, the Group H nuclear receptor ligand binding domain comprising a substitution mutation is an ecdysone receptor ligand binding domain comprising a substitution mutation encoded by a polynucleotide comprising a codon mutation that results in a substitution mutation selected from the group consisting of a) E20A, Q21A, F48A, I51A, T52A, T52V, T52I, T52L, T55A, T58A, V59A, L61 A, I62A, M92A, M93A, R95A, V96A, V96T, V96D, V96M, V107I, F109A, A110P, A110S, A110M, A110L, Y120A, A123F, M125A, R175E, M218A, C219A, L223A, L230A, L234A, W238A, R95A/A110P, M218A/C219A, V107I/R175E, Y127E/R175E, V107I/Y127E, V107I/Y127E/R175E, T52V/V107I/R175E, V96A/V107I/R175E, T52A/V107I/R175E, V96T/V107I/R175E or V107I/A110P/R175E substitution mutation of SEQ ID NO: 1, b) A107P, G121R, G121L, N213A, C217A, or C217S substitution mutation of SEQ ID NO: 2, and c) G91A or A105P substitution mutation of SEQ ID NO: 3.

In another specific embodiment, the Group H nuclear receptor ligand binding domain comprising a substitution mutation is an ecdysone receptor ligand binding domain comprising a substitution mutation encoded by a polynucleotide that hybridizes to a polynucleotide comprising a codon mutation that results in a substitution mutation selected from the group consisting of a) T58A, A110P, A110L, A110S, or A110M of SEQ D NO: 1, b) A107P of SEQ ID NO: 2, and c) A105P of SEQ ID NO: 3 under hybridization conditions comprising a hybridization step in less than 500 mM salt and at least 37 degrees Celsius, and a washing step in 2×SSPE at least 63 degrees Celsius. In a preferred embodiment, the hybridization conditions comprise less than 200 mM salt and at least 37 degrees Celsius for the hybridization step. In another preferred embodiment, the hybridization conditions comprise 2×SSPE and 63 degrees Celsius for both the hybridization and washing steps. In another preferred embodiment, the ecdysone receptor ligand binding domain lacks binding activity to a steroid such as 20-hydroxyecdysone, ponasterone A, or muristerone A.

The present invention also provides an isolated polynucleotide that encodes a polypeptide selected from the group consisting of a) a polypeptide comprising a transactivation domain, a DNA-binding domain, and a Group H nuclear receptor ligand binding domain comprising a substitution mutation according to the invention; b) a polypeptide comprising a DNA-binding domain and a Group H nuclear receptor ligand binding domain comprising a substitution mutation according to the invention; and c) a polypeptide comprising a transactivation domain and a Group H nuclear receptor ligand binding domain comprising a substitution mutation according to the invention.

In a specific embodiment, the isolated polynucleotide encodes a hybrid polypeptide selected from the group consisting of a) a hybrid polypeptide comprising a transactivation domain, a DNA-binding domain, and a Group H nuclear receptor ligand binding domain comprising a substitution mutation according to the invention; b) a hybrid polypeptide comprising a DNA-binding domain and a Group H nuclear receptor ligand binding domain comprising a substitution mutation according to the invention; and c) a hybrid polypeptide comprising a transactivation domain and a Group H nuclear receptor ligand binding domain comprising a substitution mutation according to the invention.

The present invention also relates to an isolated polynucleotide encoding a Group H nuclear receptor ligand binding domain comprising a substitution mutation, wherein the substitution mutation affects ligand binding activity or ligand sensitivity of the Group H nuclear receptor ligand binding domain.

In particular, the present invention relates to an isolated polynucleotide encoding a Group H nuclear receptor ligand binding domain comprising a substitution mutation, wherein the substitution mutation reduces ligand binding activity or ligand sensitivity of the Group H nuclear receptor ligand binding domain.

In a specific embodiment, the present invention relates to an isolated polynucleotide encoding a Group H nuclear receptor ligand binding domain comprising a substitution mutation, wherein the substitution mutation reduces steroid binding activity or steroid sensitivity of the Group H nuclear receptor ligand binding domain. Preferably, the isolated polynucleotide comprises a codon mutation that results in a substitution of an amino acid residue at a position equivalent or analogous to a) amino acid residue 20, 21, 48, 51, 52, 55, 58, 59, 62, 92, 93, 95, 109, 110, 120, 123, 125, 218, 219, 223, 230, 234, or 238 of SEQ ID NO: 1, b) amino acid residues 95 and 110 of SEQ ID NO: 1, c) amino acid residues 218 and 219 of SEQ ID NO: 1, d) amino acid residue 107, 121, 213, or 217 of SEQ ID NO: 2, or e) amino acid residue 105 of SEQ ID NO: 3. More preferably, the isolated polynucleotide comprises a codon mutation that results in a substitution of a) an alanine residue at a position equivalent or analogous to amino acid residue 20, 21, 48, 51, 52, 55, 58, 59, 62, 92, 93, 95, 109, 120, 125, 218, 219, 223, 230, 234, or 238 of SEQ ID NO: 1, b) a proline residue at a position equivalent or analogous to amino acid residue 110 of SEQ ID NO: 1, c) a phenylalanine residue at a position equivalent or analogous to amino acid residue 123 of SEQ ID NO: 1, d) an alanine residue at a position equivalent or analogous to amino acid residue 95 of SEQ ID NO: 1 and a proline residue at a position equivalent or analogous to amino acid residue 110 of SEQ ID NO: 1, e) an alanine residue at a position equivalent or analogous to amino acid residues 218 and 219 of SEQ ID NO: 1, f) a proline residue at a position equivalent or analogous to amino acid residue 107 of SEQ ID NO: 2, g) an arginine or leucine residue at a position equivalent or analogous to amino acid residue 121 of SEQ ID NO: 2, h) an alanine residue at a position equivalent or analogous to amino acid residue 213 of SEQ ID NO: 2, i) an alanine or a serine residue at a position equivalent or analogous to amino acid residue 217 of SEQ ID NO: 2, or j) a proline residue at a position equivalent or analogous to amino acid residue 105 of SEQ ID NO: 3. Even more preferably, the isolated polynucleotide comprises a codon mutation that results in a substitution mutation of a) E20A, Q21A, F48A, I51A, T52A, T55A, T58A, V59A, I62A, M92A, M93A, R95A, F109A, A110P, Y120A, A123F, M125A, M218A, C219A, L223A, L230A, L234A, W238A, R95A A110P, or M218A/C219A of SEQ ID NO: 1, b) A107P, G121R, G121L, N213A, C217A, or C217S of SEQ ID NO: 2, or c) A105P of SEQ ID NO: 3.

In another specific embodiment, the present invention relates to an isolated polynucleotide encoding a Group H nuclear receptor ligand binding domain comprising a substitution mutation, wherein the substitution mutation eliminates steroid binding activity or steroid sensitivity of the Group H ligand binding domain. Preferably, the isolated polynucleotide comprises a codon mutation that results in a substitution of an amino acid residue at a position equivalent or analogous to a) amino acid residue 58 or 110 of SEQ ID NO: 1, b) amino acid residues 107, 110 and 175 of SEQ ID NO: 1, c) amino acid residue 107, 121, 213, or 217 of SEQ ID NO: 2, or d) amino acid residue 105 of SEQ ID NO: 3. More preferably, the isolated polynucleotide comprises a codon mutation that results in a substitution of a) an alanine at a position equivalent or analogous to amino acid residue 58 of SEQ ID NO: 1, b) a proline, leucine, serine, or methionine residue at a position equivalent or analogous to amino acid residue 110 of SEQ ID NO: 1, c) an isoleucine at a position equivalent or analogous to amino acid residue 107 of SEQ ID NO: 1, a proline at a position equivalent or analogous to amino acid residue 110 of SEQ ID NO: 1, and a glutamine at a position equivalent or analogous to amino acid residue 175 of SEQ ID NO: 1, d) a proline at a position equivalent or analogous to amino acid residue 107 of SEQ ID NO: 2, e) an arginine or a leucine at a position equivalent or analogous to amino acid residue 121 of SEQ ID NO: 2, f) an alanine at a position equivalent or analogous to amino acid residue 213 of SEQ ID NO: 2, g) an alanine or a serine at a position equivalent or analogous to amino acid residue 217 of SEQ ID NO: 2, or h) a proline at a position equivalent or analogous to amino acid residue 105 of SEQ ID NO: 3. Even more preferably, the isolated polynucleotide comprises a codon mutation that results in a substitution mutation selected from the group consisting of a) T58A, A110P, A110L, A110S, A110M, or V107I/A110P/R175E 0 substitution mutation of SEQ ID NO: 1, b) A107P, G121R, G121L, N213A, C217A, or C217S substitution mutation of SEQ ID NO: 2, and c) A105P substitution mutation of SEQ ID NO: 3.

The present invention also relates to an isolated polynucleotide encoding a polypeptide comprising an ecdysone receptor ligand binding domain comprising a substitution mutation, wherein the ecdysone receptor ligand binding domain lacks steroid binding activity. Preferably, the ecdysone receptor ligand binding domain comprises a codon mutation that results in a substitution mutation at an equivalent or analogous amino acid residue to a) amino acid residue 58 or 110 of SEQ ID NO: 1, b) amino acid residues 107, 110 and 175 of SEQ ID NO: 1, b) amino acid residue 107, 121, 213, or 217 of SEQ ID NO: 2, or d) amino acid residue 105 of SEQ ID NO: 3. More preferably, the ecdysone receptor ligand binding domain comprises a codon mutation that results in a substitution of a) an alanine at a position equivalent or analogous to amino acid residue 58 of SEQ ID NO: 1, b) a proline, leucine, serine, or methionine residue at a position equivalent or analogous to amino acid residue 110 of SEQ ID NO: 1, c) an isoleucine at a position equivalent or analogous to amino acid residue 107 of SEQ ID NO: 1, a proline at a position equivalent or analogous to amino acid residue 110 of SEQ ID NO: 1, a glutamine at a position equivalent or analogous to amino acid residue 175 of SEQ ID NO: 1, d) a proline at a position equivalent or analogous to amino acid residue 107 of SEQ ID NO: 2, e) an arginine or a leucine at a position equivalent or analogous to amino acid residue 121 of SEQ ID NO: 2, f) an alanine at a position equivalent or analogous to amino acid residue 213 of SEQ ID NO: 2, g) an alanine or a serine at a position equivalent or analogous to amino acid residue 217 of SEQ ID NO: 2, or h) a proline at a position equivalent or analogous to amino acid residue 105 of SEQ ID NO: 3. Even more preferably, the isolated ecdysone receptor ligand binding domain comprises a codon mutation that results in a substitution mutation selected from the group consisting of a) T58A, A110P, A110L, A110S, A110M, or V107I/A110P/R175E substitution mutation of SEQ ID NO: 1, b) A107P, G121R, G121L, N213A, C217A, or C217S substitution mutation of SEQ ID NO: 2, and c) A105P substitution mutation of SEQ ID NO: 3. In a specific embodiment, the ecdysone receptor ligand binding domain lacks steroid binding activity selected from the group consisting of ecdysone binding activity, 20-hydroxyecdysone binding activity, ponasterone A binding activity, and muristerone A binding activity.

In another specific embodiment, the isolated polynucleotide encoding an ecdysone receptor ligand binding domain comprising a substitution mutation, wherein the ecdysone receptor ligand binding domain lacks steroid binding activity, hybridizes to a polynucleotide comprising a codon mutation that results in a substitution mutation selected from the group consisting of a) T58A, A110P, A110L, A110S, A110M, or V107I/A110P/R175E substitution mutation of SEQ ID NO: 1, b) A107P, G121R, G121L, N213A, C217A, or C217S substitution mutation of SEQ ID NO: 2, and c) A105P substitution mutation of SEQ ID NO: 3 under hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In another preferred embodiment, the hybridization conditions comprise 2×SSPE and 63 degrees Celsius for both the hybridization and washing steps. In another preferred embodiment, the ecdysone receptor ligand binding domain lacks steroid binding activity selected from the group consisting of ecdysone binding activity, 20-hydroxyecdysone binding activity, ponasterone A binding activity, and muristerone A binding activity.

In another specific embodiment, the present invention relates to an isolated polynucleotide encoding a Group H nuclear receptor ligand binding domain comprising a substitution mutation, wherein the substitution mutation reduces non-steroid binding activity or non-steroid sensitivity of the Group H nuclear receptor ligand binding domain. Preferably, the isolated polynucleotide comprises a codon mutation that results in a substitution of an amino acid residue at a position equivalent or analogous to amino acid residue a) 21, 48, 51, 52, 59, 62, 93, 95, 96, 109, 120, 123, 125, 218, 219, 223, 230, 234, or 238 of SEQ ID NO: 1, b) 121, 213, or 217 of SEQ ID NO: 2, or c) 105 of SEQ ID NO: 3. More preferably, the isolated polynucleotide comprises a codon mutation that results in a substitution of a) an alanine residue at a position equivalent or analogous to amino acid residue 21, 48, 51, 59, 62, 93, 95, 96, 109, 120, 125, 218, 219, 223, 230, 234, or 238 of SEQ ID NO: 1, b) a leucine residue at at a position equivalent or analogous to amino acid residue 52 of SEQ ID NO: 1, c) a threonine residue at at a position equivalent or analogous to amino acid residue 96 of SEQ ID NO: 1, d) a phenylalanine residue at at a position equivalent or analogous to amino acid residue 123 of SEQ ID NO: 1, e) an alanine residue at at a position equivalent or analogous to amino acid residue 95 of SEQ ID NO: 1 and a proline residue at a position equivalent or analogous to amino acid residue 110 of SEQ ID NO: 1, f) an alanine residue at at a position equivalent or analogous to amino acid residues 218 and 219 of SEQ ID NO: 1, g) an arginine or a leucine residue at a position equivalent or analogous to amino acid residue 121 of SEQ ID NO: 2, h) an alanine residue at a position equivalent or analogous to amino acid residue 213 of SEQ ID NO: 2, i) an alanine or a serine residue at a position equivalent or analogous to amino acid residue 217 of SEQ ID NO: 2, or j) a proline residue at a position equivalent or analogous to amino acid residue 105 of SEQ ID NO: 3. Even more preferably, the isolated polynucleotide comprises a codon mutation that results in a substitution mutation of a) Q21A, F48A, I51A, T52L, V59A, I62A, M93A, R95A, V96A, V96T, F109A, Y120A, A123F, M125A, M218A, C219A, L223A, L230A, L234A, W238A, R95A/A110P, or M218/C219A of SEQ ID NO: 1, b) G121R, G121L, N213A, C217A, or C217S of SEQ ID NO: 2, or c) A105P of SEQ D NO: 3.

In another specific embodiment, the present invention relates to an isolated polynucleotide encoding a Group H nuclear receptor polypeptide ligand binding domain comprising a substitution mutation, wherein the substitution mutation eliminates non-steroid binding activity or non-steroid sensitivity of the Group H ligand binding domain.

In another specific embodiment, the present invention relates to an isolated polynucleotide encoding a Group H nuclear receptor polypeptide ligand binding domain comprising a substitution mutation, wherein the substitution mutation reduces both steroid binding activity or steroid sensitivity and non-steroid binding activity or non-steroid sensitivity of the Group H ligand binding domain. Preferably, the isolated polynucleotide comprises a codon mutation that results in a substitution of an amino acid residue at a position equivalent or analogous to a) amino acid residue 21, 48, 51, 59, 62, 93, 95, 109, 120, 123, 125, 218, 219, 223, 230, 234, or 238 of SEQ ID NO: 1, b) amino acid residues 95 and 110 of SEQ ID NO: 1, c) amino acid residues 218 and 219 of SEQ ID NO: 1, d) amino acid residue 121, 213, or 217 of SEQ ID NO: 2, or e) amino acid residue 105 of SEQ ID NO: 3. More preferably, the isolated polynucleotide comprises a codon mutation that results in a substitution of a) an alanine residue at a position equivalent or analogous to amino acid residue 21, 48, 51, 59, 62, 93, 95, 109, 120, 125, 218, 219, 223, 230, 234, or 238 of SEQ ID NO: 1, b) a phenylalanine residue at a position equivalent or analogous to amino acid residue 123 of SEQ ID NO: 1, c) an alanine residue at a position equivalent or analogous to amino acid residue 95 of SEQ ID NO: 1 and a proline residue at a position equivalent or analogous to amino acid residue 110 of SEQ ID NO: 1, d) an alanine residue at a position equivalent or analogous to amino acid residues 218 and 219 of SEQ ID NO: 1, e) an arginine or a leucine residue at a position equivalent or analogous to amino acid residue 121 of SEQ ID NO: 2, f) an alanine residue at a position equivalent or analogous to amino acid residue 213 of SEQ ID NO: 2, g) an alanine or a serine residue at a position equivalent or analogous to amino acid residue 217 of SEQ ID NO: 2, or h) a proline residue at a position equivalent or analogous to amino acid residue 105 of SEQ ID NO: 3. Even more preferably, the isolated polynucleotide comprises a codon mutation that results in a substitution mutation of Q21A, F48A, I51A, V59A, I62A, M93A, R95A, F109A, Y120A, A123F, M125A, M218A, C219A, L223A, L230A, L234A, W238A, R95A/A110P, or M218A/C219A of SEQ ID NO: 1, b) G121R, G121L, N213A, C217A, or C217S of SEQ ID NO: 2, or c) A105P of SEQ ID NO: 3.

In addition, the present invention also relates to an isolated polynucleotide encoding a Group H nuclear receptor ligand binding domain comprising a substitution mutation, wherein the substitution mutation enhances ligand binding activity or ligand sensitivity of the Group H nuclear receptor ligand binding domain.

In a specific embodiment, the present invention relates to an isolated polynucleotide encoding a Group H nuclear receptor ligand binding domain comprising a substitution mutation, wherein the substitution mutation enhances steroid binding activity or steroid sensitivity of the Group H nuclear receptor ligand binding domain. Preferably, the isolated polynucleotide comprises a codon mutation that results in a substitution of an amino acid residue at a position equivalent or analogous to a) amino acid residue 52 or 96 of SEQ ID NO: 1 or b) amino acid residue 91 of SEQ ID NO: 3. More preferably, the isolated polynucleotide comprises a codon mutation that results in a substitution of a) a leucine, valine, or isoleucine residue at a position equivalent or analogous to amino acid residue 52 of SEQ ID NO: 1, b) an alanine, threonine, aspartic acid, or methionine residue at a position equivalent or analogous to amino acid residue 96 of SEQ ID NO: 1, c) a threonine residue at a position equivalent or analogous to amino acid residue 96 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, or d) an alanine residue at a position equivalent or analogous to amino acid residue 91 of SEQ ID NO: 3. Even more preferably, the isolated polynucleotide comprises a codon mutation that results in a substitution mutation of a) T52L, T52V, T52I, V96A, V96T, V96D, or V96M of SEQ ID NO: 1 or b) G91A of SEQ ID NO: 3.

In another specific embodiment, the present invention relates to an isolated polynucleotide encoding a Group H nuclear receptor ligand binding domain comprising a substitution mutation, wherein the substitution mutation enhances non-steroid binding activity or non-steroid sensitivity of the Group H nuclear receptor ligand binding domain. Preferably, the isolated polynucleotide comprises a codon mutation that results in a substitution of an amino acid residue at a position equivalent or analogous to amino acid residue 52, 55, or 96 of SEQ ID NO: 1 or b) amino acid residue 91 of SEQ ID NO: 3. More preferably, the isolated polynucleotide comprises a codon mutation that results in a substitution of a) an alanine, valine, or isoleucine residue at a position equivalent or analogous to amino acid residue 52 of SEQ ID NO: 1, b) an alanine residue at a position equivalent or analogous to amino acid residue 55 of SEQ ID NO: 1, c) an aspartic acid or methionine residue at a position equivalent or analogous to amino acid residue 96 of SEQ ID NO: 1, or d) an alanine residue at a position equivalent or analogous to amino acid residue 91 of SEQ ID NO: 3. Even more preferably, the isolated polynucleotide comprises a codon mutation that results in a substitution mutation of a) T52A, T52V, T52I, T55A, V96D, or V96M of SEQ ID NO: 1 or b) G91A of SEQ ID NO: 3.

In another specific embodiment, the present invention relates to an isolated polynucleotide encoding a Group H nuclear receptor ligand binding domain comprising a substitution mutation, wherein the substitution mutation enhances both steroid binding activity or steroid sensitivity and non-steroid binding activity or non-steroid sensitivity of the Group H ligand binding domain. Preferably, the isolated polynucleotide comprises a codon mutation that results in a substitution of an amino acid residue at a position equivalent or analogous to a) amino acid residue 52, 96, 107 or 175 of SEQ ID NO: 1, b) amino acid residues 107 and 175 of SEQ ID NO: 1, c) amino acid residues 127 and 175 of SEQ ID NO: 1, d) amino acid residues 107 and 127 of SEQ ID NO: 1, e) amino acid residues 107, 127 and 175 of SEQ ID NO: 1, f) amino acid residues 52, 107 and 175 of SEQ ID NO: 1, g) amino acid residues 96, 107 and 175 of SEQ ID NO: 1, or h) amino acid residue 91 of SEQ ID NO: 3. More preferably, the isolated polynucleotide comprises a codon mutation that results in a substitution of a) a valine or isoleucine residue at a position equivalent or analogous to amino acid residue 52 of SEQ ID NO: 1, b) an aspartic acid or methionine residue at a position equivalent or analogous to amino acid residue 96 of SEQ ID NO: 1, c) an isoleucine residue at a position equivalent or analogous to amino acid residue 107 of SEQ ID NO: 1, d) a glutamine residue at a position equivalent or analogous to amino acid residues 175, e) an isoleucine residue at a position equivalent or analogous to amino acid residue 107 of SEQ ID NO: 1 and a glutamine residue at a position equivalent or analogous to amino acid residue 175 of SEQ ID NO: 1, f) a glutamine residue at a position equivalent or analogous to amino acid residues 127 and 175 of SEQ ID NO: 1, g) an isoleucine residue at a position equivalent or analogous to amino acid residue 107 of SEQ ID NO: 1 and a glutamine residue at a position equivalent or analogous to amino acid residue 127 of SEQ ID NO: 1, h) an isoleucine residue at a position equivalent or analogous to amino acid residue 107 of SEQ ID NO: 1 and a glutamine residue at a position equivalent or analogous to amino acid residues 127 and 175 of SEQ ID NO: 1, i) a valine residue at a position equivalent or analogous to amino acid residue 52 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, j) an alanine residue at a position equivalent or analogous to amino acid residue 96 of SEQ ID NO: 1, an isoleucine residue at a position equivalent or analogous to amino acid residue 107 of SEQ ID NO: 1 find a glutamine residue at a position equivalent or analogous to amino acid residue 175 of SEQ ID NO: 1, k) an alanine residue at a position equivalent or analogous to amino acid residue 52 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, or l) an alanine residue at a position equivalent or analogous to amino acid residue 91 of SEQ ID NO: 3. Even more preferably, the isolated polynucleotide comprises a codon mutation that results in a substitution mutation of a) T52V, T52I, V96D, V96M, VI07I, R175E, V107I/R175E, Y127E/R175E, V107I/Y127E, V107I/Y127E/R175E, T52V/V107I/R175E, V96A/V107I/R175E or T52A/V107I/R175E of SEQ ID NO: 1 or b) G91A of SEQ ID NO: 3.

In addition, the present invention relates to an expression vector comprising a polynucleotide according the invention, operatively linked to a transcription regulatory element. Preferably, the polynucleotide encoding a nuclear receptor ligand binding domain comprising a substitution mutation is operatively linked with an expression control sequence permitting expression of the nuclear receptor ligand binding domain in an expression competent host cell. The expression control sequence may comprise a promoter that is functional in the host cell in which expression is desired. The vector may be a plasmid DNA molecule or a viral vector. Preferred viral vectors include retrovirus, adenovirus, adeno-associated virus, herpes virus, and vaccinia virus. The invention further relates to a replication defective recombinant virus comprising in its genome, the polynucleotide encoding a nuclear receptor ligand binding domain comprising a substitution mutation as described above. Thus, the present invention also relates to an isolated host cell comprising such an expression vector, wherein the transcription regulatory element is operative in the host cell.

The present invention also relates to an isolated polypeptide encoded by a polynucleotide according to the invention.

Polypeptides of the Invention

The novel nuclear receptor-based inducible gene expression system of the invention comprises at least one gene expression cassette comprising a polynucleotide that encodes a polypeptide comprising a Group H nuclear receptor ligand binding domain comprising a substitution mutation. Thus, the present invention also provides an isolated polypeptide comprising a Group H nuclear receptor ligand binding domain comprising a substitution mutation according to the invention.

In another specific embodiment, the Group H nuclear receptor ligand binding domain comprises a substitution mutation at a position equivalent or analogous to a) amino acid residue 20, 21, 48, 51, 52, 55, 58, 59, 61, 62, 92, 93, 95, 96, 107, 109, 110, 120, 123, 125, 175, 218, 219, 223, 230, 234, or 238 of SEQ ID NO: 1, b) amino acid residues 95 and 110 of SEQ ID NO: 1, c) amino acid residues 218 and 219 of SEQ ID NO: 1, d) amino acid residues 107 and 175 of SEQ ID NO: 1, e) amino acid residues 127 and 25 175 of SEQ ID NO: 1, f) amino acid residues 107 and 127 of SEQ ID NO: 1, g) amino acid residues 107, 127 and 175 of SEQ ID NO: 1, h) amino acid residues 52, 107 and 175 of SEQ ID NO: 1, i) amino acid residues 96, 107 and 175 of SEQ ID NO: 1, j) amino acid residues 107, 110 and 175 of SEQ ID NO: 1, k) amino acid residue 107, 121, 213, or 217 of SEQ ID NO: 2, or l) amino acid residue 91 or 105 of SEQ ID NO: 3. In a preferred embodiment, the Group H nuclear receptor ligand binding domain is from an ecdysone receptor.

Preferably, the Group H nuclear receptor ligand binding domain comprises a substitution of a) an alanine residue at a position equivalent or analogous to amino acid residue 20, 21, 48, 51, 55, 58, 59, 61, 62, 92, 93, 95, 109, 120, 125, 218, 219, 223, 230, 234, or 238 of SEQ ID NO: 1, b) an alanine, valine, isoleucine, or leucine residue at a position equivalent or analogous to amino acid residue 52 of SEQ ID NO: 1, c) an alanine, threonine, aspartic acid, or methionine residue at a position equivalent or analogous to amino acid residue 96 of SEQ ID NO: 1, d) a proline, serine, methionine, or leucine residue at a position equivalent or analogous to amino acid residue 110 of SEQ ID NO: 1, e) a phenylalanine residue at a position equivalent or analogous to amino acid residue 123 of SEQ ID NO: 1, f) an alanine residue at a position equivalent or analogous to amino acid residue 95 of SEQ ID NO: 1 and a proline residue at a position equivalent or analogous to amino acid residue 110 of SEQ ID NO: 1, g) an alanine residue at a position equivalent or analogous to amino acid residues 218 and 219 of SEQ ID NO: 1, h) an isoleucine residue at a position equivalent or analogous to amino acid residue 107 of SEQ ID NO: 1, i) a glutamine residue at a position equivalent or analogous to amino acid residues 175, j) an isoleucine residue at a position equivalent or analogous to amino acid residue 107 of SEQ ID NO: 1 and a glutamine residue at a position equivalent or analogous to amino acid residue 175 of SEQ ID NO: 1, k) a glutamine residue at a position equivalent or analogous to amino acid residues 127 and 175 of SEQ ID NO: 1, l) an isoleucine residue at a position equivalent or analogous to amino acid residue 107 of SEQ ID NO: 1 and a glutamine residue at a position equivalent or analogous to amino acid residue 127 of SEQ ID NO: 1, m) an isoleucine residue at a position equivalent or analogous to amino acid residue 107 of SEQ ID NO: 1 and a glutamine residue at a position equivalent or analogous to amino acid residues 127 and 175 of SEQ ID NO: 1, n) a valine residue at a position equivalent or analogous to amino acid residue 52 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, o) an alanine residue at a position equivalent or analogous to amino acid residue 96 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, p) an alanine residue at a position equivalent or analogous to amino acid residue 52 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, q) a threonine residue at a position equivalent or analogous to amino acid residue 96 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO:1, r) an isoleucine residue at a position equivalent or analogous to amino acid residue 107 of SEQ ID NO: 1, a proline at a position equivalent or analogous to amino acid residue 110 of SEQ ID NO: 1, and a glutamine residue at a position equivalent or analogous to amino acid residue 175 of SEQ ID NO: 1, s) a proline at a position equivalent or analogous to amino acid residue 107 of SEQ ID NO: 2, t) an arginine or a leucine at a position equivalent or analogous to amino acid residue 121 of SEQ ID NO: 2, u) an alanine at a position equivalent or analogous to amino acid residue 213 of SEQ ID NO: 2, v) an alanine or a serine at a position equivalent or analogous to amino acid residue 217 of SEQ ID NO: 2, w) an alanine at a position equivalent or analogous to amino acid residue 91 of SEQ ID NO: 3, or x) a proline at a position equivalent or analogous to amino acid residue 105 of SEQ ID NO: 3. In a preferred embodiment, the Group H nuclear receptor ligand binding domain is from an ecdysone receptor.

In another specific embodiment, the Group H nuclear receptor ligand binding domain comprising a substitution mutation is an ecdysone receptor ligand binding domain polypeptide comprising a substitution mutation, wherein the substitution mutation is selected from the group consisting of a) E20A, Q21A, F48A, I51A, T52A, T52V, T52I, T52L, T55A, T58A, V59A, L61A, I62A, M92A, M93A, R95A, V96A, V96T, V96D, V96M, VI07I, F109A, A110P, A110S, A110M, A110L, Y120A, A123F, M125A, R175E, M218A, C219A, L223A, L230A, L234A, W238A, R95A/A110P, M218A/C219A, V107I/R175E, Y127E/R175E, V107I/Y127E, V107I/Y127E/R175E, T52V/V107I/R175E, V96A/V107I/R175E, T52A/V107I R175E V96T1V107I/R175E, or V107I/A110P/R175E substitution mutation of SEQ ID NO: 1, b) A107P, G121R, G121L, N213A, C217A, or C217S substitution mutation of SEQ ID NO: 2, and c) G91A or A105P substitution mutation of SEQ ID NO: 3.

The present invention also provides an isolated polypeptide selected from the group consisting of a) an isolated polypeptide comprising a transactivation domain, a DNA-binding domain, and a Group H nuclear receptor ligand binding domain comprising a substitution mutation according to the invention; b) an isolated polypeptide comprising a DNA-binding domain and a Group H nuclear receptor ligand binding domain comprising a substitution mutation according to the invention; and c) an isolated polypeptide comprising a transactivation domain and a Group H nuclear receptor ligand binding domain comprising a substitution mutation according to the invention. In a preferred embodiment, the Group H nuclear receptor ligand binding domain is from an ecdysone receptor.

The present invention also provides an isolated hybrid polypeptide selected from the group consisting of a) an isolated hybrid polypeptide comprising a transactivation domain, a DNA-binding domain, and a Group H nuclear receptor ligand binding domain comprising a substitution mutation according to the invention; b) an isolated hybrid polypeptide comprising a DNA-binding domain and a Group H nuclear receptor ligand binding domain comprising a substitution mutation according to the invention; and c) an isolated hybrid polypeptide comprising a transactivation domain and a Group H nuclear receptor ligand binding domain comprising a substitution mutation according to the invention. In a preferred embodiment, the Group H nuclear receptor ligand binding domain is from an ecdysone receptor.

The present invention also provides an isolated polypeptide comprising a Group H nuclear receptor ligand binding domain comprising a substitution mutation that affects ligand binding activity or ligand sensitivity of the Group H nuclear receptor ligand binding domain.

In particular, the present invention relates to an isolated Group H nuclear receptor polypeptide comprising a ligand binding domain comprising a substitution mutation that reduces ligand binding activity or ligand sensitivity of the Group H nuclear receptor ligand binding domain.

In a specific embodiment, the present invention relates to an isolated polypeptide comprising a Group H nuclear receptor ligand binding domain comprising a substitution mutation that reduces steroid binding activity or steroid sensitivity of the Group H nuclear receptor ligand binding domain. Preferably, the isolated polypeptide comprises a substitution of an amino acid residue at a position equivalent or analogous to a) amino acid residue 20, 21, 48, 51, 52, 55, 58, 59, 62, 92, 93, 95, 109, 110, 120, 123, 125, 218, 219, 223, 230, 234, or 238 of SEQ ID NO: 1, b) amino acid residue 107, 121, 213, or 217 of SEQ ID NO: 2, or c) amino acid residue 105 of SEQ ID NO: 3. More preferably, the isolated polypeptide comprises a substitution of a) an alanine residue at a position equivalent or analogous to amino acid residue 20, 21, 48, 51, 52, 55, 58, 59, 62, 92, 93, 95, 109, 120, 125, 218, 219, 223, 230, 234, or 238 of SEQ ID NO: 1, b) a proline residue at a position equivalent or analogous to amino acid residue 110 of SEQ ID NO: 1, c) a phenylalanine residue at a position equivalent or analogous to amino acid residue 123 of SEQ ID NO: 1, d) an alanine residue at a position equivalent or analogous to amino acid residue 95 of SEQ ID NO: 1 and a proline residue at a position equivalent or analogous to amino acid residue 110 of SEQ ID NO: 1, e) an alanine residue at a position equivalent or analogous to amino acid residues 218 and 219 of SEQ ID NO: 1, f) a proline residue at a position equivalent or analogous to amino acid residue 107 of SEQ ID NO: 2, g) an arginine or leucine residue at a position equivalent or analogous to amino acid residue 121 of SEQ ID NO: 2, h) an alanine residue at a position equivalent or analogous to amino acid residue 213 of SEQ ID NO: 2, i) an alanine or a serine residue at a position equivalent or analogous to amino acid residue 217 of SEQ ID NO: 2, or j) a proline residue at a position equivalent or analogous to amino acid residue 105 of SEQ ID NO: 3. Even more preferably, the isolated polypeptide comprises a substitution mutation of a) E20A, Q21A, F48A, I51A, T52A, T55A, T58A, V59A, I62A, M92A, M93A, R95A, F109A, A110P, Y120A, A123F, M125A, M218A, C219A, L223A, L230A, L234A, W238A, R95A/A110P, or M218A C219A of SEQ ID NO: 1, b) A107P, G121R, G121L, N213A, C217A, or C217S of SEQ ID NO: 2, or c) A105P of SEQ ID NO: 3.

In another specific embodiment, the present invention relates to an isolated polypeptide comprising a Group H nuclear receptor ligand binding domain comprising a substitution mutation that eliminates steroid binding activity or steroid sensitivity of the Group H ligand binding domain. Preferably, the isolated polypeptide comprises a substitution of an amino acid residue at a position equivalent or analogous to a) amino acid residue 58 or 110 of SEQ ID NO: 1, b) amino acid residues 107, 110 and 175 of SEQ ID NO: 1, c) amino acid residue 107, 121, 213, or 217 of SEQ ID NO: 2, or d) amino acid residue 105 of SEQ ID NO: 3. More preferably, the isolated polynucleotide comprises a codon mutation that results in a substitution of a) an alanine at a position equivalent or analogous to amino acid residue 58 of SEQ ID NO: 1, b) a proline, leucine, serine, or methionine residue at a position equivalent or analogous to amino acid residue 110 of SEQ ID NO: 1, c) an isoleucine residue at a position equivalent or analogous to amino acid residue 107 of SEQ ID NO: 1, a proline residue at a position equivalent or analogous to amino acid 110 of SEQ ID NO: 1, and a glutamine residue at a position equivalent or analogous to amino acid residue 175 of SEQ ID NO: 1, d) a proline at a position equivalent or analogous to amino acid residue 107 of SEQ ID NO: 2, e) an arginine or a leucine at a position equivalent or analogous to amino acid residue 121 of SEQ ID NO: 2, f) an alanine at a position equivalent or analogous to amino acid residue 213 of SEQ ID NO: 2, g) an alanine or a serine at a position equivalent or analogous to amino acid residue 217 of SEQ ID NO: 2, or h) a proline at a position equivalent or analogous to amino acid residue 105 of SEQ ID NO: 3. Even more preferably, the isolated polypeptide comprises a substitution mutation selected from the group consisting of a) T58A, A110P, A110L, A110S, A110M, or V107I/A110P/R175E substitution mutation of SEQ ID NO: 1, b) A107P, G121R, G121L, N213A, C217A, or C217S substitution mutation of SEQ ID NO: 2, and c) A105P substitution mutation of SEQ ID NO: 3.

The present invention also relates to an isolated polypeptide comprising an ecdysone receptor ligand binding domain comprising a substitution mutation, wherein the ecdysone receptor ligand binding domain lacks steroid binding activity. Preferably, the ecdysone receptor ligand binding domain comprises a substitution mutation at an equivalent or analogous amino acid residue to a) amino acid residue 58 or 110 of SEQ ID NO: 1, b) amino acid residues 107, 110 and 175 of SEQ ID NO: 1, c) amino acid residue 107, 121, 213, or 217 of SEQ ID NO: 2, or d) amino acid residue 105 of SEQ ID NO: 3. More preferably, the ecdysone receptor ligand binding domain comprises a substitution of a) an alanine at a position equivalent or analogous to amino acid residue 58 of SEQ ID NO: 1, b) a proline, leucine, serine, or methionine residue at a position equivalent or analogous to amino acid residue 110 of SEQ ID NO: 1, c) an isoleucine residue at a position equivalent or analogous to amino acid residue 107 of SEQ ID NO: 1, a proline residue at a position equivalent or analogous to amino acid residue 110 of SEQ ID NO: 1, and a glutamine residue at a position equivalent or analogous to amino acid residue 175 of SEQ ID NO: 1, d) a proline at a position equivalent or analogous to amino acid residue 107 of SEQ ID NO: 2, e) an arginine or a leucine at a position equivalent or analogous to amino acid residue 121 of SEQ ID NO: 2, f) an alanine at a position equivalent or analogous to amino acid residue 213 of SEQ ID NO: 2, g) an alanine or a serine at a position equivalent or analogous to amino acid residue 217 of SEQ ID NO: 2, or h) a proline at a position equivalent or analogous to amino acid residue 105 of SEQ ID NO: 3. Even more preferably, the ecdysone receptor ligand binding domain comprises a substitution mutation selected from the group consisting of a) T58A, A110P, A110L, A110S, A110M, or V107I/A110P/R175E substitution mutation of SEQ ID NO: 1, b) A107P, G121R, G121L, N213A, C217A, or C217S substitution mutation of SEQ ID NO: 2, and c) A105P substitution mutation of SEQ ID NO: 3. In a specific embodiment, the ecdysone receptor ligand binding domain lacks steroid binding activity selected from the group consisting of ecdysone binding activity, 20-hydroxyecdysone binding activity, ponasterone A binding activity, and muristerone A binding activity.

In another specific embodiment, the isolated polypeptide comprising an ecdysone receptor ligand binding domain comprising a substitution mutation, wherein the ecdysone receptor ligand binding domain lacks steroid binding activity and is encoded by a polynucleotide that hybridizes to a polynucleotide comprising a codon mutation that results in a substitution mutation selected from the group consisting of a) T58A, A110P, A110L, A110S, A110M, or V107I/A110P/R175E substitution mutation of SEQ ID NO: 1, b) A107P, G121R, G121L, N213A, C217A, or C217S substitution mutation of SEQ ID NO: 2, and c) A105P substitution mutation of SEQ ID NO: 3 under hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In another preferred embodiment, the hybridization conditions comprise 2×SSPE and 63 degrees Celsius for both the hybridization and washing steps. In another preferred embodiment, the ecdysone receptor ligand binding domain lacks steroid binding activity selected from the group consisting of ecdysone binding activity, 20-hydroxyecdysone binding activity, ponasterone A binding activity, and muristerone A binding activity.

In another specific embodiment, the present invention relates to an isolated polypeptide comprising a Group H nuclear receptor ligand binding domain comprising a substitution mutation that reduces non-steroid binding activity or non-steroid sensitivity of the Group H nuclear receptor ligand binding domain. Preferably, the isolated polypeptide comprises a substitution of an amino acid residue at a position equivalent or analogous to amino acid residue a) 21, 48, 51, 52, 59, 62, 93, 95, 96, 109, 120, 123, 125, 218, 219, 223, 230, 234, or 238 of SEQ ID NO: 1, b) 121, 213, or 217 of SEQ ID NO: 2, or c) 105 of SEQ ID NO: 3. More preferably, the isolated polypeptide comprises a substitution of a) an alanine residue at a position equivalent or analogous to amino acid residue 21, 48, 51, 59, 62, 93, 95, 96, 109, 120, 125, 218, 219, 223, 230, 234, or 238 of SEQ ID NO: 1, b) a leucine residue at at a position equivalent or analogous to amino acid residue 52 of SEQ ID NO: 1, c) a threonine residue at at a position equivalent or analogous to amino acid residue 96 of SEQ ID NO: 1, d) a phenylalanine residue at at a position equivalent or analogous to amino acid residue 123 of SEQ ID NO: 1, e) an alanine residue at at a position equivalent or analogous to amino acid residue 95 of SEQ ID NO: 1 and a proline residue at a position equivalent or analogous to amino acid residue 110 of SEQ ID NO: 1, f) an alanine residue at at a position equivalent or analogous to amino acid residues 218 and 219 of SEQ ID NO: 1, g) an arginine or a leucine residue at a position equivalent or analogous to amino acid residue 121 of SEQ ID NO: 2, h) an alanine residue at a position equivalent or analogous to amino acid residue 213 of SEQ ID NO: 2, i) an alanine or a serine residue at a position equivalent or analogous to amino acid residue 217 of SEQ ID NO: 2, or j) a proline residue at a position equivalent or analogous to amino acid residue 105 of SEQ ID NO: 3. Even more preferably, the isolated polypeptide comprises a substitution mutation of a) Q21A, F48A, I51A, T52L, V59A, I62A, M93A, R95A, V96A, V96T, F109A, Y120A, A123F, M125A, M218A, C219A, L223A, L230A, L234A, W238A, R95A A110P, or M218/C219A of SEQ ID NO: 1, b) G121R, G121L, N213A, C217A, or C217S of SEQ ID NO: 2, or c) A105P of SEQ ID NO: 3.

In another specific embodiment, the present invention relates to an isolated polypeptide comprising a Group H nuclear receptor polypeptide ligand binding domain comprising a substitution mutation that eliminates non-steroid binding activity or non-steroid sensitivity of the Group H ligand binding domain.

In another specific embodiment, the present invention relates to an isolated polypeptide comprising a Group H nuclear receptor polypeptide ligand binding domain comprising a substitution mutation that reduces both steroid binding activity or steroid sensitivity and non-steroid binding activity or non-steroid sensitivity of the Group H ligand binding domain. Preferably, the isolated polypeptide comprises a substitution of an amino acid residue at a position equivalent or analogous to a) amino acid residue 21, 48, 51, 59, 62, 93, 95, 109, 120, 123, 125, 218, 219, 223, 230, 234, or 238 of SEQ ID NO: 1, b) amino acid residues 95 and 110 of SEQ ID NO: 1, c) amino acid residues 218 and 219 of SEQ ID NO: 1, d) amino acid residue 121, 213, or 217 of SEQ ID NO: 2, ore) amino acid residue 105 of SEQ ID NO: 3. More preferably, the isolated polypeptide comprises a substitution of a) an alanine residue at a position equivalent or analogous to amino acid residue 21, 48, 51, 59, 62, 93, 95, 109, 120, 125, 218, 219, 223, 230, 234, or 238 of SEQ ID NO: 1, b) a phenylalanine residue at a position equivalent or analogous to amino acid residue 123 of SEQ ID NO: 1, c) an alanine residue at a position equivalent or analogous to amino acid residue 95 of SEQ ID NO: 1 and a proline residue at a position equivalent or analogous to amino acid residue 110 of SEQ ID NO: 1, d) an alanine residue at a position equivalent or analogous to amino acid residues 218 and 219 of SEQ ID NO: 1, e) an arginine or leucine residue at a position equivalent or analogous to amino acid residue 121 of SEQ ID NO: 2, f) an alanine residue at a position equivalent or analogous to amino acid residue 213 of SEQ ID NO: 2, g) an alanine or serine residue at a position equivalent or analogous to amino acid residue 217 of SEQ ID NO: 2, or h) a proline residue at a position equivalent or analogous to amino acid residue 105 of SEQ ID NO: 3. Even more preferably, the isolated polypeptide comprises a substitution mutation of Q21A, F48A, I51A, V59A, I62A, M93A, R95A, F109A, Y120A, A123F, M125A, M218A, C219A, L223A, L230A, L234A, W238A, R95A/A110P, or M218A C219A of SEQ ID NO: 1, b) G121R, G121L, N213A, C217A, or C217S of SEQ ID NO: 2, or c) A105P of SEQ ID NO: 3.

In addition, the present invention also relates to an isolated polypeptide comprising a Group H nuclear receptor ligand binding domain comprising a substitution mutation that enhances ligand binding activity or ligand sensitivity of the Group H nuclear receptor ligand binding domain.

In a specific embodiment, the present invention relates to an isolated polypeptide comprising a Group H nuclear receptor ligand binding domain comprising a substitution mutation that enhances steroid binding activity or steroid sensitivity of the Group H nuclear receptor ligand binding domain. Preferably, the isolated polypeptide comprises a substitution of an amino acid residue at a position equivalent or analogous to a) amino acid residue 52 or 96 of SEQ ID NO: 1, b) amino acid residues 96, 107 and 175 of SEQ ID NO: 1, or c) amino acid residue 91 of SEQ ID NO: 3. More preferably, the isolated polypeptide comprises a substitution of a) a leucine, valine, or isoleucine residue at a position equivalent or analogous to amino acid residue 52 of SEQ ID NO: 1, b) an alanine, threonine, aspartic acid, or methionine residue at a position equivalent or analogous to amino acid residue 96 of SEQ ID NO: 1, c) a threonine residue at a position equivalent or analogous to amino acid residue 96 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, or d) an alanine residue at a position equivalent or analogous to amino acid residue 91 of SEQ ID NO: 3. Even more preferably, the isolated polypeptide comprises a substitution mutation of a) T52L, T52V, T52I, V96A, V96T, V96D, V96M, or V96T/V107I/R175E of SEQ ID NO: 1 or b) G91A of SEQ ID NO: 3.

In another specific embodiment, the present invention relates to an isolated polypeptide comprising a Group H nuclear receptor ligand binding domain comprising a substitution mutation that enhances non-steroid binding activity or non-steroid sensitivity of the Group H nuclear receptor ligand binding domain. Preferably, the isolated polypeptide comprises a substitution of an amino acid residue at a position equivalent or analogous to amino acid residue 52, 55, or 96 of SEQ ID NO: 1 or b) amino acid residue 91 of SEQ ID NO: 3. More preferably, the isolated polypeptide comprises a substitution of a) an alanine, valine, or isoleucine residue at a position equivalent or analogous to amino acid residue 52 of SEQ ID NO: 1, b) an alanine residue at a position equivalent or analogous to amino acid residue 55 of SEQ ID NO: 1, c) an aspartic acid or methionine residue at a position equivalent or analogous to amino acid residue 96 of SEQ ID NO: 1, or d) an alanine residue at a position equivalent or analogous to amino acid residue 91 of SEQ ID NO: 3. Even more preferably, the isolated polypeptide comprises a substitution mutation of a) T52A, T52V, T52I, T55A, V96D, or V96M of SEQ ID NO: 1 orb) G91A of SEQ ID NO: 3.

In another specific embodiment, the present invention relates to an isolated polypeptide comprising a Group H nuclear receptor ligand binding domain comprising a substitution mutation that enhances both steroid binding activity or steroid sensitivity and non-steroid binding activity or non-steroid sensitivity of the Group H ligand binding domain. Preferably, the isolated polypeptide comprises a substitution of an amino acid residue at a position equivalent or analogous to a) amino acid residue 52, 96, 107 or 175 of SEQ ID NO: 1, b) amino acid residues 107 and 175 of SEQ ID NO: 1, c) amino acid residues 127 and 175 of SEQ ID NO: 1, d) amino acid residues 107 and 127 of SEQ ID NO: 1, e) amino acid residues 107, 127 and 175 of SEQ ID NO: 1, f) amino acid residues 52, 107 and 175 of SEQ ID NO: 1, g) amino acid residues 96, 107 and 175 of SEQ ID NO: 1, or h) amino acid residue 91 of SEQ ID NO: 3. More preferably, the isolated polypeptide comprises a substitution of a) a valine or isoleucine residue at a position equivalent or analogous to amino acid residue 52 of SEQ ID NO: 1, b) an aspartic acid or methionine residue at a position equivalent or analogous to amino acid residue 96 of SEQ ID NO: 1, c) an isoleucine residue at a position equivalent or analogous to amino acid residue 107 of SEQ ID NO: 1, d) a glutamine residue at a position equivalent or analogous to amino acid residues 175, e) an isoleucine residue at a position equivalent or analogous to amino acid residue 107 of SEQ ID NO: 1 and a glutamine residue at a position equivalent or analogous to amino acid residue 175 of SEQ ID NO: 1, f) a glutamine residue at a position equivalent or analogous to amino acid residues 127 and 175 of SEQ ID NO: 1, g) an isoleucine residue at a position equivalent or analogous to amino acid residue 107 of SEQ ID NO: 1 and a glutamine residue at a position equivalent or analogous to amino acid residue 127 of SEQ ID NO: 1, h) an isoleucine residue at a position equivalent or analogous to amino acid residue 107 of SEQ ID NO: 1 and a glutamine residue at a position equivalent or analogous to amino acid residues 127 and 175 of SEQ ID NO: 1, i) a valine residue at a position equivalent or analogous to amino acid residue 52 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, j) an alanine residue at a position equivalent or analogous to amino acid residue 96 of SEQ ID NO: 1, an isoleucine residue at a position equivalent or analogous to amino acid residue 107 of SEQ ID NO: 1 and a glutamine residue at a position equivalent or analogous to amino acid residue 175 of SEQ ID NO: 1, k) an alanine residue at a position equivalent or analogous to amino acid residue 52 of SEQ ID NO: 1, an isoleucine residue at a position equivalent or analogous to amino acid residue 107 of SEQ ID NO: 1, and a glutamine residue at a position equivalent or analogous to amino acid residue 175 of SEQ ID NO: 1, or l) an alanine residue at a position equivalent or analogous to amino acid residue 91 of SEQ ID NO: 3. Even more preferably, the isolated polypeptide comprises a substitution mutation of a) T52V, T52I, V96D, V96M, V107I, R175E, V107I/R175E, Y127E/R175E, V107I/Y127E, V107I/Y127E/R175E, T52V/V107I/R175E, V96A/V107I/R175E, or T52A/V107I/R175E of SEQ ID NO: 1 or b) G91A of SEQ ID NO: 3.

The present invention also relates to compositions comprising an isolated polypeptide according to the invention.
Method of Modulating Gene Expression of the Invention Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

Applicants' invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Genes of interest for expression in a host cell using Applicants' methods may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for expression in a host cell using Applicants' methods include, but are not limited to: antigens produced in plants as vaccines, enzymes like alpha-amylase, phytase, glucanes, xylase and xylanase, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Acceptable ligands are any that modulate expression of the gene when binding of the DNA binding domain of the gene expression system according to the invention to the response element in the presence of the ligand results in activation or suppression of expression of the genes. Preferred ligands include an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, Juvenile hormone III, and the like.

In a preferred embodiment, the ligand for use in Applicants' method of modulating expression of gene is a compound of the formula:

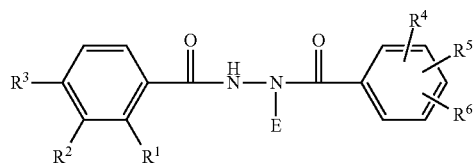

wherein:

E is a $(C_4-C_6)$alkyl containing a tertiary carbon or a cyano$(C_3-C_5)$alkyl containing a tertiary carbon; R' is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, OH, OMe, OEt, cyclopropyl, $CF_2CF_3$, CH=CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, Ac, F, CI, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$ $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C°CH, 1-propynyl, 2-propynyl, vinyl, OMe, OEt, SMe, or SEt.

In another preferred embodiment, the ligand for use in Applicants' method of modulating expression of gene is an ecdysone, 20-hydroxyecdysone, ponasterone A, muristerone A, an oxysterol, a 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, or Juvenile hormone III.

In another preferred embodiment, a second ligand may be used in addition to the first ligand discussed above in Applicants' method of modulating expression of a gene. Preferably, this second ligand is 9-cis-retinoic acid or a synthetic analog of retinoic acid.

Host Cells and Non-Human Organisms of the Invention

As described above, the gene expression modulation system of the present invention may be used to modulate gene expression in a host cell. Expression in transgenic host cells may be useful for the expression of various genes of interest. Applicants' invention provides for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanes, xylase and xylanase, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Thus, Applicants' invention provides an isolated host cell comprising a gene expression system according to the invention. The present invention also provides an isolated host cell comprising a gene expression cassette according to the invention. Applicants' invention also provides an isolated host cell comprising a polynucleotide or a polypeptide according to the invention. The present invention also relates to a host cell transfected with an expression vector according to the invention. The host cell may be a bacterial cell, a fungal cell, a nematode cell, an insect cell, a fish cell, a plant cell, an avian cell, an animal cell, or a mammalian cell. In still another embodiment, the invention relates to a method for producing a nuclear receptor ligand binding domain comprising a substitution mutation, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated host cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum, papaya*, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the host cell is a yeast cell selected from the group consisting of a *Saccharomyces*, a *Pichia*, and a *Candida* host cell.

In another specific embodiment, the host cell is a *Caenorhabdus elegans* nematode cell.

In another specific embodiment, the host cell is an insect cell.

In another specific embodiment, the host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum, papaya*, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another specific embodiment, the host cell is a zebrafish cell.

In another specific embodiment, the host cell is a chicken cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and posttranslational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces, Pichia*, and *Candida*.

In another specific embodiment, the non-human organism is a *Caenorhabdus elegans* nematode.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum, papaya*, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Measuring Gene Expression/Transcription

One useful measurement of Applicants' methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

Ligand Screening Assays

The present invention also relates to methods of screening for a compound that induces or represses transactivation of a nuclear receptor ligand binding domain comprising a substitution mutation in a cell by contacting a nuclear receptor ligand binding domain with a candidate molecule and detecting reporter gene activity in the presence of the ligand. Candidate compounds may be either agonists or antagonists of the nuclear receptor ligand binding domain. In a preferred embodiment, the nuclear receptor ligand binding domain is expressed from a polynucleotide in the cell and the transactivation activity (i.e., expression or repression of a reporter gene) or compound binding activity is measured.

Accordingly, in addition to rational design of agonists and antagonists based on the structure of a nuclear receptor ligand binding domain, the present invention contemplates an alternative method for identifying specific ligands of a nuclear receptor ligand binding domain using various screening assays known in the art.

Any screening technique known in the art can be used to screen for Group H nuclear receptor ligand binding domain agonists or antagonists. For example, a suitable cell line comprising a nuclear receptor-based gene expression system according to the invention can be transfected with a gene expression cassette encoding a marker gene operatively linked to an inducible or repressible promoter. The transfected cells are then exposed to a test solution comprising a candidate agonist or antagonist compound, and then assayed for marker gene expression or repression. The presence of more marker gene expression relative to control cells not exposed to the test solution is an indication of the presence of an agonist compound in the test solution. Conversely, the presence of less marker gene expression relative to control cells not exposed to the test solution is an indication of the presence of an antagonist compound in the test solution.

The present invention contemplates screens for small molecule ligands or ligand analogs and mimics, as well as screens for natural ligands that bind to and agonize or antagonize a Group H nuclear receptor ligand binding domain according to the invention in vivo. For example, natural products libraries can be screened using assays of the invention for molecules that agonize or antagonize nuclear receptor-based gene expression system activity.

Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249: 386-390 (1990); Cwirla, et al., *Proc. Natl. Acad. Sci.,* 87: 6378-6382 (1990); Devlin et al., *Science,* 249: 404-406 (1990)], very large libraries can be constructed ($10^6$-$10^8$ chemical entities). A second approach uses primarily chemical methods, of which the Geysen method [Geysen et al., *Molecular Immunology* 23: 709-715 (1986); Geysen et al. *J. Immunologic Method* 102: 259-274 (1987)] and the method of Fodor et al. [*Science* 251: 767-773 (1991)] are examples. Furka et al. [14th International Congress of Biochemistry, Volume 5, Abstract FR:013 (1988); *Furka, Int. J. Peptide Protein Res.* 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90: 10700-4 (1993); Ohlmeyer et al., *Proc. Natl. Acad. Sci. USA* 90: 10922-10926 (1993); Lam et al., International Patent Publication No. WO 92/00252; Kocis et al., International Patent Publication No. WO 9428028, each of which is incorporated herein by reference in its entirety], and the like can be used to screen for candidate ligands according to the present invention.

The screening can be performed with recombinant cells that express a nuclear receptor ligand binding domain according to the invention, or alternatively, using purified protein, e.g., produced recombinantly, as described above. For example, labeled, soluble nuclear receptor ligand binding domains can be used to screen libraries, as described in the foregoing references.

In one embodiment, a Group H nuclear receptor ligand binding domain according to the invention may be directly labeled. In another embodiment, a labeled secondary reagent may be used to detect binding of a nuclear receptor ligand binding domain of the invention to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two-color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two-color assays may be performed with two or more colored latex beads, or fluorophores that emit at different wavelengths. Labeled molecules or cells may be detected visually or by mechanical/optical means. Mechanical/optical means include fluorescence activated sorting, i.e., analogous to FACS, and micromanipulator removal means.

The present invention may be better understood by reference to the following non-limiting Examples, which are provided as exemplary of the invention.

EXAMPLES

Applicants have developed a CfEcR homology model and have used this homology model together with a published *Chironomous tetans* ecdysone receptor ("CtEcR") homology model (Wurtz et al., 2000) to identify critical residues involved in binding to steroids and non-steroids. The synthetic non-steroids, diacylhydrazines, have been shown to bind lepidopteran EcRs with high affinity and induce precocious incomplete molt in these insects (Wing et al., 1988) and several of these compounds are currently marketed as insecticides. The ligand binding cavity of EcRs has evolved to fit the long back bone structures of ecdysteroids such as 20E. The diacylhydrazines have a compact structure compared to steroids and occupy only the bottom part of the EcR binding pocket. This leaves a few critical residues at the top part of the binding pocket that make contact with steroids but not with non-steroids such as diacylhydrazines. Applicants made substitution mutations of the residues that make contact with steroids and/or non-steroids and determined the mutational effect on ligand binding. Applicants describe herein substitution mutations at several of these residues and have identified several classes of substitution mutant receptors based upon their binding and transactivation characteristics. Applicants' novel substitution mutated nuclear receptor polynucleotides and polypeptides are useful in a nuclear receptor-based inducible gene modulation system for various applications including gene therapy, expression of proteins of interest in host cells, production of transgenic organisms, and cell-based assays.

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "µl" means microliter(s), "ml" means milliliter(s), "L" means liter(s), "µM" means micromolar, "mM" means millimolar, "µg" means microgram(s), "mg" means milligram(s), "A" means adenine or adenosine, "T" means thymine or thymidine, "G" means guanine or guanosine, "C" means cytidine or cytosine, "xg" means times gravity, "nt" means nucleotide(s), "aa" means amino acid(s), "bp" means base pair(s), "kb" means kilobase(s), "k" means kilo, "µ" means micro, and "° C." means degrees Celsius.

Example 1

This Example describes the construction of several gene expression cassettes comprising novel substitution mutated Group H nuclear receptor polynucleotides and polypeptides of the invention for use in a nuclear receptor-based inducible gene expression system. Applicants constructed several gene expression cassettes based on the spruce budworm *Choristoneura fumiferana* EcR ("CfEcR"), fruit fly *Drosophila melanogaster* EcR ("DmEcR"), ixodid tick *Amblyomma americanum* EcR ("AmaEcR"), locust *Locusta migratoria* ultraspiracle protein ("LmUSP"), an invertebrate RXR homolog of vertebrate RXR, and *C. fumiferana* USP ("CfUSP"). The prepared receptor constructs comprise a ligand binding domain of either an EcR, an invertebrate USP, or an invertebrate RXR; and a GAL4 DNA binding domain (DBD) or a VP16 transactivation domain (AD). The reporter constructs include a reporter gene, luciferase or LacZ (β-galactosidase), operably linked to a synthetic promoter construct that comprises a GAL4 response element to which the Gal4 DBD binds. Various combinations of these receptor and reporter constructs were cotransfected into mammalian cells as described in Examples 2-10 infra.

Gene Expression Cassettes:

Ecdysone receptor-based gene expression cassettes (switches) were constructed as followed, using standard cloning methods available in the art. The following is a brief description of preparation and composition of each switch used in the Examples described herein.

1.1—GAL4CfEcR-DEF/VP16LmUSP-EF: The wild-type D, E, and F domains from spruce budworm *Choristoneura fumiferana* EcR ("CfEcR-DEF"; SEQ ID NO: 21) were fused to a GAL4 DNA binding domain ("Gal4DNABD" or "Gal4DBD"; SEQ ID NO: 6) and placed under the control of an SV40e promoter (SEQ ID NO: 22). The E and F domains from locust *Locusta migratoria* ultraspiracle protein ("LmUSP-EF"; SEQ ID NO: 23) were fused to the transactivation domain from VP16 ("VP16AD"; SEQ ID NO: 12) and placed under the control of an SV40e promoter (SEQ ID NO: 22). Five consensus GAL4 response element binding sites ("5XGAL4RE"; comprising 5 copies of a GAL4RE comprising SEQ ID NO: 19) were fused to a synthetic Elb minimal promoter (SEQ ID NO: 24) and placed upstream of the luciferase gene (SEQ ID NO: 25).

1.2—GAL4/mutantCfEcR-DEF/VP16LmUSP-EF:

This construct was prepared in the same way as in switch 1.1 above except wild-type CfEcR-DEF was replaced with mutant CfEcR-DEF comprising a ligand binding domain comprising a substitution mutation selected from Table 1 below.

TABLE 1

Substitution Mutants of *Choristoneura fumiferana* Ecdysone Receptor ("CfEcR") Ligand Binding Domain (LBD).

| CfEcR-DEF LBD Mutation | Resulting "WT to Mutant" Amino Acid Substitution | Corresponding amino acid in full length CfEcR (SEQ ID NO: 26) |
|---|---|---|
| E20A | Glutamic Acid (E) to Alanine (A) | 303 |
| Q21A | Glutamine (Q) to Alanine (A) | 304 |
| F48A | Phenylalanine (F) to Alanine (A) | 331 |
| I51A | Isoleucine (I) to Alanine (A) | 334 |
| T52A | Threonine (T) to Alanine (A) | 335 |
| T52L | Threonine (T) to Leucine (L) | 335 |
| T52V | Threonine (T) to Valine (V) | 335 |
| T52I | Threonine (T) to Isoleucine (I) | 335 |
| T55A | Threonine (T) to Alanine (A) | 338 |
| T58A | Threonine (T) to Alanine (A) | 341 |
| V59A | Valine (V) to Alanine (A) | 342 |
| L61A | Leucine (L) to Alanine (A) | 344 |
| I62A | Isoleucine (I) to Alanine (A) | 345 |
| M92A | Methionine (M) to Alanine (A) | 375 |
| M93A | Methionine (M) to Alanine (A) | 376 |
| R95A | Arginine (R) to Alanine (A) | 378 |
| V96A | Valine (V) to Alanine (A) | 379 |
| V96T | Valine (V) to Threonine (T) | 379 |
| V96D | Valine (V) to Aspartic Acid (D) | 379 |
| V96M | Valine (V) to Methionine (M) | 379 |
| V107I | Valine (V) to Isoleucine | 390 |
| F109A | Phenylalanine (F) to Alanine (A) | 392 |
| A110P | Alanine (A) to Proline (P) | 393 |
| A110S | Alanine (A) to Serine (S) | 393 |
| A110L | Alanine (A) to Leucine (L) | 393 |
| A110M | Alanine (A) to Methionine (M) | 393 |
| Y120A | Tyrosine (Y) to Alanine (A) | 403 |
| A123F | Alanine (A) to Phenylalanine (F) | 406 |
| M125A | Methionine (M) to Alanine (A) | 408 |
| R175E | Arginine (R) to Glutamine (E) | 458 |
| M218A | Methionine (M) to Alanine (A) | 501 |
| C219A | Cysteine (C) to Alanine (A) | 502 |
| L223A | Leucine (L) to Alanine (A) | 506 |
| L230A | Leucine (L) to Alanine (A) | 513 |
| L234A | Leucine (L) to Alanine (A) | 517 |
| W238A | Tryptophan (W) to Alanine (A) | 521 |
| R95A and A110P double mutant | Arginine (R) to Alanine (A) and Alanine (A) to Proline (P), respectively | 378 and 393, respectively |
| V107I and R175E double mutant | Valine (V) to Isoleucine (I) and Arginine (R) to Glutamine (E), respectively | 390 and 458, respectively |
| V107E and Y127E double mutant | Valine (V) to Isoleucine (I) and Tyrosine (Y) to Glutamine (E), respectively | 390 and 410, respectively |
| Y127E and R175E double mutant | Tyrosine (Y) to Glutamine (E) and Arginine (R) to Glutamine (E), respectively | 410 and 458, respectively |
| M218A and C219A double mutant | Methionine (M) to Alanine (A) and Cysteine (C) to Alanine (A), respectively | 501 and 502, respectively |
| T52V, V107I and R175E triple mutant | Threonine (T) to Valine (V), Valine (V) to Isoleucine (I) and Arginine (R) to Glutamine (E), respectively | 335, 390 and 458, respectively |
| T52A, V107I and R175E triple mutant | Threonine (T) to Alanine (A), Valine (V) to Isoleucine (I) and Arginine (R) to Glutamine (E), respectively | 335, 390 and 458, respectively |
| V96A, V107I and R175E triple mutant | Valine (V) to Alanine (A), Valine (V) to Isoleucine (I) and Arginine (R) to Glutamine (E), respectively | 379, 390 and 458, respectively |
| V96T, V107I and R175E triple mutant | Valine (V) to Threonine (T), Valine (V) to Isoleucine (I) and Arginine (R) to Glutamine (E), respectively | 379, 390 and 458, respectively |
| V107I, Y127E and R175E triple mutant | Valine (V) to Isoleucine (I), Tyrosine (Y) to Glutamine (E) and Arginine (R) to Glutamine (E), respectively | 390, 410 and 458, respectively |
| V107I, A110P and R175E triple mutant | Valine (V) to Isoleucine (I), Alanine (A) to Proline (P) and Arginine (R) to Glutamine (E), respectively | 390, 393, and 458, respectively |

1.3—GAL4CfEcR-A/BCDEF/VP16LmUSP-EF:

The full-length spruce budworm *Choristoneura fumiferana* EcR ("CfEcR-A/BCDEF"; SEQ ID NO: 27) was fused to a GAL4 DNA binding domain ("GaWDNABD" or "Gal4DBD"; SEQ ID NO: 6) and placed under the control of an SV40e promoter (SEQ ID NO: 22). The E and F domains from *Locusta migratoria* ultraspiracle ("LmUSP-EF"; SEQ ID NO: 23) were fused to the transactivation domain from VP16 ("VP16AD"; SEQ ID NO: 12) and placed under the control of an SV40e promoter (SEQ ID NO: 22). Five consensus GAL4 response element binding sites ("5XGAL4RE"; comprising 5 copies of a GAL4RE comprising SEQ ID NO: 19) were fused to a synthetic Elb minimal promoter (SEQ ID NO: 24) and placed upstream of the luciferase gene (SEQ ID NO: 25).

1.4—GAL4/A110PmutantCfEcR-A/BCDEF/VP16LmUSP-EF:

This construct was prepared in the same way as in switch 1.3 above except wild-type CfEcR-A/BCDEF was replaced with a mutant CfEcR-A/BCDEF comprising a ligand binding domain comprising an A110P substitution mutation as described in Table 1 above.

1.5—VP16/CfEcR-CDEF:

This construct was prepared in the same way as switch 1.1 except the GAL4 DNA binding domain was replaced with the transactivation domain from VP16 ("VP16AD"; SEQ ID NO: 12) and placed under the control of a baculovirus IE1 promoter (SEQ ID NO: 28). Six consensus ecdysone response element binding sites ("6XEcRE"; comprising 6 copies of an ecdysone RE comprising SEQ ID NO: 18) were fused to a synthetic Elb minimal promoter (SEQ ID NO: 24) and placed upstream of the β-galactosidase gene (SEQ ID NO: 29). This construct uses endogenous ultraspiracle protein as a heterodimerization partner.

1.6—VP16/A110PmutantCfEcR-CDEF:

This construct was prepared in the same way as in switch 1.5 above except wild-type CfEcR-CDEF was replaced with a mutant CfEcR-CDEF comprising a ligand binding domain comprising an A110P substitution mutation as described in Table 1 above.

1.7—Bacterially Expressed CfUSP-A/BCDEF:

This construct was prepared with the A/BCDEF domains from spruce budworm *C. fumiferana* USP ("CfUSP-A/BCDEF"; SEQ ID NO: 30).

1.8—GAL4/DmEcR-CDEF/VP16LmUSP-EF:

The wild-type C, D, E, and F domains from fruit fly *Drosophila melanogaster* EcR ("DmEcR-CDEF"; SEQ ID NO: 31) were fused to a GAL4 DNA binding domain ("Gal4DNABD" or "Gal4DBD"; SEQ ID NO: 6) and placed under the control of an SV40e promoter (SEQ ID NO: 22). The E and F domains from locust *Locusta migratoria* ultraspiracle protein ("LmUSP-EF"; SEQ ID NO: 23) were fused to the transactivation domain from VP16 ("VP16AD"; SEQ ID NO: 12) and placed under the control of an SV40e promoter (SEQ ID NO: 22). Five consensus GAL4 response element binding sites ("5XGAL4RE"; comprising 5 copies of a GAL4RE comprising SEQ ID NO: 19) were fused to a synthetic Elb minimal promoter (SEQ ID NO: 24) and placed upstream of the luciferase gene (SEQ ID NO: 25).

1.9—GAL4/mutantDmEcR-CDEF/VP16LmUSP-EF:

This construct was prepared in the same way as in switch 1.8 above except wild-type DmEcR-CDEF was replaced with mutant DmEcR-CDEF comprising a ligand binding domain comprising a substitution mutation selected from Table 2 below.

TABLE 2

Substitution Mutants of *Drosophila melanogaster* Ecdysone Receptor ("DmEcR") Ligand Binding Domain (LBD).

| DmEcR-CDEF LBD Mutation | Resulting "WT to Mutant" Amino Acid Substitution | Corresponding amino acid in full length DmEcR (SEQ ID NO: 32) |
|---|---|---|
| A107P | Alanine (A) to Proline (P) | 522 |
| G121R | Glycine (G) to Arginine (R) | 536 |
| G121L | Glycine (G) to Leucine (L) | 536 |
| N213A | Asparagine (N) to Alanine (A) | 628 |
| C217A | Cysteine (C) to Alanine (A) | 632 |
| C217S | Cysteine (C) to Serine (S) | 632 |

1.10—VP16/DmEcR-CDEF:

This construct was prepared in the same way as switch 1.8 except the GAL4 DNA binding domain was replaced with the transactivation domain from VP16 ("VP16AD"; SEQ ID NO: 12) and placed under the control of a baculovirus IE1 promoter (SEQ ID NO: 28). Six consensus ecdysone response element binding sites ("6XEcRE"; comprising 6 copies of an ecdysone RE comprising SEQ ID NO: 18) were fused to a synthetic Elb minimal promoter (SEQ ID NO: 24) and placed upstream of the β-galactosidase gene (SEQ ID NO: 29). This construct uses endogenous ultraspiracle protein as a heterodimerization partner.

1.11—VP16/mutantDmEcR-CDEF:

This construct was prepared in the same way as in switch 1.10 above except wild-type DmEcR-CDEF was replaced with a mutant DmEcR-CDEF comprising a ligand binding domain comprising a substitution mutation selected from Table 2 above.

1.12—GAL4/AmaEcR-DEF/VP16LmUSP-EF:

The wild-type D, E, and F domains from ixodid tick *Amblyomma americanum* EcR ("AmaEcR-DEF"; SEQ ID NO: 33) were fused to a GAL4 DNA binding domain ("Gal4DNABD" or "Gal4DBD"; SEQ ID NO: 6) and placed under the control of an SV40e promoter (SEQ ID NO: 22). The E and F domains from locust *Locusta migratoria* ultraspiracle protein ("LmUSP-EF"; SEQ ID NO: 23) were fused to the transactivation domain from VP16 ("VP16AD"; SEQ ID NO: 12) and placed under the control of an SV40e promoter (SEQ ID NO: 22). Five consensus GAL4 response element binding sites ("5XGAL4RE"; comprising 5 copies of a GAL4RE comprising SEQ ID NO: 19) were fused to a synthetic Elb minimal promoter (SEQ ID NO: 24) and placed upstream of the luciferase gene (SEQ ID NO: 25).

1.13—GAL4/mutantAmaEcR-DEFNP16LmUSP-EF:

This construct was prepared in the same way as in switch 1.12 above except wild-type AmaEcR-DEF was replaced with mutant AmaEcR-DEF comprising a ligand binding domain comprising a substitution mutation selected from Table 3 below.

TABLE 3

Substitution Mutants of *Amblyomma americanum* Ecdysone Receptor ("AmaEcR") Ligand Binding Domain (LBD).

| AmaEcR-DEF LBD Mutation | Resulting "WT to Mutant" Amino Acid Substitution | Corresponding amino acid in full length AmaEcR (SEQ ID NO: 34) |
|---|---|---|
| G91A | Glycine (G) to Alanine (A) | 417 |
| A105P | Alanine (A) to Proline (P) | 431 |

Construction of Ecdysone Receptor Ligand Binding Domains Comprising a Substitution Mutation:

In an effort to modify EcR ligand binding, residues within the EcR ligand binding domains that were predicted to be important for ligand binding based upon a molecular modeling analysis were mutated in EcRs from three different classes of organisms. Tables 1-3 indicate the amino acid residues within the ligand binding domain of CfEcR (Lepidopteran EcR), DmEcR (Dipteran EcR) and AmaEcR (Arthopod EcR), respectively that were mutated and examined for modification of steroid and non-steroid binding.

Each one of the amino acid substitution mutations listed in Tables 1-3 was constructed in an EcR cDNA by PCR mediated site-directed mutagenesis to alanine (or to proline or phenylalanine in the case of a wild-type alanine residue, e.g. CfEcR residues A110 and A123, respectively). Amino acids T52, V96 and A110 of CfEcR were mutated to four different amino acids. Five different double point mutant CfEcRs were also made: one comprising both the R95A and A110P substitutions (R95A+A110P, "DM"), a second comprising both the M218A and C219A substitutions (M218A+C219A), a third comprising both the V107I and R175E substitutions (V107I+R175E), a fourth comprising Y127E and R175E substitutions (Y127E+R175E), and a fifth comprising V107I and Y127E substitutions (V107I+Y127E). Six different triple point mutant CfEcRs were also made: one comprising both the V107I and R175E substitutions and a Y127E substitution (V107I+Y127E+R175E), a second comprising a T52V substitution and the V107I and R175E substitutions (T52V+V107I+R175E), a third comprising the V96A, V107I, and R175E substitutions (V96A+V107I+R175E), a fourth comprising the T52A, V107I and R175E substitutions (T52A+V107I+R175E), a fifth comprising a V96T substitution and the V107I and R175E substitutions (V96T+V107I+R175E), and a sixth comprising the A110P, V107I, and R175E substitutions.

PCR site-directed mutagenesis was performed using the Quikchange site-directed mutagenesis kit (Stratagene, La Jolla, Calif.) using the reaction conditions and cycling parameters as follows. PCR site-directed mutagenesis was performed using 1× reaction buffer (supplied by manufacturer), 50 ng of dsDNA template, 125 ng of forward primer (FP), 125 ng of reverse complementary primer (RCP), and 1 µl of dNTP mix (supplied by manufacturer) in a final reaction volume of 50 µL. The forward primer and reverse complementary primer used to produce each EcR mutant are presented in Tables 4-6. The cycling parameters used consisted of one cycle of denaturing at 95° C. for 30 seconds, followed by 16 cycles of denaturating at 95° C. for 30 seconds, annealing at 55° C. for 1 minute, and extending at 68° C. for 22 minutes.

TABLE 4

PCR Primers for Substitution Mutant CfEcR Ligand Binding Domain Construction

| MUTANT | PRIMER (SEQ ID NO:) | PRIMER NUCLEOTIDE SEQUENCE (5'-3') |
|---|---|---|
| E20A | (SEQ ID NO: 35) | gtaccaggacgggtacgcgcagccttctgatgaagatttg |
| E20A | (SEQ ID NO: 36) | caaatcttcatcagaaggctgcgcgtacccgtcctggtac |
| Q21A | (SEQ ID NO: 37) | ccaggacgggtacgaggcgccttctgatgaagatttg |
| Q21A | (SEQ ID NO: 38) | caaatcttcatcagaaggcgctcgtacccgtcctgg |
| F48A | (SEQ ID NO: 39) | gagtctgacactcccgcccgccagatcacag |
| F48A | (SEQ ID NO: 40) | ctgtgatctggcgggcgggagtgtcagactc |
| I51A | (SEQ ID NO: 41) | cactcccttccgccaggccacagagatgac |
| I51A | (SEQ ID NO: 42) | gtcatctctgtggcctggcggaagggagtg |
| T52A | (SEQ ID NO: 43) | cactcccttccgccagatcgcagagatgac |
| T52A | (SEQ ID NO: 44) | gtcatctctgcgatctggcggaagggagtg |
| T55A | (SEQ ID NO: 45) | cgccagatcacagagatggccatcctcacggtcc |
| T55A | (SEQ ID NO: 46) | ggaccgtgaggatagccatctctgtgatctggcg |
| T58A | (SEQ ID NO: 47) | gagatgactatcctcgcggtccaacttatcgtg |
| T58A | (SEQ ID NO: 48) | cacgataagttggaccgcgaggatagtcatctc |
| V59A | (SEQ ID NO: 49) | gatgactatcctcacggcccaacttatcgtgg |
| V59A | (SEQ ID NO: 50) | ccacgataagttgggccgtgaggatagtcatc |
| L61A | (SEQ ID NO: 51) | ctatcctcacggtccaagctatcgtggagttcgcg |
| L61A | (SEQ ID NO: 52) | cgcgaactccacgatagcttggaccgtgaggatag |
| I62A | (SEQ ID NO: 53) | ctatcctcacggtccaacttgccgtggagttcgcg |
| I62A | (SEQ ID NO: 54) | cgcgaactccacggcaagttggaccgtgaggatag |
| M92A | (SEQ ID NO: 55) | gctcaagtgaggtagcgatgctccgagtcgc |
| M92A | (SEQ ID NO: 56) | gcgactcggagcatcgctacctcacttgagc |
| M93A | (SEQ ID NO: 57) | gctcaagtgaggtaatggcgctccgagtcgc |
| M93A | (SEQ ID NO: 58) | gcgactcggagcgccattacctcacttgagc |
| V96A | (SEQ ID NO: 59) | gtaatgatgctccgagccgcgcgacgatac |
| V96A | (SEQ ID NO: 60) | gtatcgtcgcgcggctcggagcatcattac |
| R95A | (SEQ ID NO: 61) | gtgaggtaatgatgctcgcagtcgcgcgacgatacg |
| R95A | (SEQ ID NO: 62) | cgtatcgtcgcgcgactgcgagcatcattacctcac |
| F108A | (SEQ ID NO: 63) | cagacagtgttctggccgcgaacaaccaagcg |

TABLE 4-continued

PCR Primers for Substitution Mutant CfEcR Ligand Binding Domain Construction

| MUTANT | PRIMER (SEQ ID NO:) | PRIMER NUCLEOTIDE SEQUENCE (5'-3') |
|---|---|---|
| F108A | (SEQ ID NO: 64) | cgcttggttgttcgcggccagaacactgtctg |
| F109A | (SEQ ID NO: 65) | tcagacagtgttctggccgcgaacaaccaagcg |
| F109A | (SEQ ID NO: 66) | cgcttggttgttcgcggccagaacactgtctga |
| A11P | (SEQ ID NO: 67) | cagacagtgttctgttcccgaacaaccaagcg |
| A11P | (SEQ ID NO: 68) | cgcttggttgttcgggaacagaacactgtctg |
| Y120A | (SEQ ID NO: 69) | cactcgcgacaacgcccgcaaggctggcatg |
| Y120A | (SEQ ID NO: 70) | catgccagccttgcgggcgttgtcgcgagtg |
| A123F | (SEQ ID NO: 71) | cgacaactaccgcaagtttggccatggcctacgtc |
| A123F | (SEQ ID NO: 72) | gacgtaggccatggccaaacttgcggtagttgtcg |
| M125A | (SEQ ID NO: 73) | ctaccgcaaggctggcgcggcctacgtcatc |
| M125A | (SEQ ID NO: 74) | gatgacgtaggccgcgccagccttgcggtag |
| L230A | (SEQ ID NO: 75) | gctcaagaacagaaaggcgccgcctttcctcg |
| L230A | (SEQ ID NO: 76) | cgaggaaaggcggcgcctttctgttcttgagc |
| L223A | (SEQ ID NO: 77) | ctccaacatgtgcatctccgccaagctcaagaacag |
| L223A | (SEQ ID NO: 78) | ctgttcttgagcttggcggagatgcacatgttggag |
| L234A | (SEQ ID NO: 79) | gaaagctgccgcctttcgccgaggagatctg |
| L234A | (SEQ ID NO: 80) | cagatctcctcggcgaaaggcggcagctttc |
| W238A | (SEQ ID NO: 81) | ctttcctcgaggagatcgcggatgtggcagg |
| W238A | (SEQ ID NO: 82) | cctgccacatccgcgatctcctcgaggaaag |
| A110n | (SEQ ID NO: 83) | cagacagtgttctgttgncgaacaaccaagcg |
| A110n | (SEQ ID NO: 84) | cgcttggttgttcgncaacagaacactgtctg |
| A110n | (SEQ ID NO: 85) | cagacagttctgttgnngaacaaccaagcg |
| A110n | (SEQ ID NO: 86) | cgcttggttgttcnncaacagaacactgtctg |
| T52n | (SEQ ID NO: 87) | cactcccttccgccagatcnnngagatgactatcctcacg |
| T52n | (SEQ ID NO: 88) | cgtgaggatagtcatctcnnngatctggcggaagggagt |
| V96n | (SEQ ID NO: 89) | gtaatgatgctccgannngcgcgacgatacgatgcggc |
| V96n | (SEQ ID NO: 90) | gccgcatcgtatcgtcgcgcnnntcggagcatcattac |
| V107I | (SEQ ID NO: 107) | gcggcctcagacagtattctgttcgcgaac |
| R175E | (SEQ ID NO: 108) | ggtggaagaaatccaggagtactacctgaatacgctcc |
| Y127E | (SEQ ID NO: 109) | caaggctggcatggccgaggcatcgagg |
| T52V | (SEQ ID NO: 110) | cccttccgccagatcgtagagatgactatcctcac |
| V96T | (SEQ ID NO: 111) | ggtaatgatgctccgaaccgcgcgacgatacg |

TABLE 5

PCR Primers for Substitution Mutant DmEcR Ligand Binding Domain Construction

| MUTANT | PRIMER (SEQ ID NO:) | PRIMER NUCLEOTIDE SEQUENCE (5'-3') |
|---|---|---|
| A107P | (SEQ ID NO: 91) | tcggactccatattcttccgaataatagatcatatac |
| A107P | (SEQ ID NO: 92) | gtatatgatctattattcgggaagaatattgagtccga |
| G121R | (SEQ ID NO: 93) | tcttacaaaatggcccgaatggctgataacattg |
| G121R | (SEQ ID NO: 94) | caatgttatcagccattcgggccattagtaaga |
| G121L | (SEQ ID NO: 95) | tcttacaaaatggccctaatggctgataacattg |
| G121L | (SEQ ID NO: 96) | caatgttatcagtccattagggccattttgtaaga |
| N213A | (SEQ ID NO: 97) | acgctgggcaaccaggccgccgagatgtgtttc |
| N213A | (SEQ ID NO: 98) | gaaacacatctcggcggcctggttgcccagcgt |
| C217A | (SEQ ID NO: 99) | cagaacgccgagatggctttctcactaaagctc |
| C217A | (SEQ ID NO: 100) | gagctttagtgagaaagccatctcggcgttctg |
| C217S | (SEQ ID NO: 101) | cagaacgccgagatgtctttctcactaaagctc |
| C217S | (SEQ ID NO: 102) | gagctttagtgagaaagacatctcggcgttctg |

TABLE 6

PCR Primers for Substitution Mutant AmaEcR Ligand Binding Domain Construction

| MUTANT | PRIMER (SEQ ID NO:) | PRIMER NUCLEOTIDE SEQUENCE (5'-3') |
|---|---|---|
| G91A | (SEQ ID NO: 103) | gtgatgatgctgagagctgcccggaaatatgatg |
| G91A | (SEQ ID NO: 104) | catcatatttccgggcagctctcagcatcatcac |
| A105P | (SEQ ID NO: 105) | acagattctatagtgtttcccaataaccagccgtacac |
| A105P | (SEQ ID NO: 106) | gtgtacggctggttattgggaaacactatagaatctgt |

The resulting PCR nucleic acid products encoding the mutant EcR ligand binding domains were then each fused to a GAL4 DNA binding domain as described in Examples 1.2, 1.4, 1.9 and 1.13 above. The GAL4/mutant EcR receptor constructs were tested for activity by transfecting them into NIH3T3 cells along with VP16/LmUSP-EF and pFRLuc in the presence of steroid or non-steroid ligand.

The resulting nucleic acids encoding the mutant EcR ligand binding domains were also each fused to a VP16 transactivation domain as described in Examples 1.6 and 1.11 above. The VP16/mutant CfEcR-DEF and VP16/mutant DmEcR-CDEF receptor constructs were tested for activity by transfecting them into L57 insect cells along with a 6XEcRE/β-galactosidase reporter gene in the presence of 20-hydroxyecdysone (20E). Ligands: The steroidal ligands muristerone A, ponasterone A, α-ecdysone, and 20-hydroxyecdysone were purchased from Sigma Chemical Company and Invitrogen. The non-steroidal ligands: N-(2-ethyl-3-methoxybenzoyl)-N'-(3,5-dimethylbenzoyl)-N'-tert-butylhydrazine (GS™-E non-steroidal ligand); N'-tert-butyl-N'-(3,5-dimethylbenzoyl)-3-methoxy-2-methylbenzohydrazide (RH-2485); N-tert-butyl-N'-(4-ethylbenzoyl)-3,5-dimethylbenzohydrazide (RH-5992), and N'-tert-butyl-N'-(3,5-dimethylbenzoyl)-3,4-(1,2-ethylenedioxy)-2-methylbenzohydrazide (RH-125020) are synthetic stable ecdysteroid ligands synthesized at Rohm and Haas Company. All ligands were dissolved in DMSO and the final concentration of DMSO was maintained at 0.1% in both controls and treatments. $^3$H-PonA and $^3$H-α-ecdysone were purchased from New England Nuclear. $^3$H-RH2485 was synthesized at Rohm and Haas Company.

Transfections:

DNAs corresponding to the various switch constructs outlined in Example 1, specifically switches 1.1-1.13, were transfected into mouse NIH3T3 cells (ATCC) or L57 cells (Dr. Peter Cherbas; Indiana University) as follows. Standard methods for culture and maintenance of the cells were followed. Cells were harvested when they reached 50% confluency and plated in 6-, 12- or 24-well plates at 125,000, 50,000, or 25,000 cells, respectively, in 2.5, 1.0, or 0.5 ml of growth medium containing 10% fetal bovine serum (FBS), respectively. The next day, the cells were rinsed with growth medium and transfected for four hours. Superfect™ (Qiagen Inc.) was used for 3T3 cells and Lipofectamine™ (LifeTechnologies) was used for L57 cells as the transfection reagents. For 12-well plates, 4 μl of Superfect™ or Lipofectamine™ was mixed with 100 μl of growth medium. One μg of reporter construct and 0.25 μg of each receptor construct of the receptor pair to be analyzed were added to the transfection mix. A second reporter construct was added [pTKRL (Promega), 0.1 μg/transfection mix] that comprises a *Renilla* luciferase gene operably linked and placed under the control of a thymidine kinase (TK) constitutive promoter and was used for normalization. The contents of the transfection mix were mixed in a vortex mixer and let stand at room temperature for 30 minutes. At the end of incubation, the transfection mix was added to the cells maintained in 400 μl growth medium. The cells were maintained at 37° C. and 5% $CO_2$ for four hours. At the end of incubation, 500 μl of growth medium containing 20% FBS and either dimethylsulfoxide (DMSO; control) or a DMSO solution of steroidal or non-steroidal ligand was added and the cells were maintained at 37° C. and 5% $CO_2$ for 48 hours. The cells were harvested and reporter activity was assayed. The same procedure was followed for 6 and 24 well plates as well except all the reagents were doubled for 6 well plates and reduced to half for 24-well plates.

Reporter Assays:

Cells were harvested 40 hours after adding ligands. 125 μl of passive lysis buffer (part of Dual-luciferase™ reporter assay system from Promega Corporation) were added to each well of the 24-well plate. The plates were placed on a rotary shaker for 15 minutes. Twenty μl of lysate were assayed. Luciferase activity was measured using Dual-luciferase™ reporter assay system from Promega Corporation following the manufacturer's instructions. β-Galactosidase was measured using Galacto-Star™ assay kit from TROPIX following the manufacturer's instructions. All luciferase and β-galactosidase activities were normalized using *Renilla* luciferase as a standard. Fold activities were calculated by dividing normalized relative light units ("RLU") in ligand treated cells with normalized RLU in DMSO treated cells (untreated control).

Example 2

This Example describes the identification of improved non-steroid responsive CfEcR ligand binding domain substitution mutants that exhibit increased activity in response to non-steroidal ligand and decreased activity in response to steroidal ligand. Briefly, Applicants mutated amino acid residues predicted to be critical for ecdysteroid binding into alanine and created GAL4/mutantCfEcR-DEF cDNA gene expression cassettes as described in Example 1 above using the Quikchange PCR-mediated site-directed mutagenesis kit (Stratagene, La Jolla, Calif.). The mutated and the WT cDNAs were tested in GAL4-driven luciferase reporter assays.

Transfections:

DNAs corresponding to the various switch constructs outlined in Example 1, specifically switches 1.1-1.2, were transfected into mouse NIH3T3 cells (ATCC) as follows. Cells were harvested when they reached 50% confluency and plated in 24 well plates at 12,500 cells/well in 0.5 ml of growth medium containing 10% fetal bovine serum (FBS). The next day, the cells were rinsed with growth medium and transfected for four hours. Superfect™ (Qiagen Inc.) was found to be the best transfection reagent for 3T3 cells. Two μl of Superfect™ was mixed with 100 μl of growth medium and 50 ng of either GAL4/wild-type EcR or Gal4/mutant EcR cassette, 50 ng of VP16/LmUSP-EF and 200 ng of pFRLuc were added to the transfection mix. A second reporter construct was added [pTKRL (Promega), 0.05 μg/transfection mix] that comprises a *Renilla* luciferase gene operably linked and placed under the control of a thymidine kinase (TK) constitutive promoter and was used for normalization. The contents of the transfection mix were mixed in a vortex mixer and let stand at room temperature for 30 min. At the end of incubation, the transfection mix was added to the cells maintained in 200 μl growth medium. The cells were maintained at 37° C. and 5% $CO_2$ for four hours. At the end of incubation, 250 μl of growth medium containing 20% FBS and either dimethylsulfoxide (DMSO; control) or a DMSO solution of 10 nM or 2.5 μM PonA steroidal ligand or GS™-E [N-(2-ethyl-3-methoxybenzoyl)N'-(3,5-dimethylbenzoyl)-N'-tert-butylhydrazine] non-steroidal ligand was added and the cells were maintained at 37° C. and 5% $CO_2$ for 40 hours. The cells were harvested and reporter activity was assayed as described above. Fold activities were calculated by dividing normalized relative light units ("RLU") in ligand treated cells with normalized RLU in DMSO treated cells (untreated control).

Two amino acid residues were identified that, when substituted, yield a mutant ecdysone receptor that exhibits increased activity in response to a non-steroid ligand and decreased activity in response to a steroid ligand. The effect of alanine substitution at amino acid residue 52 or 55 of SEQ ID NO: 1 on the activity of the mutated CfEcR-DEF receptor is presented in Table 7 as a fold increase over Gal4/wild-type CfEcR-DEF (WT) switch activity.

TABLE 7

| CfEcR-DEF Mutants that show increased non-steroid activity and decreased steroid activity Fold increase over WT | | |
|---|---|---|
| MUTANTS | 2.5 μM GS ™-E | 2.5 μM PonA |
| T52A | 1.5 | 0.5 |
| T55A | 1.7 | 0.13 |

Example 3

This Example describes the identification of steroid responsive CfEcR ligand binding domain substitution mutants that exhibit increased activity in response to steroidal ligand and significantly decreased activity in response to non-steroidal ligand. In an effort to identify substitution mutations in the CfEcR that increase steroidal ligand activity, but decrease non-steroidal ligand activity, Applicants mutated amino acid residues predicted to be critical for ecdysteroid binding and created GAL4/mutantCfEcR-DEF cDNA gene expression cassettes as described in Example 1 above using PCR-mediated site-directed mutagenesis kit. The mutated and the WT cDNAs corresponding to the various switch constructs outlined above in Examples 1.1 and 1.2 were made and tested in GAL4-driven luciferase reporter assays as described in Example 2 above. Fold activity was calculated by dividing RLUs in the presence of ligand with RLUs in the absence of the ligand.

Specific amino acid residues were identified that, when substituted, yield a mutant ecdysone receptor that exhibits increased activity in response to a steroid ligand and decreased activity in response to a non-steroid ligand. The effect of an amino acid substitution at amino acid residue 52 or 96 of SEQ ID NO: 1 and amino acid substitution at amino acid residues 96, 107 and 175 of SEQ ID NO: 1 on the activity of the mutated CfEcR-DEF receptor is presented in Table 8 as a fold increase over Gal4/wild-type CfEcR-DEF (WT) switch activity.

TABLE 8

Mutants that show increased steroid and
decreased non-steroid activity
Fold increase over WT

| MUTANTS | 2.5 µM GS™E | 2.5 µM PonA | 10 nM GS™E | 10 nM PonA |
|---|---|---|---|---|
| T52L | 0.26 | 3.4 | | |
| V96A | 0.35 | 408 | | |
| V96T | 0.018 | 45 | | |
| V96T/V107I/R175E | | | 0.4 | 485.7 |

Example 4

This Example describes the identification of improved steroid and non-steroid responsive CfEcR ligand binding domain substitution mutants that exhibit increased activity in response to both a steroidal ligand and a non-steroidal ligand. In an effort to identify substitution mutations in the CfEcR that increase both steroidal and non-steroidal ligand activity, Applicants mutated amino acid residues predicted to be critical for steroid binding and created GAL4/mutantCfEcR-DEF cDNA gene expression cassettes as described in Example 1 above using PCR-mediated site-directed mutagenesis. The mutated and the WT cDNAs corresponding to the various switch constructs outlined above in Examples 1.1 and 1.2 were made and tested in GAL4-driven luciferase reporter assays as described in Example 2 above. Fold activity was calculated by dividing RLUs in the presence of ligand with RLUs in the absence of the ligand.

Specific amino acid residues were identified that, when substituted, yield a mutant ecdysone receptor that exhibits increased activity in response to both non-steroid and steroid ligands. The effect of an amino acid substitution at amino acid residue 52, 96, 107 or 175 of SEQ ID NO: 1, amino acid substitution at amino acid residues 107 and 175 of SEQ ID NO: 1, amino acid substitution at amino acid residues 127 and 175 of SEQ ID NO: 1, amino acid substitution at amino acid residues 107 and 127 of SEQ ID NO: 1, amino acid substitution at amino acid residues 107, 127 and 175 of SEQ ID NO: 1, amino acid substitution at amino acid residues 52, 107 and 175 of SEQ ID NO: 1 or amino acid substitution at amino acid residues 96, 107 and 175 of SEQ ID NO: 1 on the activity of the mutated CfEcR-DEF receptor is presented in Table 9 as a fold increase over Gal4/wild-type CfEcR-DEF (WT) switch activity.

TABLE 9

Mutants that show increased steroid and non-steroid activity
Fold increase over WT

| MUTANTS | 2.5 µM GS™E | 2.5 µM PonA | 10 nM GS™E | 10 nM PonA |
|---|---|---|---|---|
| T52V | 17.3 | 35.7 | | |
| T52I | 8 | 8 | | |
| V96D | 3.07 | 3.1 | | |
| V96M | 122 | 3.37 | | |
| V107I | | | 12.4 | 26.6 |
| R175E | | | 22.0 | 11.3 |
| V107I/R175E | | | 386.4 | 1194.4 |
| Y127E/R175E | | | 622.8 | 42.2 |
| V107I/Y127E | | | 314.6 | 35.8 |
| V107I/Y127E/R175E | | | 124.3 | 122.3 |
| T52V/V107I/R175E | | | 62.8 | 136.6 |
| V96A/V107I/R175E | | | 21.1 | 1005.1 |
| T52A/V107I/R175E | | | 2.3 | 20.3 |

Example 5

This Example describes the identification of non-steroid responsive CfEcR ligand binding domain substitution mutants that exhibit significantly decreased activity in response to steroidal ligand but do not affect activity in response to non-steroidal ligand. In an effort to identify substitution mutations in the CfEcR that decrease steroidal ligand activity, but do not affect non-steroidal ligand activity, Applicants mutated amino acid residues predicted to be critical for ecdysteroid binding and created GAL4/mutantCfEcR-DEF cDNA gene expression cassettes as described in Example 1 above using PCR-mediated site-directed mutagenesis. The mutated and the WT cDNAs corresponding to the various switch constructs outlined above in Examples 1.1 and 1.2 were made and tested in GAL4-driven luciferase reporter assays as described in Example 2 above. Fold activity was calculated by dividing RLUs in the presence of ligand with RLUs in the absence of the ligand.

Four amino acid residues were identified that, when substituted, yield mutant ecdysone receptor that exhibit decreased activity in response to a steroid ligand and minimal effect on activity in response to a non-steroid ligand. The effect of an amino acid substitution at amino acid residue 20, 58, 92, or 110 of SEQ ID NO: 1 on the activity of the mutated CfEcR-DEF receptor is presented in Table 10 as a fold increase over Gal4/wild-type CfEcR-DEF (WT) switch activity.

TABLE 10

Mutants that show decreased steroid activity,
but non-steroid activity is unaffected
Fold increase over WT

| MUTANTS | 2.5 µM GS™E | 2.5 µM PonA |
|---|---|---|
| E20A | 0.9 | 0.35 |
| T58A | 0.8 | 0.008 |
| M92A | 0.7 | 0.39 |
| A110P | 0.8 | 0.005 |

As described in Table 10, Applicants have identified point mutations in the ligand binding domain of CfEcR that significantly reduce steroid binding activity. CfEcR point mutants T58A and A110P essentially eliminated steroid binding activity. Interestingly, the non-steroid activity of these point mutants was not significantly affected.

Example 6

Applicants have further characterized the non-steroid A110P CfEcR receptor identified in Example 5 above. This Example demonstrates that the mutation of a critical alanine residue (A110) leads to the disruption of steroid binding and hence transactivation by the EcR in the presence of steroids. However, the binding as well as transactivation by non-steroids is not impaired.

Ligand Binding Assay

Applicants tested the A110P mutant CfEcR receptor in a steroid and non-steroid ligand binding assay to confirm that steroid binding was eliminated. Briefly, PonA binding activity was determined using an in vitro ligand binding assay (LBA). Steroid ligand binding assay (LBA) was performed using $^3$H-PonA (200 Ci/mmol). In vitro translated Gal4/wild-type or A110P mutant CfEcR-DEF and bacterial expressed GST-CfUSP-A BCDEF were used in the assay. The assay was performed with 8 μL of Gal4/wild-type or A110P mutant CfEcR-DEF, 2.5 uL of GST-CfUSP-A/BCDEF, 1 μL of $^3$H-PonA, and 5 2 μL of unlabeled ("cold") PonA as competitor in the presence of T buffer [90 mM Tris pH 8.0, 10 μM DTT composing Complete™ protease inhibitor cocktail used according to the manufacturer's instructions (Boehringer Mannheim)]. The reaction was earned out at room temperature for 1 hour followed by the addition of dextran-coated charcoal (Sigma). The mixture was centrifuged at 7000×g for 10 minutes the amount of $^3$H-PonA in the supernatant was measured. The reactions were done in triphcate. The full-length WT EcR or its A110P mutant were also in vitro translated and transcobed using the TNT system (Promega) according to the manufacturer's instructions and tested in in vitro ligand binding assays using 3H-RH2485, with cold 20E or non-steroids (RH2485 and GS™-E) as competitors. In addition, 5 μL of the in vitro translations were assayed for translation efficiency using SDS-PAGE following standard methods (Maniatis, 1989). The ligand binding results for both the wild-type and A110P mutant CfEcR-DEF receptors were calculated and are shown in FIG. 1.

The two non-steroid ligands, RH2485 and GS™-E, and the steroid ligand 20E tested were able to effectively compete with bound $^3$H-RH2485 suggesting that they are able to bind the WT full-length EcR efficiently (see FIG. 1). However, when the binding of the same ligands by the A110P mutant was examined, binding of the steroid 20E was completely disrupted but the binding of the non-steroids was unaffected (see FIG. 1). These results indicate that the lack of steroid binding in the case of the GAL4CfEcR fusion protein is not an artifact of the truncation or fusion and demonstrates that the A110P mutant CfEcR is a selective non-steroid receptor.

Ligand Affinities of Mutant A110P CfEcR to Various Steroid and Non-Steroid Ligands:

The ligand binding affinities of the A110P GAL4/CfEcR mutant were measured by binding $^3$H-RH2485 and competing it with different concentrations of cold steroids or non-steroids Boefly, 3H-RH2485 was bound to in vitro translated full-length CfEcR and bacterially expressed CfUSP and competed with increasing concentrations of cold steroidal or non-steroidal ligands. The reaction was earned out at room temperature for 1 hour followed by addition of activated dextran coated charcoal and centofugation at 7000×g for 10 minutes at 4° C. The residual $^3$H-RH2485 in the supernatant after centofugation was measured using a scintillation counter. The fraction bound (f bound) values were determined and plotted against the concentration of ligand (in mM). The IC50 values were determined for each of the steroid PonA and MurA and non-steroid N-(2-ethyl-3-methoxybenzoyl)-N'-(3,5-dtmethylbenzoyl)-N'-tert-butylhydrazine (GS™-E non-steroidal ligand), N'-tert-butyl-N'-(3,5-dtmethylbenzoyl)-3-methoxy-2-methylbenzohydrazide (RH-2485); N-tert-butyl-N'-(4-ethylbenzoyl)-3,5-dimethyl-benzohydrazide (RH-35 5992), and N'-tert-butyl-N'-(3,5-dimethylbenzoyl)-3,4-(1,2-ethylenedioxy)-2-methylbenzo-hydrazide (RH-125020) ligands for the WT and the mutant was determined by plotting the fraction bound against the concentration of each ligand.

As shown in Table 11, the IC50 values for steroids PonA and MurA were increased (more than 1 mM) in the case of the A110P mutant compared to the observed nanomolar values for the WT receptor, suggesting that the binding of steroids was impaired in the A110P mutant CfEcR. On the other hand, non-steroid IC50 values were similar for both the A110P mutant and WT receptors (see Table 11). These results confirm Applicants' findings presented in Example 5 above that the A110P substitution mutation results in a non-steroid ecdysone receptor ligand binding domain that has lost the ability to bind steroid ligand.

TABLE 11

IC50 values determined for wild-type and A110P mutant CfEcR-A BCDEF using several steroidal and non-steroidal ligands.

| | Wild-type IC50 (nM) | A110P mutant IC50 (nM) |
|---|---|---|
| Steroids: | | |
| Ponasterone A | 345.95 | >1 mM |
| Muristerone A | 423.99 | >1 mM |
| Non-Steroids: | | |
| GS ™-E | 85.26 | 12.88 |
| RH-5992 | 132.81 | 322.34 |
| RH-2485 | 1.80 × 10$^3$ | 350.42 |
| RH-125020 | 10.11 | 25.71 |

A110P in Truncated CfEcR or Full Length CfEcR Background

To eliminate the possibility that the loss of steroid activity may be due to the truncated CfEcR-DEF receptor or an artifact of the GAL4 fusion protein, Applicants introduced the A110P mutation into the full length (FL) CfEcR (CfEcR-A/BCDEF), fused it to the GAL4 DNA binding domain as described in Example 1.4, and comparatively assayed it in NIH3T3 cells in 24-well plates as described in Example 2 above with full length wild type CfEcR (Example 1.3) in combination with VP16/LmUSP-EF and pFREcRE Luc that comprised the luciferase reporter gene operatively linked to six copies of the ecdysone response element (6×EcRE) and a synthetic TATAA. The transfected cells were grown in the presence of 0.25 or 10 μM PonA or GS™-E and the reporter activity was measured at 40 hours after adding ligand. The cells were harvested and the extracts were assayed for luciferase activity. The results are presented in FIG. 2. The numbers on top of the bars indicate fold increase over DMSO levels.

Figure 2:
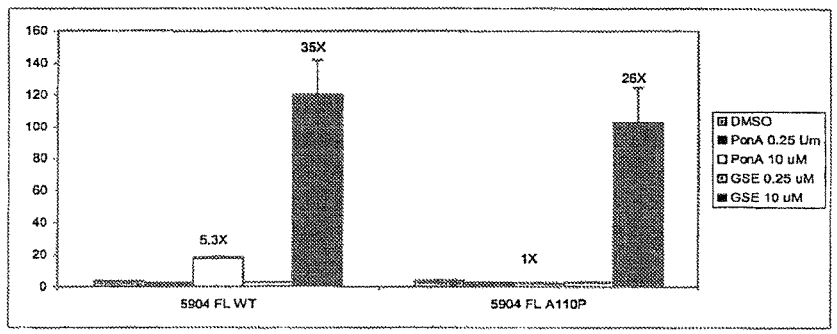
FIG. 2: Transactivation of reporter genes through GAL4/CfEcR-A/BCDEF (full length CfEcR) or its GAL4/A110P mutant version constructs transfected into NIH3T3 cells along with VP16LmUSP-EF and pFREcRE by PonA or GS™-E. The numbers on top of the bars indicate fold increase over DMSO levels.

As shown in FIG. 2, the A110P mutation had a similar effect when introduced into the full-length ecdysone receptor in the context of an EcRE-driven reporter gene. Specifically, PonA activity was completely lost for the full length A110P CfEcR mutant. However, there was no significant difference in non-steroid activity between the full length WT CfEcR and the full-length A110P mutant CfEcR in the presence of GS™-E. These results indicate that the non-responsiveness of the A110P mutant to steroids observed with the GAL4-fusion CfEcR in Example 5 was not an artifact of the GAL4-fusion or truncation of EcR. Thus, Applicants have determined that the A110 amino acid residue is critical for steroidal activity in the full-length ecdysone receptor.

A110 Residue is Critical for Steroidal Activity in Insect Cells

In mammalian cells, the natural ligand of EcR, 20-hydroxyecdysone (20E) does not induce transactivation through a CfEcR-based gene expression system. To determine whether the A110P mutant can respond to 20E, Applicants tested this A110P mutant-based gene expression system in an EcRE-driven reporter assay in insect L57 cells (a *Drosophila melanogaster* cell line that lacks EcR isoform B, the *Drosophila melanogaster* EcR isoform homolog of CfEcR isofrom B from which the A110P mutant is derived, however L57 cells still contain EcR isoform A). The mutation was introduced into the VP16/CfEcR-CDEF fusion protein and operably linked to an baculovirus IE1 promoter and L57 cells were transfected with IE1VP16CfEcRCDEF (Example 1.5) or its A110P mutant version DNA (Example 1.6) along with a pMK43.2 β-galactosidase reporter gene under the control of 6× ecdysone response elements ("6XEcRE"; the pMK43.2 construct was obtained from Michael Koelle at Stanford University) in 24-well plates. Reporter activity for A110P mutant-based gene expression system transactivation was measured after 40 hours of treatment of the transfected cells with 0, 1, 10, 100, or 1000 nM 20E or GS™-E. The cells were harvested and the extracts were assayed for β-galactosidase (β-gal) and luciferase activity. β-Galactosidase was measured using Galacto-Star™ assay kit from TROPEX following the manufacturer's instructions. The numbers on top of the bars indicate fold increase over DMSO levels. The results are presented in FIG. 3.

Figure 3:
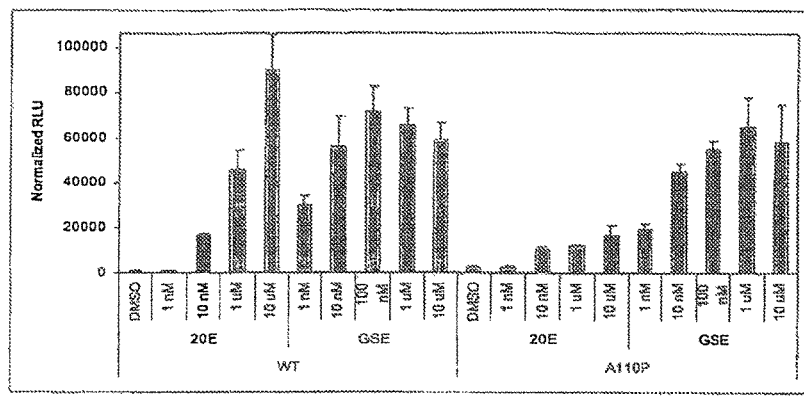
FIG. 3: Transactivation of reporter genes through IE1VP16/CfEcRCDEF (Example 1.5) or its VP16/A110P mutant version constructs (Example 1.6) transfected into L57 cells along with pMK43.2 reporter by 20E or GS™-E. The numbers on top of the bars indicate fold increase over DMSO levels.

In insect cells, the wild-type CfEcR-based gene expression system induced β-gal activity in a dose dependent manner in response to both 20E and GS™-E, whereas the A110P mutant-based gene expression system transactivated reporter gene expression in the presence of GS™-E, however, the L57 cells transfected with the A110P mutant showed slightly increased reporter gene activity in the presence of 20E (see FIG. 3). This low level activity in the presence of 20E is most likely due to endogenous activity of the EcR isoform A within the L57 cells since Applicants have demonstrated that the A110P mutant derived from CfEcR isoform B does not 20E (data not shown).

The A110P mutation had a similar effect when introduced into the full-length receptor in the context of an EcRE-driven reporter gene in the L57 cells indicating that the mutation has an analogous effect in insect cells, presumably in the presence of insect transcriptional co-factors (data not shown). These data confirm Applicants' results from mammalian cells and establish that the A110P mutation results in a drastic effect on the steroidal responsiveness of CfEcR but does not affect the non-steroid responsiveness of CfEcR.

Example 7

Applicants' results presented above in Examples 5 and 6 describe the identification of an alanine residue at position 110 that is a critical residue for steroid but not for non-steroid activity of the CfEcR ligand binding domain. To further characterize the role of residue A110 in CfEcR steroid and non-steroid transactivation of reporter genes, a mini library of CfEcR-DEF receptors was prepared by mutating A110 using degenerate primers. These degenerate PCR primers (A110P random primer pairs comprising either SEQ ID NO: 83 and SEQ ID NO: 84 or SEQ ID NO: 85 and SEQ ID NO: 86; see Table 4) were designed to replace A110 with various amino acid residues. The PCR mutagenesis conditions used were as described above in Example 1. The resulting clones were sequenced to identify the mutants.

Reporter Gene Transactivation of A110 Mutants

Figure 4:
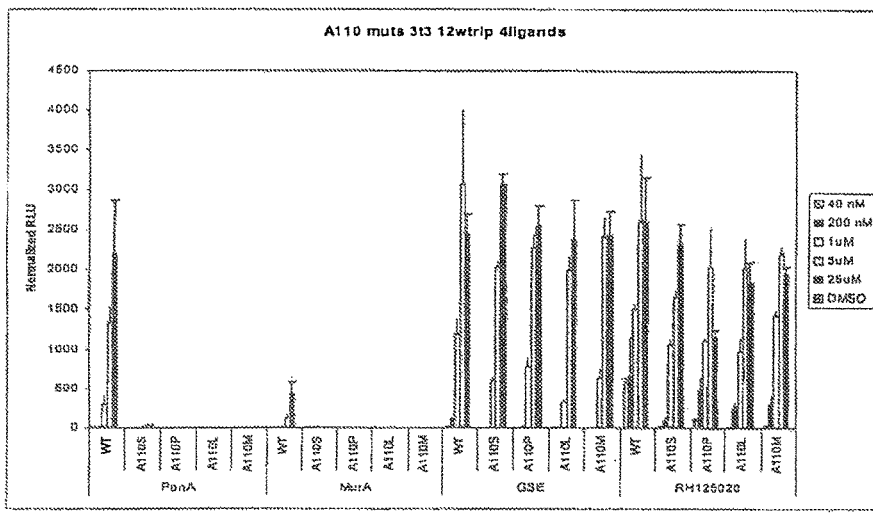
FIG. 4: Transactivation of reporter genes through GAL4/CfEcR-A/BCDEF (full length CfEcR) or its GAL4/A110 mutant versions (A110S, A110P, A1110L, and A110M) constructs transfected into NIH3T3 cells along with VP16LmUSP-EF and pFREcRE by PonA or GS™-E. The numbers on top of the bars indicate fold increase over DMSO levels.

Four mutations: A110S, A110P, A110L, and A110M were obtained. These four mutant and wild-type receptors were assayed in NIH3T3 cells. GAL4 fusions of each of the four mutants or wild-type CfEcR-DEF receptor, VP16LmUSP-EF and pFRLUC were transfected into NIH3T3 cells, the cells were grown in the presence of 0, 0.04, 0.2, 1, 5, or 25 µM PonA, MurA, N-(2-ethyl-3-methoxybenzoyl)-N'-(3,5-dimethylbenzoyl)-N'-tert-butylhydrazine (GS™-E non-steroidal ligand), or N'-tert-butyl-N'-(3,5-dimethylbenzoyl)-3,4-(1,2-ethylenedioxy)-2-methylbenzohydrazide (RH-125020) for 48 hours and the reporter activity was measured. As shown in FIG. 4, the wild-type ecdysone receptor showed reporter activity in the presence of both steroids and non-steroids. However, all mutant receptors showed reporter activity only in the presence of non-steroid ligands but not in the presence of steroid ligands. The A110P mutant exhibited similar non-steroid activity compared to wild-type receptor, however the A110S, A110L and A110M mutants demonstrated lower sensitivity and no detectable transactivation at the two lowest concentrations. These results confirm that an A110 substitution mutant EcR ligand binding domain is characterized by a significantly reduced response to steroids but remains responsive to non-steroids.

Figure 5:
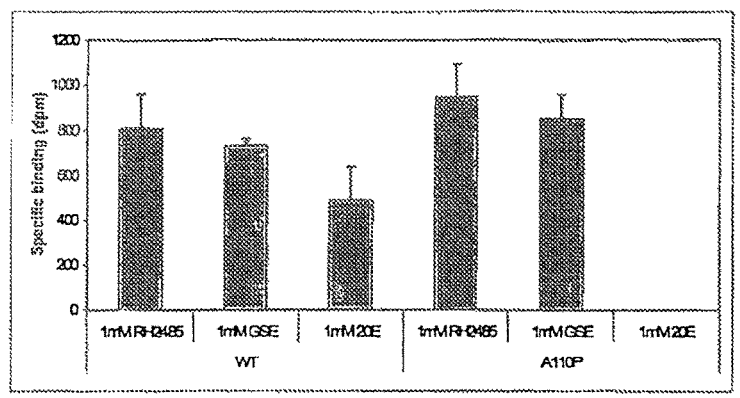
FIG. 5: In vitro $^3$H-PonA ligand binding of wild-type CfEcR-A/BCDEF (full length CfEcR) or its A110 mutant versions (A110S, A110P, A110L, and A110M). The ligand binding values are expressed as specific counts (specific dpm).
Figure 6:
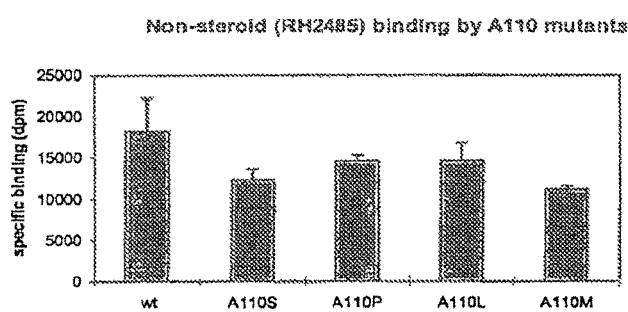
FIG. 6: In vitro $^3$H-RH2485 ligand binding of wild-type CfEcR-A/BCDEF (full length CfEcR) or its A110 mutant versions (A110S, A110P, A110L, and A110M). These values were expressed as specific counts (specific dpm).

Ligand Binding by the A110 Mutants:

Applicants have performed ligand binding assays using $^3$H-PonA or $^3$H-RH2485 (N'-tert-butyl-N'-(3,5-dimethylbenzoyl)-3-methoxy-2-methylbenzohydrazide) radioactively-labeled ligands to determine if the differences in ligand response of substitution mutant and wild-type ecdysone receptors are due to differences at the level of ligand binding. The CfEcR wild-type and mutant receptors were in vitro transcribed and translated and assayed in the presence of bacterially expressed GST-CfUSP-A/BCDEF (full length) PonA binding to A110P mutant was undetectable while other A110 substitution mutants showed 5-10% of wild-type receptor binding (see FIG. 5). Wild-type EcR and all mutants tested showed similar binding to RH-2485, a close analog of GS™-E (see FIG. 6). It may be that the inflexible proline residue of the A110P mutant hinders binding of steroidal but not non-steroidal ligands.

The in vitro translated proteins were analyzed by SDS-PAGE and were found to be translated similar to the WT receptor, indicating that the differences in binding observed between the mutants and wild-type receptor are not due to variation in the amount of proteins present in assay (data not shown). The ligand binding activity correlates with the reporter gene activity in most cases, providing further evidence of Applicants' discovery that the A110 residue plays a critical role in the binding of ecdysteroids, but not non-steroids.

All of the A110 substitution mutants were impaired in steroid binding as well as in their ability to transactivate reporter genes in the presence of steroids in mammalian and insect cells. These mutants maintained wild-type levels of non-steroid binding and reporter gene transactivation in the presence of non-steroids.

The A110 residue, found adjoining the predicted β-sheet between helix 5 and 6, is highly conserved in EcRs from various species of insects, and in RXR, progesterone receptor (PR) and estrogen receptor (ER) further underlining that this residue is critical for ligand binding and thus transactivation. In addition, residue A110 is flanked by other highly conserved residues, some of which may be also critical for ligand binding and/or transactivation. Close comparison of the three-dimensional structures of nuclear receptors show that there are major structural changes even in the conserved LBD among different nuclear receptors. Important changes are observed not only between different nuclear receptor structures, but also complexes of the same receptor when bound to natural and synthetic ligands as in the case of ER. The binding of steroid and non-steroids may reflect a similar situation. The homology models generated suggest that the binding of the two ligands is different, in terms of the helices involved and contact residues. Close examination of the transactivation assay results suggests that the dose responses are slightly different in the two situations. The steroids are less active at lower concentrations while the non-steroids induced activity is several fold higher. However, at higher doses the steroidal and non-steroidal activities are similar. The higher activity of non-steroids at lower concentrations may reflect higher affinity of the non-steroids to the EcR. It has been suggested that the presence of the tert-butyl group allows some non-steroids to form extensive van der Waals contacts with the EcR LBD and thus fits in a groove that is not occupied by ecdysteroids. This may explain to some extent the differences seen in the activities of the steroids and the non-steroids in reporter gene assays at low ligand concentrations. The mechanism by which binding affects conformational changes and thus transactivation potential is yet unknown. However, in the case of the ER, the binding of agonists and antagonists have been shown to induce different conformational changes resulting in displacement of the helix 12. Helix 12 plays an active role in the recruitment and interaction of coactivators to the receptor. In the case of agonists like diethylstilbestrol (DES), coactivator GREP1 binds to a hydrophobic groove on the surface of the LBD formed by helices 3, 4, 5, and 12 and the turn between helices 3 and 4. On the other hand, in the presence a partial antagonist, 4-hydroxytamoxifen (OHT), helix 12 blocks the coactivator recognition groove by mimicking the interactions of GREP NR box with the LBD. The binding of steroid and the non-steroids could also induce subtle conformational changes which affects coactivator recruitment and thus transactivation.

The A110 residue appears to interact with the side chain of the steroid ligand. The introduction of bulkier or inflexible residues in this position would potentially disrupt these interactions and thus docking of the ligand to the LBD. This in turn results in non-activation of the EcR. The identification of a mutant that results in disruption of ecdysteroid binding without affecting non-ecdysteroid binding and activation provides a means for systematic evolution of the EcR to develop an ecdysone inducible system that can be precisely regulated for use in mammalian systems.

Example 8

This Example describes the identification of CfEcR ligand binding domain substitution mutants that exhibit decreased activity in response to both a steroidal ligand and a non-steroidal ligand. These substitution mutants are useful in ligand screening assays for orthogonal ligand identification. In an effort to identify substitution mutations in the CfEcR that decrease both steroidal and non-steroidal ligand activity, Applicants mutated amino acid residues predicted to be critical for ecdysteroid binding and created GAL4/mutantCfEcR-DEF cDNA gene expression cassettes as described in Example 1 above using PCR-mediated site-directed mutagenesis. The mutated and the WT cDNAs corresponding to the various switch constructs outlined above in Examples 1.1 and 1.2 were made and tested in GAL4-driven luciferase reporter assays as described in Example 2 above. Fold activity was calculated by dividing RLUs in the presence of ligand with RLUs in the absence of the ligand.

Seventeen amino acid residues were identified that, when substituted, yield a mutant ecdysone receptor that exhibits decreased activity in response to both non-steroid and steroid ligands. The effect of an amino acid substitution at amino acid residue 21, 48, 51, 59, 62, 93, 95, 109, 120, 123, 125, 218, 219, 223, 230, 234, or 238 of SEQ ID NO: 1 on the activity of the mutated CfEcR-DEF receptor is presented in Table 12 as a fold increase over Gal4/wild-type CfEcR-DEF (WT) switch activity. In addition, two double mutants (R95A/A110P and M218A C219A) and one triple mutant (V107I/A110P/R175E) were made and were also identified as mutated CfEcR-DEF receptors that exhibit decreased activity in response to both non-steroid and steroid ligands (see Table 12).

TABLE 12

Mutants that show decreased steroid and non-steroid activity
Fold increase over WT

| MUTANTS | 2.5 µM GS ™-E | 2.5 µM PonA | 10 nM GS ™-E | 10 nM PonA |
|---|---|---|---|---|
| Q21A | 0.32 | 0.37 | | |
| F48A | 0.007 | 0.007 | | |
| I51A | 0.003 | 0.004 | | |
| V59A | 0.47 | 0.002 | | |
| I62A | 0.12 | 0.004 | | |
| M93A | 0.46 | 0.07 | | |
| R95A | 0.4 | 0.006 | | |
| F109A | 0.22 | 0.005 | | |
| Y120A | 0.001 | 0.006 | | |
| A123F | 0.09 | 0.005 | | |
| M125A | 0.005 | 0.007 | | |
| M218A | 0.001 | 0.001 | | |
| C219A | 0.001 | 0.001 | | |
| L223A | 0.118 | 0.007 | | |
| L230A | 0.001 | 0.006 | | |
| L234A | 0.001 | 0.006 | | |
| W238A | 0.002 | 0.013 | | |
| R95A/A110P | 0.4 | 0.007 | | |
| M218A/C219A | 0.001 | 0.001 | 0.345 | nd* |
| V107I/A110P/R175E | | | | |

*Not detectable

Example 9

This Example describes the introduction of substitution mutations within the *Drosophila melanogaster* EcR (DmEcR) at amino acid residues within the DmEcR ligand binding domain that are analogous to the CfEcR ligand binding domain substitution mutants identified above. Specifically, substitution mutations were introduced at DmEcR amino acid residues 107, 121, 213, and 217 of SEQ ID NO: 2, corresponding to CfEcR amino acid residues 110, 124, 211, and 219 of SEQ ID NO: 1, respectively.

Applicants mutated amino acid residues predicted to be critical for ecdysteroid binding and created GAL4/mutant-DmEcR-CDEF cDNA gene expression cassettes as described in Example 1 above using PCR-mediated site-directed mutagenesis. The mutated and the WT cDNAs corresponding to the various switch constructs outlined above in Examples 1.8 and 1.9 were made and tested in reporter assays in NIH3T3 cells as described in Example 2. Each GAL4/DmEcR-CDEF construct, VP16/LmUSP-EF, and pFRLUC were transfected into NIH3T3 cells and the transfected cells were treated with 2.5 µM GS-™E or Ponasterone A. The cells were harvested and the reporter activity was measured at 48 hours after addition of ligand. The fold induction was calculated by dividing reporter activity in the presence of ligand with the reporter activity in the absence of ligand. From the fold induction, percent wild-type activity was calculated for each mutant. The results are presented in Table 13.

TABLE 13

GAL4/DmEcR-CDEF wild-type and Substitution Mutants G121R, G121L, G217A, and C217 S tested for transactivation in NIH3T3 cells.
Fold increase over WT:

| DmEcR-CDEF Mutant | 2.5 µM Ponasterone A | 2.5 µM GS ™-E |
|---|---|---|
| G121R | 0.05 | 0.0075 |
| G121L | 0.001 | 0.008 |
| C217A | 0.022 | 0.008 |
| C217S | 0.0064 | 0.014 |

As seen in Table 13, both non-steroid and steroid activities were decreased significantly when the DmEcR ligand binding domain was mutated at amino acid residues 121 or 217, indicating that these residues are improtant residues in the ligand binding pocket of DmEcR.

The wild-type and mutant DmEcR-CDEF receptors were also used to make VP16/wild-type or mutantDmEcR-CDEF constructs as described in Example 1.10 and 1.11. VP16DmEcR-CDEF and a 6XEcREβ-gal reporter were transfected into L57 cells and the transfected cells were treated with 1 uM 20-hydroxyecdysone (20E) or GS™-E. The cells were harvested, lysed and the reporter activity was measured as described above in Example 6. The fold induction was calculated by dividing reporter activity in the presence of ligand with the reporter activity in the absence of ligand. From the fold induction, percent wild-type activity was calculated for each mutant. The results are presented in Table 14.

TABLE 14

VP16/DmEcR-CDEF wild-type and Substitution Mutants A107P, G121R, G121L, N213A, G217A, and C217 S tested for transactivation in insect L57 cells.
Fold increase over WT:

| DmEcR-CDEF Mutant | 1 µM 20-hydroxyecdysone | 1 µM GS ™-E |
|---|---|---|
| A107P | 0.09 | 0.9 |
| G121R | 0.5 | 0.92 |
| G121L | 0.09 | 0.15 |
| N213A | 0.01 | 0.08 |
| C217A | 0.48 | 0.70 |
| C217S | 0.39 | 0.92 |

The A107P mutation of DmEcR caused the loss of most steroid activity but had very little effect on non-steroid activity. The G121R and C217S mutations of DmEcR resulted in 50% and 61% reductions respectively in steroid activity but minimal effect on non-steroid activity. The C217A mutation of DmEcR resulted in reduced non-steroid and steroid activities, and the DmEcR mutants G121L and N213A lost sensitivity to both steroids and non-steroids, indicating that these residues are involved in binding to both steroids and non-steroids.

Example 10

This Example describes the introduction of substitution mutations within the *Amblyomma americanum* EcR (AmaEcR) at amino acid residues within the AmaEcR ligand binding domain that are analogous to the CfEcR ligand binding domain substitution mutants identified above. Specifically, substitution mutations were introduced at AmaEcR amino acid residues 91 and 105 of SEQ ID NO: 3, corresponding to CfEcR amino acid residues 96 and 110 of SEQ ID NO: 1, respectively.

Applicants mutated amino acid residues predicted to be critical for ecdysteroid binding and created GAL4/mutant-tAmaEcR-DEF cDNA gene expression cassettes as described in Example 1 above using PCR-mediated site-directed mutagenesis. The mutated and the WT cDNAs corresponding to the various switch constructs outlined above in Examples 1.12 and 1.13 were tested in GAL4-driven luciferase reporter assays in NIH3T3 cells as described in Example 2. GAL4/AmaEcR-DEF, VP16LmUSP-EF and pFRLUC were transfected into NIH3T3 cells and the transfected cells were treated with either 0.2 µM Ponasterone A steroid ligand or 1 µM GS™-E non-steroid ligand. The cells were harvested and the reporter activity was measured at 48 hours after addition of ligand. The fold induction was calculated by dividing reporter activity in the presence of ligand with the reporter activity in the absence of ligand. From the fold induction, percent wild-type activity was calculated for each mutant. The results are presented in Table 15.

TABLE 15

AmaEcR-DEF Substitution Mutants at G91 and A105 in NIH3T3 cells.
Fold increase over WT:

| AmaEcR-DEF Mutant | 0.2 µM Ponasterone A | 1 µM GS ™-E |
|---|---|---|
| G91A | 1.29 | 1.22 |
| A105P | 0.11 | 0.01 |

The G91A mutation of AmaEcR at the homologous amino acid residue position of V96 in CfEcR resulted in increased steroid and non-steroid activities. The A105P mutation of AmaEcR at the homologous amino acid residue position of A110 of CfEcR caused the loss of most steroid activity and essentially eliminated non-steroid activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A method of modulating the expression of a gene in a host cell comprising the steps of:
   a) introducing into the host cell a gene expression modulation system comprising
      i) a first polynucleotide that encodes a first polypeptide comprising: (1) a DNA-binding domain that recognizes a response element associated with a gene whose expression is to be modulated; and 2) a first nuclear receptor ligand binding domain; and
      ii) a second polynucleotide that encodes a second polypeptide comprising: 1) a transactivation domain; and 2) a second nuclear receptor ligand binding domain;
      wherein one of the first or second nuclear receptor ligand binding domains comprises the amino acid sequence of SEQ ID NO: 1 wherein the amino acid sequence of SEQ ID NO: 1 has a single amino acid substitution mutation at amino acid residue 20, 21, 48, 51, 58, 59, 61, 62, 92, 93, 95, 109, 120, 123, 125, 175, 223, 230, 234, or 238 of SEQ ID NO: 1;

b) introducing into the host cell a ligand;
      wherein the gene to be modulated is a component of a gene expression cassette comprising:
      i) a response element recognized by the DNA binding domain;
      ii) a promoter that is activated by the transactivation domain; and
      iii) a gene whose expression is to be modulated;

whereby upon introduction of the ligand into the host cell, expression of the gene of b) iii) is modulated.

2. The method according to claim 1, wherein the ligand is
a) a compound of the formula:

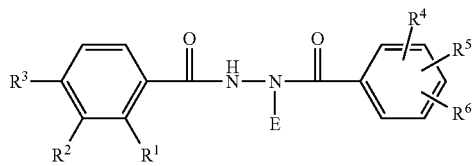

wherein:
E is a (C$_4$-C$_6$)alkyl containing a tertiary carbon or a cyano(C$_3$-C$_5$)alkyl containing a tertiary carbon;
R$^1$ is H, Me, Et, i-Pr, F, formyl, CF$_3$, CHF$_2$, CHCl$_2$, CH$_2$F, CH$_2$Cl, CH$_2$OH, CH$_2$OMe, CH$_2$CN, CN, C≡CH, 1-propynyl, 2-propynyl, vinyl, OH, OMe, OEt, cyclopropyl, CF$_2$CF$_3$, CH═CHCN, allyl, azido, SCN, or SCHF$_2$;
R$^2$ is H, Me, Et, n-Pr, i-Pr, formyl, CF$_3$, CHF$_2$, CHCl$_2$, CH$_2$F, CH$_2$Cl, CH$_2$OH, CH$_2$OMe, CH$_2$CN, CN, C≡CH, 1-propynyl, 2-propynyl, vinyl, Ac, F, Cl, OH, OMe, OEt, O-n-Pr, OAc, NMe$_2$, NEt$_2$, SMe, SEt, SOCF$_3$, OCF$_2$CF$_2$H, COEt, cyclopropyl, CF$_2$CF$_3$, CH═CHCN, allyl, azido, OCF$_3$, OCHF$_2$, O-i-Pr, SCN, SCHF$_2$, SOMe, NH—CN, or joined with R$^3$ and the phenyl carbons to which R$^2$ and R$^3$ are attached to form an ethylenedioxy, a dihydrofuryl ring with the oxygen adjacent to a phenyl carbon, or a dihydropyryl ring with the oxygen adjacent to a phenyl carbon;
R$^3$ is H, Et, or joined with R$^2$ and the phenyl carbons to which R$^2$ and R$^3$ are attached to form an ethylenedioxy, a dihydrofuryl ring with the oxygen adjacent to a phenyl carbon, or a dihydropyryl ring with the oxygen adjacent to a phenyl carbon;
R$^4$, R$^5$, and R$^6$ are independently H, Me, Et, F, Cl, Br, formyl, CF$_3$, CHF$_2$, CHCl$_2$, CH$_2$F, CH$_2$Cl, CH$_2$OH, CN, C≡CH, 1-propynyl, 2-propynyl, vinyl, OMe, OEt, SMe, or SEt; or
b) an ecdysone, 20-hydroxyecdysone, ponasterone A, muristerone A, an oxysterol, a 22(R) hydroxycholesterol, 24(S) hydroxycholesterol, 25-epoxycholesterol, T0901317, 5-alpha-6-alpha-epoxycholesterol-3-sulfate, 7-ketocholesterol-3-sulfate, farnesol, a bile acid, a 1,1-biphosphonate ester, or a Juvenile hormone III.

3. The method according to claim 1, further composing introducing into the host cell a second ligand, wherein the second ligand is 9-cis-retinoic acid or a synthetic analog of a retinoic acid.

4. The method of claim 1, wherein one or more of said amino acid substitution mutations is selected from the group consisting of E20A, Q21A, F48A, I51A, T58A, V59A, L61A, I62A, M92A, M93A, R95A, F109A, Y120A, A123F, M125A, L223A, L230A, L234A, and W238A.

5. The method of claim 1, wherein: said transactivation domain is a VP16 transactivation domain said DNA-binding domain is a GAL4 DNA-binding domain that recognizes said response element; said nuclear receptor ligand binding domain is a *Choristoneura fumiferana* ecdysone receptor ligand binding domain; and wherein said polynucleotide further encodes a chimeric retinoic X receptor ligand binding domain comprising a first polypeptide fragment and a second polypeptide fragment, wherein the first polypeptide fragment is a vertebrate retinoid X receptor ligand binding domain fragment, and the second polypeptide fragment is an invertebrate retinoid X receptor ligand binding domain fragment.

6. The method of claim 1, wherein said DNA binding domain is selected from the group consisting of a GAL4 DNA binding domain, a LexA DNA binding domain, a transcription factor DNA binding domain, a steroid/thyroid hormone nuclear receptor superfamily member DNA binding domain and a bacterial LacZ DNA binding domain.

7. The method of claim 1, wherein said transactivation domain is selected from the group consisting of a steroid/thyroid hormone nuclear receptor transactivation domain, a polyglutamine transactivation domain, a basic or acidic amino acid transactivation domain, a VP16 transactivation domain, a GAL4 transactivation domain, an NF-κB transactivation domain, a p65 transactivation domain and a BP42 transactivation domain.

8. The method of claim 1, wherein said recombinant gene expression system is contained within a vector.

9. The method of claim 8, wherein said vector is a plasmid.

10. The method of claim 8, wherein said vector is an expression vector.

11. The vector of claim 8, wherein said vector is a viral vector.

12. The vector of claim 11, wherein said viral vector is an adenovirus vector.

13. The method of claim 1, wherein said host cell is selected from the group consisting of a bacterial cell, a fungal cell, a yeast cell, a plant cell, an animal cell, a mammalian cell, a mouse cell, and a human cell.

14. The method of claim 1, wherein said host cell is selected from the group consisting of an *Aspergillus* cell, a *Trichoderma* cell, a *Saccharomyces* cell, a *Pichia* cell, a *Candida* cell, a *Hansenula* cell, a *Synechocystis* cell, a *Synechococcus* cell, a *Salmonella* cell, a *Bacillus* cell, an *Acinetobacter* cell, a *Rhodococcus* cell, a *Streptomyces* cell, an *Escherichia* cell, a *Pseudomonas* cell, a *Methylomonas* cell, a *Methylobacter* cell, an *Alcaligenes* cell, a *Synechocystis* cell, an *Anabaena* cell, a *Thiobacillus* cell, a *Methanobacterium* cell and a *Klebsiella* cell.

15. The method of claim 1, wherein said host cell is a plant cell.

16. The method of claim 15, wherein said plant cell is selected from the group consisting of an apple cell, an *Arabidopsis* cell, a bajra cell, a banana cell, a barley cell, a bean cell, a beet cell, a blackgram cell, a chickpea cell, a chili cell, a cucumber cell, an eggplant cell, a favabean cell, a maize cell, a melon cell, a millet cell, a mungbean cell, an oat cell, an okra cell, a *Panicum* cell, a *papaya* cell, a peanut cell, a pea cell, a pepper cell, a pigeonpea cell, a pineapple cell, a *Phaseolus* cell, a potato cell, a pumpkin cell, a rice cell, a sorghum cell, a soybean cell, a squash cell, a sugarcane cell, a sugarbeet cell, a sunflower cell, a sweet potato cell, a tea cell, a tomato cell, a tobacco cell, a watermelon cell, and a wheat cell.

17. The method of claim 13, wherein said host cell is a mammalian cell.

18. The method of claim 17, wherein said mammalian cell is selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

19. The method of claim 18, wherein said mammalian cell is a human cell.

20. The method of claim 1, wherein said host cell is isolated.

21. A method of modulating the expression of a gene in a host cell comprising the steps of:
  a) introducing into the host cell a gene expression modulation system comprising a gene expression cassette that is capable of being expressed in a host cell, wherein the gene expression cassette comprises a polynucleotide that encodes a polypeptide comprising:
    i) a transactivation domain;
    ii) a DNA-binding domain that recognizes a response element associated with a gene whose expression is to be modulated; and
    iii) a nuclear receptor ligand binding domain comprising the amino acid sequence of SEQ ID NO: 1 wherein the amino acid sequence of SEQ ID NO: 1 has
      a single amino acid substitution mutation at amino acid residue 20, 21, 48, 51, 58, 59, 61, 62, 92, 93, 95, 109, 120, 123, 125, 223, 230, 234, or 238 of SEQ ID NO: 1;
  b) introducing into the host cell a ligand;
    wherein the gene to be modulated is a component of a gene expression cassette comprising:
      i) a response element recognized by the DNA binding domain;
      ii) a promoter that is activated by the transactivation domain; and
      iii) a gene whose expression is to be modulated;
    whereby upon introduction of the ligand into the host cell, expression of the gene of b) iii) is modulated.

* * * * *